(12) United States Patent
Wunberg et al.

(10) Patent No.: US 7,115,612 B2
(45) Date of Patent: Oct. 3, 2006

(54) ARYLSULFONAMIDES AS ANTIVIRAL AGENTS

(75) Inventors: Tobias Wunberg, Solingen (DE); Wolfgang Bender, Wuppertal (DE); Peter Eckenberg, Wuppertal (DE); Sabine Hallenberger, Wuppertal (DE); Kerstin Henninger, Wuppertal (DE); Jörg Keldenich, Wuppertal (DE); Armin Kern, Wuppertal (DE); Siegfried Raddatz, Köln (DE); Jürgen Reefschläger, Oldenburg (DE); Gunter Schmidt, Wuppertal (DE); Holger Zimmermann, Wuppertal (DE); Franz Zumpe, Wuppertal (DE); Martin Radtke, Erkrath (DE)

(73) Assignee: Bayer Aktiengesellschaft, Leverkusen (DE)

( * ) Notice: Subject to any disclaimer, the term of this patent is extended or adjusted under 35 U.S.C. 154(b) by 259 days.

(21) Appl. No.: 10/474,916

(22) PCT Filed: Apr. 8, 2002

(86) PCT No.: PCT/EP02/03858

§ 371 (c)(1),
(2), (4) Date: Apr. 12, 2004

(87) PCT Pub. No.: WO02/085869

PCT Pub. Date: Oct. 31, 2002

(65) Prior Publication Data

US 2004/0176374 A1    Sep. 9, 2004

(30) Foreign Application Priority Data

Apr. 19, 2001 (DE) .............. 101 19 137.5

(51) Int. Cl.
*A61K 31/497* (2006.01)
*A61K 31/4709* (2006.01)
*A61K 31/4439* (2006.01)
*A61K 31/433* (2006.01)
*A61K 31/4245* (2006.01)

(52) U.S. Cl. .............. 514/255.05; 514/311; 514/340; 514/361; 514/364; 545/167; 545/269.4; 544/405; 548/127; 548/131

(58) Field of Classification Search .............. 548/127, 548/131; 546/269.4, 167; 544/405
See application file for complete search history.

(56) References Cited

FOREIGN PATENT DOCUMENTS

EP    1172361    1/2002
WO    9937291    7/1999

OTHER PUBLICATIONS

Misra, V. S., Varshneya, M., "Search for New Antiviral Agents. Part I. Synthesis of Aryl Sulfamoyl Benzamido Alkyl/Aralkyl Esters", J. Indian Chem. Soc., 51(II):963-964 (Nov. 1974).
Database Crossfire Beilstein 'Online!, Beilstein Institut Zur Foerderung Der Wissenschaften, Frankfurt Am Main, DE; BRN 75129-34-9; XP002213430 (2003).
Database Crossfire Beilstein 'Online!, Beilstein Institut Zur Foerderung Der Wissenschaften, Frankfurt Am Main, DE; BRN 360648; XP002213431 (2003).

*Primary Examiner*—Kamal A. Saeed
*Assistant Examiner*—Jason M. Nolan

(57) ABSTRACT

The present invention relates to novel sulphonamides of the general formula (I)

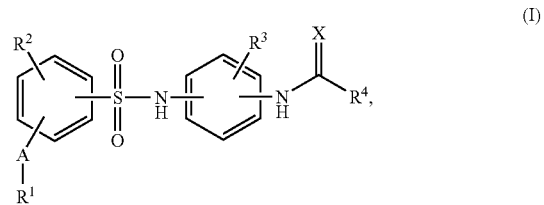

in which the substituents $R^1$, $R^2$, $R^3$, $R^4$ and A and X are as defined in claim 1 and other claims, and also to processes for their preparation and to their use as antiviral agents, in particular against cytomegaloviruses.

20 Claims, No Drawings

ARYLSULFONAMIDES AS ANTIVIRAL AGENTS

The present invention relates to novel compounds, to processes for their preparation and to their use as medicaments, in particular as antiviral agents, in particular against cytomegaloviruses.

From WO 99/37291, compound 2,2-dimethyl-N-[4-[[[4-(4-phenyl-2H-1,2,3-triazol-2-yl)phenyl]-sulphonyl]amino]phenyl]-propanamide is known as having antiviral action.

The present invention relates to compounds of the general formula (I)

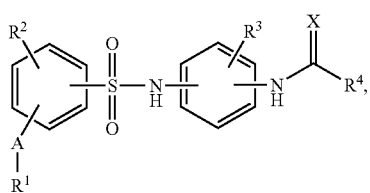

in which $R^2$ and $R^3$ are identical or different and represent hydrogen, hydroxyl, halogen, nitro, cyano, trifluoromethyl, trifluoromethoxy, $(C_1-C_6)$-alkyl, $(C_1-C_6)$-alkoxy or represent a group of the formula

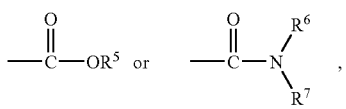

in which $R^5$, $R^6$ and $R^7$ are identical or different and each represents hydrogen or $(C_1-C_6)$-alkyl which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring via a C atom and has one to three heteroatoms selected from the group consisting of N, O and S, $R^1$ represents $(C_6-C_{10})$-aryl, 5- to 10-membered heteroaryl or 5- to 10-membered heterocyclyl having in each case one to three heteroatoms selected from the group consisting of N, O and S, where $R^1$ may be substituted by up to three substituents selected from the group consisting of hydroxyl, amino, mono-$(C_1-C_6)$-alkylamino, di-$(C_1-C_6)$-alkylamino, halogen, nitro, cyano, oxo, $(C_1-C_6)$-alkyl, which for its part may be substituted by amino or hydroxyl, $(C_1-C_6)$-alkoxy, phenyl, 5- or 6-membered heterocyclyl having up to two heteroatoms selected from the group consisting of N, O and S, 5- or 6-membered heteroaryl having one or more heteroatoms selected from the group consisting of N, O and S, —C(O)—O—$R^8$, —C(O)—NR$^9$R$^{10}$, —NH—C(O)—$R^{11}$, —NH—C(O)—C(O)—$R^{12}$ and —NH—SO$_2$—$R^{13}$, where $R^8$, $R^9$ and $R^{10}$ are identical or different and each represents hydrogen or $(C_1-C_6)$-alkyl, or $R^9$ and $R^{10}$ together with the nitrogen atom to which they are attached form a 5- or 6-membered heterocycle which may contain a further nitrogen-or oxygen heteroatom and which may be mono- or disubstituted by identical or different substituents from the group consisting of $(C_1-C_4)$-alkyl, which for its part is optionally substituted by hydroxyl or amino, amino, hydroxyl, $(C_1-C_4)$-alkoxy, oxo, carboxyl and $(C_1-C_4)$-alkoxycarbonyl, $R^{11}$ and $R^{12}$ are identical or different and each represents trifluoromethyl, $(C_1-C_6)$-alkoxy, hydroxyl, or represents $(C_1-C_6)$-alkyl, which is optionally mono- or disubstituted by identical or different constituents from the group consisting of amino, $(C_1-C_6)$-alkoxycarbonylamino, mono-$(C_1-C_6)$-acylamino, hydroxyl, amidino, guanidino, $(C_1-C_6)$-alkoxycarbonyl, carboxyl and phenyl, and $R^{13}$ represents $(C_1-C_6)$-alkyl or $(C_6-C_{10})$-aryl which may in each case be substituted by halogen, amino, hydroxyl, $(C_1-C_4)$-alkoxy or $(C_1-C_4)$-alkyl, $R^4$ represents $(C_1-C_6)$-alkyl which may be substituted up to three times by identical or different substituents from the group consisting of amino, hydroxyl, halogen, $(C_1-C_6)$-alkoxy, $(C_1-C_5)$-alkanoyloxy and phenyl, which for its part is optionally mono- or disubstituted by identical or different substituents from the group consisting of halogen, nitro, cyano, amino and hydroxyl, represents $(C_3-C_7)$-Cycloalkyl which may be substituted up to three times by identical or different substituents from the group consisting of amino, hydroxyl, halogen, $(C_1-C_6)$-alkoxy and $(C_1-C_6)$-alkyl, which for its part is optionally substituted up to three times by identical or different substituents from the group consisting of amino, hydroxyl, halogen and $(C_1-C_6)$-alkoxy, or represents $(C_6-C_{10})$-aryl which is optionally mono- or disubstituted by identical or different substituents from the group consisting of halogen, nitro, cyano, amino and hydroxyl, and in which X represents oxygen or sulphur, and in which nitrogen-containing heterocycles may also be present as N-oxides, and their tautomers, stereoisomers, stereoisomer mixtures and their pharmacological acceptable salts.

In the context of the invention, $(C_1-C_6)$-alkyl represents a straight-chain or branched alkyl radical having 1 to 6 carbon atoms. The following radicals may be mentioned by way of example: methyl, ethyl, n-propyl, isopropyl, n-butyl, t-butyl, n-pentyl and n-hexyl.

In the context of the invention, $(C_3-C_7)$-cycloalkyl represents a cycloalkyl group having 3 to 7 carbon atoms. The following radicals may be mentioned by way of example: cyclopropyl, cyclobutyl, cyclopentyl and cyclohexyl.

In the context of the invention, $(C_1-C_6)$-alkoxy represents a straight-chain or branched alkoxy radical having 1 to 6 carbon atoms. The following radicals may be mentioned by way of example: methoxy, ethoxy, n-propoxy, isopropoxy, t-butoxy, n-pentoxy and n-hexoxy. Preference is given to methoxy and ethoxy.

In the context of the invention, $(C_6-C_{10})$-aryl represents an aromatic radical having 6 to 10 carbon atoms. Preferred aryl radicals are phenyl and naphthyl.

In the context of the invention, aralkyl represents $(C_6-C_{10})$-aryl, which for its part is attached to $(C_1-C_4)$-alkyl. Preference is given to benzyl.

In the context of the invention, mono-$(C_1-C_6)$-alkylamino represents an amino group having a straight-chain, branched or cyclic alkyl substituent having 1 to 6 carbon atoms. The following radicals may be mentioned by way of example:

methylamino, ethylamino, n-propylamino, isopropylamino, cyclopropylamino, t-butylamino, n-pentylamino, cyclopentylamino and n-hexylamino.

In the context of the invention, di-$(C_1-C_6)$-alkylamino represents an amino group having two identical or different straight-chain, branched or cyclic alkyl substituents, having in each case 1 to 6 carbon atoms. The following radicals may be mentioned by way of example: N,N-dimethylamino, N,N-diethyl amino, N-ethyl-N-methylamino, N-methyl-N-n-propylamino, N-methyl-N-cyclopropylamino, N-isopropyl-N-n-propyl-amino, N-t-butyl-N-methylamino, N-ethyl-N-n-pentylamino and N-n-hexyl-N-methylamino.

In the context of the invention, $(C_1-C_6)$-alkoxycarbonyl represents a straight-chain or branched alkoxy-radical having 1 to 6 carbon atoms, which is attached via a carbonyl group. Preference is given to a straight-chain or branched alkoxycarbonyl radical having 1 to 4 carbon atoms. The following radicals may be mentioned by way of example and by way of preference: methoxycarbonyl, ethoxycarbonyl, n-propoxycarbonyl, isopropoxycarbonyl and t-butoxycarbonyl.

In the context of the invention, $(C_1-C_6)$-alkoxycarbonylamino represents an amino group having a straight-chain or branched alkoxycarbonyl substituent which has 1 to 6 carbon atoms in the alkoxy radical and is attached via the carbonyl group. Preference is given to an alkoxycarbonylamino radical having 1 to 4 carbon atoms in the alkoxy radical. The following radicals may be mentioned by way of example and by way of preference: methoxycarbonylamino, ethoxycarbonylamino, n-propoxy-carbonylamino and t-butoxycarbonylamino.

In the context of the invention, mono-$(C_1-C_6)$-acylamino represents an amino group having a straight-chain or branched alkanoyl substituent which has 1 to 6 carbon atoms and is attached via the carbonyl group. Preference is given to a monoacylamino radical having 1 or 2 carbon atoms. The following radicals may be mentioned by way of example and by way of preference: formamido, acetamido, propionamido, n-butyramido and pivaloylamido.

In the context of the invention, $(C_1-C_5)$-alkanoyloxy preferably represents a straight-chain or branched alkyl radical having 1 to 5 carbon atoms which carries a doubly attached oxygen atom in the 1-position and which is attached in the 1-position via a further oxygen atom. Preference is given to a straight-chain or branched alkanoyloxy radical having 1 to 3 carbon atoms. The following radicals may be mentioned by way of example and by way of preference: acetoxy, propionoxy, n-butyroxy, i-butyroxy and pivaloyloxy.

In the context of the invention, halogen generally represents fluorine, chlorine, bromine and iodine. Preference is given to fluorine, chlorine and bromine. Particular preference is given to fluorine and chlorine.

In the context of the invention, 5- to 10-membered heteroaryl represents 5- to 10-membered hetero-containing aromatic rings which may contain 1 to 4 heteroatoms selected from the group consisting of O, S and N, including, for example: pyridyl, furyl, thienyl, pyrrolyl, imidazolyl, pyrazolyl, pyrazinyl, pyrimidinyl, pyridazinyl, indolicenyl, indolyl, benzo[b]thienyl, benzo[b]furyl, indazolyl, quinolyl, isoquinolyl, naphthyridinyl, quinazolinyl, etc.

In the context of the invention, 5- to 10-membered or 5- or 6-membered saturated or partially unsaturated heterocyclyl having up to 3 heteroatoms from the croup consisting of S, N and O generally represents a mono- or bicyclic heterocycle which may contain one or more double bonds and which is attached via a ring carbon atom or a ring nitrogen atom. The following radicals may be mentioned by way of example: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin-3-yl, 1,2-dihydropyridin-1-yl, 1,4-dihydropyridin-1-yl, piperazin-1-yl, morpholin-1-yl, azepin-1-yl, 1,4-diazepin-1-yl. Preference is given to piperidinyl, morpholinyl and pyrrolidinyl.

1,2,4-Oxadiazole which is attached via the 3- or 5-position represents an oxadiazole which is attached to the phenylsulphonamide via the ring carbon atom in the 3- or 5-position.

In the context of the invention, the preferred salts are pharmacologically acceptable salts of the compounds according to the invention.

Pharmacologically acceptable salts of the compounds according to the invention may be acid addition salts of the compounds according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

However, salts that may be mentioned include salts with customary bases, such as, for example, alkali metal salts (for example sodium salts or potassium salts), alkaline earth metal salts (for example calcium salts or magnesium salts) or ammonium salts, derived from ammonia or organic amines, such as, for example, diethylamine, triethylamine, ethyldiusopropylamine, procaine, dibenzylamine, N-methylmorpholine, dihydroabietylamine, 1-ephenamine or methylpiperidine, or derived from natural amino acids, such as, for example, glycine, lysine, arginine or histidine.

The compounds according to the invention may exist in stereoisomeric forms which are either like image and mirror image (enantiomers) or which are not like image and mirror image (diastereomers). The invention relates both to the enantiomers or diastereomers and to their respective mixtures. The racemic forms can, like the diastereomers, be separated into the stereoisomerically uniform components in a manner known per se.

In addition, the invention also embraces prodrugs of the compounds according to the invention. According to the invention, prodrugs are derivatives of the compounds of the general formula (I) which for their part may be biologically less active or even inactive, but, following administration, are converted under physiological conditions into the corresponding biologically active form (for example metabolically, solvolytically or in another manner).

The invention also relates to compounds of the general formula (I), in which $R^2$ and $R^3$ are identical or different and represent hydrogen, hydroxyl, halogen, nitro, cyano, trifluoromethyl, trifluoromethoxy, $(C_1-C_6)$-alkyl, $(C_1-C_6)$-alkoxy or represent a group of the formula

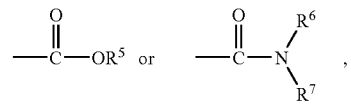

in which

R$^5$, R$^6$ and R$^7$ are identical or different and each represents hydrogen or (C$_1$–C$_6$)-alkyl, which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring via a C atom and has one to three heteroatoms selected from the group consisting of N, O and S, R$^1$ represents (C$_6$–C$_{10}$)-aryl, 5- to 10-membered heteroaryl or 5- to 10-membered heterocyclyl having in each case one to three heteroatoms selected from the group consisting of N, O and S, where R$^1$ may be substituted by up to three substituents selected from the group consisting of hydroxyl, amino, mono-(C$_1$–C$_6$)-alkylamino, di-(C$_1$–C$_6$)-alkylamino, halogen, nitro, cyano, oxo, (C$_1$–C$_6$)-alkyl, which for its part may be substituted by amino or hydroxyl, (C$_1$–C$_6$)-alkoxy, phenyl, 5- or 6-membered heteroaryl having one or more heteroatoms selected from the group consisting of N, O and S, —C(O)—O—R$^8$, —C(O)—NR$^9$R$^{10}$ and —NH—C(O)—R$^{11}$, where R$^8$, R$^9$ and R$^{10}$ are identical or different and each represents hydrogen or (C$_1$–C$_6$)-alkyl, and R$^{11}$ represents (C$_1$–C$_6$)-alkyl which is optionally mono- or disubstituted by identical or different substituents from the group consisting of amino, hydroxyl, guanidino, carboxyl and phenyl, R$^4$ represents (C$_1$–C$_6$)-alkyl which may be substituted up to three times by identical or different substituents from the group consisting of amino, hydroxyl, halogen, (C$_1$–C$_6$)-alkoxy and phenyl, which for its part is optionally mono- or disubstituted by identical or different substituents from the group consisting of halogen, nitro, cyano, amino and hydroxyl, represents (C$_3$–C$_7$)-cycloalkyl which may be substituted up to three times by identical or different substituents from the group consisting of amino, hydroxyl, halogen, (C$_1$–C$_6$)-alkoxy and (C$_1$–C$_6$)-alkyl, which for its part is optionally substituted up to three times by identical or different substituents from the group consisting of amino, hydroxyl, halogen and (C$_1$–C$_6$)-alkoxy, or represents (C$_6$–C$_{10}$)-aryl which is optionally mono- or disubstituted by identical or different substituents from the group consisting of halogen, nitro, cyano, amino and hydroxyl, and in which X represents oxygen or sulphur, and in which nitrogen-containing heterocycles may also be present as N-oxides, and their tautomers, stereoisomers, stereoisomer mixtures and their pharmacologically acceptable salts.

The invention preferably relates to compounds of the general formula (I), in which R$^2$ and R$^3$ are identical or different and represent hydrogen, hydroxyl, halogen, nitro, cyano, trifluoromethyl, trifluoromethoxy, (C$_1$–C$_6$)-alkyl, (C$_1$–C$_6$)-alkoxy or represent a group of the formula

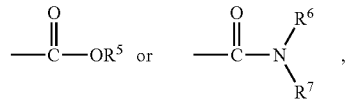

in which

R$^5$, R$^6$ and R$^7$ are identical or different and each represents hydrogen or (C$_1$–C$_6$)-alkyl, which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring via a C atom and has one to three heteroatoms selected from the group consisting of N, O and S, R$^1$ represents (C$_6$–C$_{10}$)-aryl, 5- to 10-membered heteroaryl or 5- to 10-membered heterocyclyl having in each case one to three heteroatoms selected from the group consisting of N, O and S, where R$^1$ may be substituted by up to three substituents selected from the group consisting of hydroxyl, amino, mono-(C$_1$–C$_6$)-alkylamino, di-(C$_1$–C$_6$)-alkylamino, halogen, nitro, cyano, oxo, (C$_1$–C$_6$)-alkyl, which for its part may be substituted by amino or hydroxyl, (C$_1$–C$_6$)-alkoxy, phenyl, 5- or 6-membered heteroaryl having one or more heteroatoms selected from the group consisting of N, O and S, —C(O)—O—R$^8$, —C(O)—NR$^9$R$^{10}$ and —NH—C(O)—R$^{11}$, where R$^8$, R$^9$ and R$^{10}$ are identical or different and each represents hydrogen or (C$_1$–C$_6$)-alkyl, and R$^{11}$ represents (C$_1$–C$_6$)-alkyl, which is optionally mono- or disubstituted by identical or different substituents from the group consisting of amino, hydroxyl, guanidino, carboxyl and phenyl, R$^4$ represents (C$_1$–C$_6$)-alkyl which may be substituted up to three times by identical or different substituents from the group consisting of amino, hydroxyl, halogen, (C$_1$–C$_6$)-alkoxy and phenyl, which for its part is optionally mono- or disubstituted by identical or different substituents from the group consisting of halogen, nitro, cyano, amino and hydroxyl, represents (C$_3$–C$_7$)-cycloalkyl which may be substituted up to three times by identical or different substituents from the group consisting of amino, hydroxyl, halogen, (C$_1$–C$_6$)-alkoxy and (C$_1$–C$_6$)-alkyl, which for its part is optionally substituted up to three times by identical or different substituents from the group consisting of amino, hydroxyl, halogen and (C$_1$–C$_6$)-alkoxy, or represents (C$_6$–C$_{10}$)-aryl which is optionally mono- or disubstituted by identical or different substituents from the group consisting of halogen, nitro, cyano, amino and hydroxyl, and in which X represents oxygen, and in which nitrogen-containing heterocycles may also be present as N-oxides, and their tautomers, stereoisomers, stereoisomer mixtures and their pharmacologically acceptable salts.

The invention preferably also relates to compounds of the general formula (I), in which R$^2$ and R$^3$ are identical or different and represent hydrogen or halogen, A represents the radical (A-I)

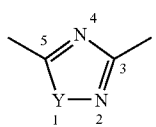

(A-I)

which is attached to the adjacent phenyl ring via one of the carbon atoms in position 3 or 5,
and in which
Y represents oxygen or sulphur, or
A represents the radical (A-II)

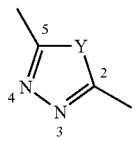

(A-II)

which is attached to the adjacent phenyl ring via one of the carbon atoms in position 2 or 5,
and in which
Y represents oxygen or sulphur,
$R^1$ represents 5- to 10-membered heteroaryl or 5- or 10-membered heterocyclyl having in each case up to three heteroatoms selected from the group consisting of N, O and S, or represents phenyl, where
$R^1$ may be substituted by one to three substituents selected from the group consisting of $(C_1-C_4)$-alkyl, which for its part is optionally substituted by hydroxyl or amino, hydroxyl, oxo, halogen, amino, mono-$(C_1-C_4)$-alkylamino, di-$(C_1-C_4)$-alkylamino and —NH—C(O)—$R^{11}$, where
$R^{11}$ represents $(C_1-C_6)$-alkyl which is optionally mono- or disubstituted by identical or different substituents from the group consisting of amino, hydroxyl, guanidino and carboxyl,
$R^4$ represents $(C_1-C_4)$-alkyl which may be substituted up to three times by identical or different substituents from the group consisting of amino, hydroxyl, fluorine, chlorine and $(C_1-C_4)$-alkoxy,
represents $(C_3-C_5)$-cycloalkyl, which may be substituted up to three times by identical or different substituents from the group consisting of amino, hydroxyl, fluorine, chlorine, $(C_1-C_4)$-alkoxy and $(C_1-C_4)$-alkyl, which for its part is optionally substituted up to three times by identical or different substituents from the group consisting of amino, hydroxyl, fluorine, chlorine and $(C_1-C_4)$-alkoxy,
and in which
X represents oxygen or sulphur,
and in which nitrogen-containing heterocycles may also be present as N-oxides,
and their tautomers, stereoisomers, stereoisomer mixtures and their pharmacologically acceptable salts.

The invention particularly preferably relates to compounds of the general formula (I), in which
$R^2$ and $R^3$ are identical or different and represent hydrogen or halogen, A represents the radical (A-I)

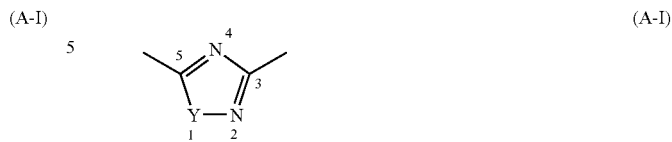

(A-I)

which is attached to the adjacent phenyl ring via one of the carbon atoms in position 3 or 5,
and in which
Y represents oxygen or sulphur, or
A represents the radical (A-II)

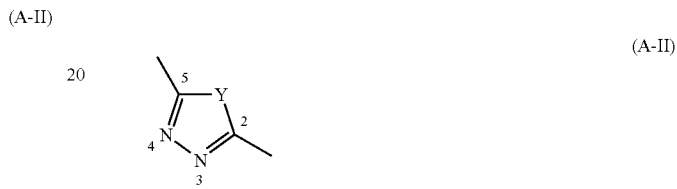

(A-II)

which is attached to the adjacent phenyl ring via one of the carbon atoms in position 2 or 5,
and in which
Y represents oxygen or sulphur,
$R^1$ represents 5- to 10-membered heteroaryl or 5- or 10-membered heterocyclyl having in each case up to three heteroatoms selected from the group consisting of N, O and S, or represents phenyl, where
$R^1$ may be substituted by one to three substituents selected from the group consisting of $(C_1-C_4)$-alkyl, which for its part is optionally substituted by hydroxyl or amino, hydroxyl, oxo, halogen, amino, mono-$(C_1-C_4)$-alkylamino, di-$(C_1-C_4)$-alkylamino and —NH—C(O)—$R^{11}$, where
$R^{11}$ represents $(C_1-C_6)$-alkyl which is optionally mono- or disubstituted by identical or different substituents from the group consisting of amino, hydroxyl, guanidino and carboxyl,
$R^4$ represents $(C_1-C_4)$-alkyl which may be substituted up to three times by identical or different substituents from the group consisting of amino, hydroxyl, fluorine, chlorine and $(C_1-C_4)$-alkoxy, or
represents $(C_3-C_5)$-cycloalkyl which may be substituted up to three times by identical or different substituents from the group consisting of amino, hydroxyl, fluorine, chlorine, $(C_1-C_4)$-alkoxy and $(C_1-C_4)$-alkyl, which for its part is optionally substituted up to three times by identical or different substituents from the group consisting of amino, hydroxyl, fluorine, chlorine and $(C_1-C_4)$-alkoxy,
and in which
X represents oxygen,
and their tautomers, stereoisomers, stereoisomer mixtures and their pharmacologically acceptable salts.

The invention particularly preferably relates to compounds of the general formula (I), in which R² and R³ represent hydrogen, A represents one of the radicals

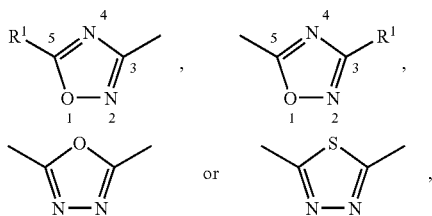

R¹ represents a radical selected from the group consisting of phenyl, pyridyl, pyrazinyl, thiazolyl, thiadiazolyl, quinolinyl, isoquinolinyl, oxazolyl, pyrazolyl, imidazolyl, pyrrolyl and indolyl, where R¹ may be substituted by one or two substituents selected from the group consisting of methyl, aminomethyl, hydroxyl, bromine, chlorine, fluorine, amino, dimethylamino and —NH—C(O)—R¹¹, where R¹¹ represents $(C_1-C_6)$-alkyl which is optionally mono- or disubstituted by identical or different substituents from the group consisting of amino, hydroxyl, guanidino and carboxyl, R⁴ represents tert-butyl which is optionally substituted up to three times by identical or different substituents from the group consisting of hydroxyl, fluorine and chlorine, or represents cyclopropyl or cyclobutyl which are substituted by methyl, which for its part is optionally substituted by hydroxyl, fluorine or chlorine, and in which X represents oxygen, and in which nitrogen-containing heterocycles may also be present as N-oxides, and their tautomers, stereoisomers, stereoisomer mixtures and their pharmacologically acceptable salts.

With particular preference, the invention relates to compounds of the general formula (I), in which R² and R³ represent hydrogen, A represents one of the radicals

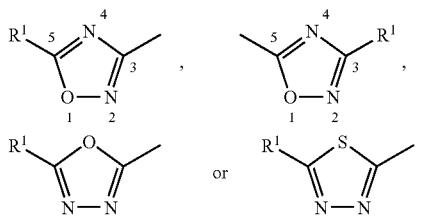

R¹ represents a radical selected from the group consisting (of phenyl, pyridyl, pyrazinyl, thiazolyl, thiadiazolyl, quinolinyl, isoquinolinyl, oxazolyl, pyrazolyl, imidazolyl, pyrrolyl and indolyl, where R¹ may be substituted by one or two substituents selected from the group consisting of methyl, aminomethyl, hydroxyl, bromine, chlorine, fluorine, amino, dimethylamino and —NH—C(O)—R¹¹, where R¹¹ represents $(C_1-C_6)$-alkyl which is optionally mono- or disubstituted by identical or different substituents from the group consisting of amino, hydroxyl, guanidino and carboxyl, R⁴ represents tert-butyl which is optionally substituted up to three times by identical or different substituents from the group consisting of hydroxyl fluorine and chlorine, or represents cyclopropyl or cyclobutyl which are substituted by methyl, which for its part is optionally substituted by hydroxyl, fluorine- or chlorine, and in which X represents oxygen.

In a preferred embodiment, the invention relates to compounds of the general formula (Ia)

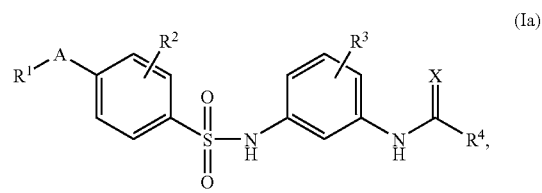

(Ia)

in which

R¹, R⁴, A and X are as defined above, and

R² and R³ are identical or different and represent hydrogen, hydroxyl, halogen, nitro, cyano, trifluoromethyl, trifluoromethoxy, $(C_1-C_6)$-alkyl or $(C_1-C_6)$-alkoxy.

In a further preferred embodiment, the invention relates to compounds of the general formula (I), in which R⁴ represents one of the radicals

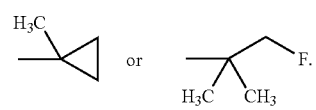

In a further preferred embodiment, the invention relates to compounds of the general formula (I), in which A represents 1,2,4-oxadiazole which is attached via the 3-position.

Very particularly preferred compounds of the present invention are sulphonamides which are selected from the group of the following compounds:

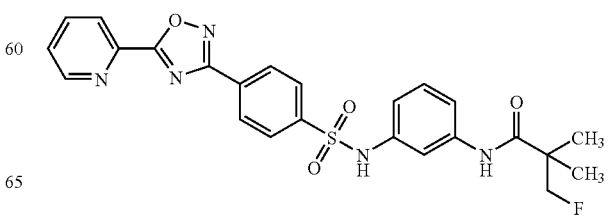

-continued

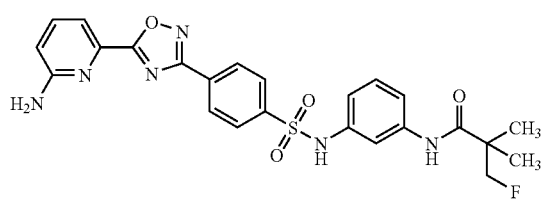

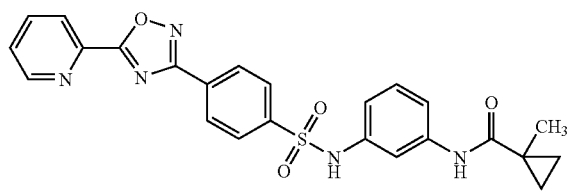

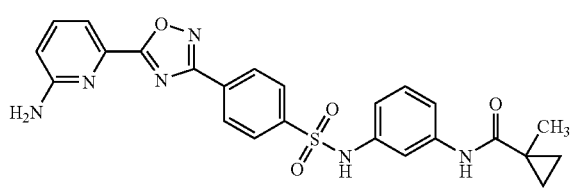

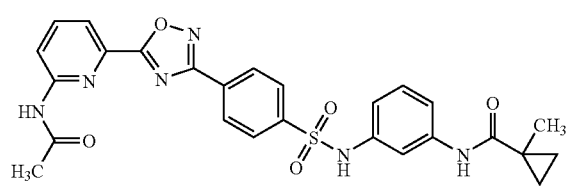

The invention furthermore relates to processes for preparing compounds of the general formula (I), which are characterized in that

[A] nitro-anilines of the general formula [A-1]

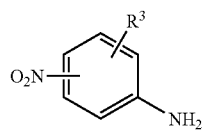
[A-1]

in which
R³ has the meaning given above,
are reacted with compounds of the general formula [A-2]

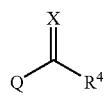
[A-2]

in which
X and R⁴ have one of the meanings given above, and
Q represents a leaving group, for example halogen, preferably chlorine or bromine,
in inert solvents in the presence of a base to give compounds of the general formula [A-3]

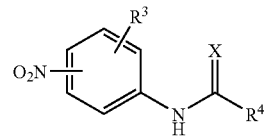
[A-3]

in which
X, R³ and R⁴ have one of the meanings given above, and

[B] the nitro-aromatic compounds of the general formula [A-3] are reduced in inert solvents, for example in the presence of transition metal catalysts and hydrogen, to aromatic amines of the general formula [B-1]

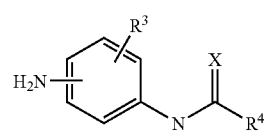
[B-1]

in which
X, R³ and R⁴ have one of the meanings given above, and

[C] amines of the general formula [B-1] are reacted with sulphonic acid derivatives of the general formula [C-1]

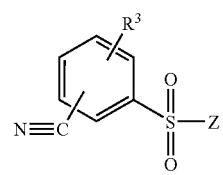
[C-1]

in which
R² has the meaning given above, and
Z represents a leaving group, for example halogen, preferably chlorine or bromine,
in inert solvents, in the presence of a base, to give compounds of the general formula [C-2]

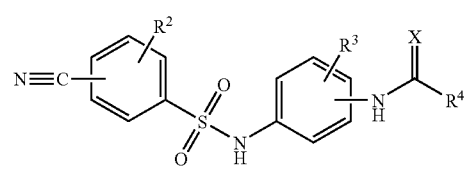
[C-2]

in which
X, R², R³ and R⁴ have one of the meanings given above, and

[D] the nitriles of the general formula [C-2] are reacted in polar protic solvents, for example alcohols, at elevated temperature, preferably the boiling point of the solvent, in the presence of a base with hydroxylamine to give amidoximes of the general formula [D-1]

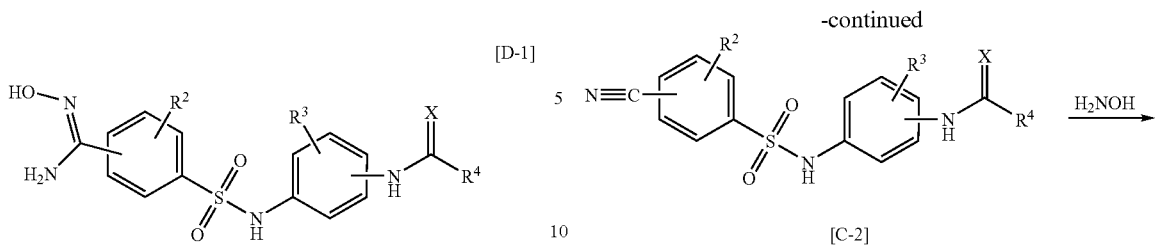

in which

X, $R^2$, $R^3$ and $R^4$ have one of the meanings given above, and

[E] amidoximes of the general formula [D-1] are acylated with a carboxylic acid of the general formula [E-1]

$$R^1\text{—COOH} \quad [E-1]$$

in which $R^1$ has the meaning given above, in the presence of a condensing agent, for example benzotriazolyl-N-oxi-tris(dimethylamino)phosphonium hexafluorophosphate (PyBOP), or other activating agents known from peptide chemistry, and also acid chlorides, and a base in a polar aprotic solvent, for example tetrahydrofuran, and the acylated amidoxime is isolated as a crude product and then cyclized in a high-boiling polar solvent, for example DMF, at elevated temperature, to give the 1,2,4-oxadiazole.

The process according to the invention for preparing 1,2,4-oxadiazoles attached via the 3-position is illustrated in an exemplary manner by the formula scheme below:

Scheme 1:

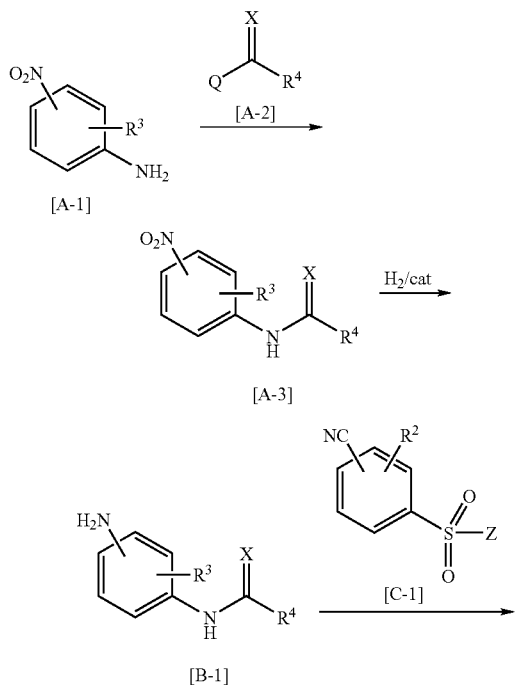

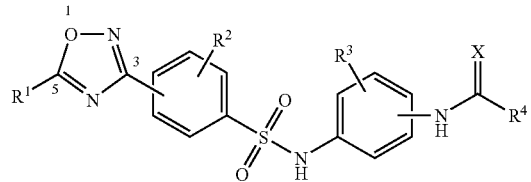

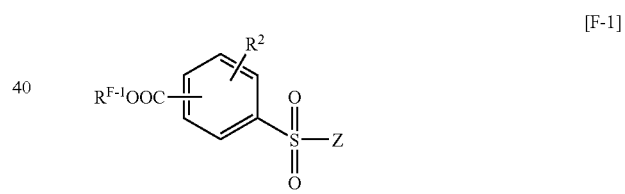

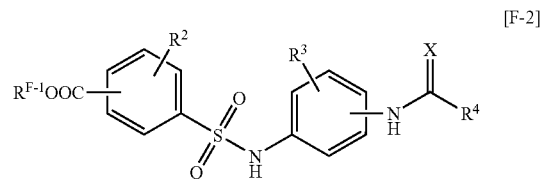

The invention furthermore relates to processes for preparing compounds of the general formula (I), characterized in that

[F] sulphonyl halides of the general formula [F-1]

[F-1]

in which $R^2$ and Z have the meaning given above, and $R^{F-1}$ represents $(C_1–C_4)$-alkyl, aralkyl or a carboxylic acid protective group, are reacted in the presence of a base with anilines of the general formula [B-1] to give sulphonamides of the general formula [F-2]

[F-2]

in which $R^{F-1}$, $R^2$, $R^3$, $R^4$ and X have the meaning given above, and the group $R^{F-1}$ is then cleaved off from the compounds of the general formula [F-2], for example in the presence of hydroxyl anions, giving sulphonamides of the general formula [F-3],

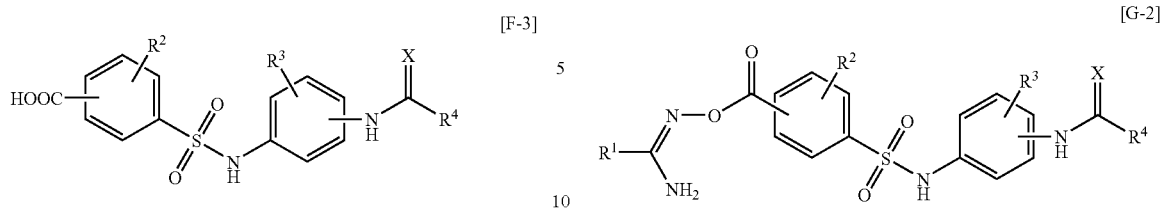

and

[G] amid-oximes of the general formula [G-1]

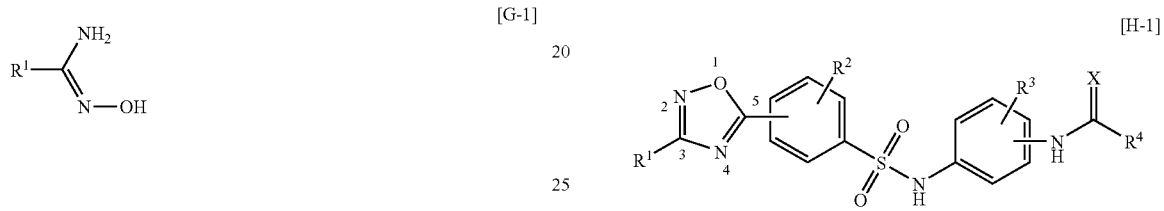

in which

R¹ has the meaning given above, are condensed with compounds of the general formula [F-3] to give compounds of the general formula [G-2], in which R¹, R², R³, R⁴ and X have the meaning given above, and

[H] compounds of the general formula [G-2] are cyclized thermally to give the 1,2,4-oxadiazoles, attached via the 5-position, of the general formula [H-1]

in which

R¹, R², R³, R⁴ and X have the meaning given above.

The compounds according to the invention can be prepared, for example, according to the formula scheme below:

Scheme 2:

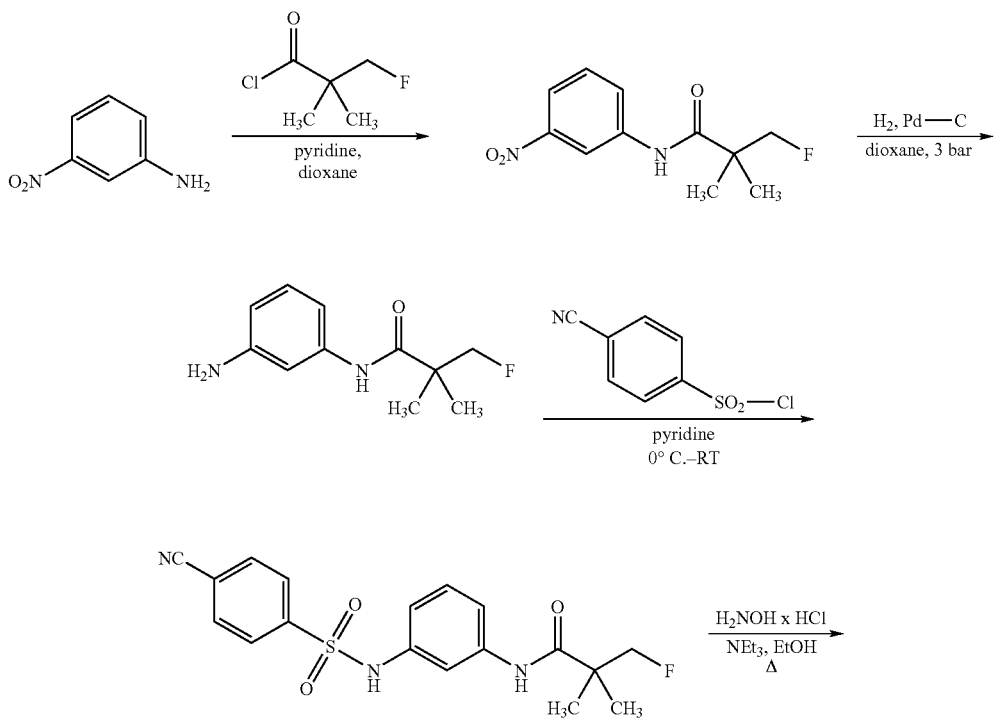

-continued
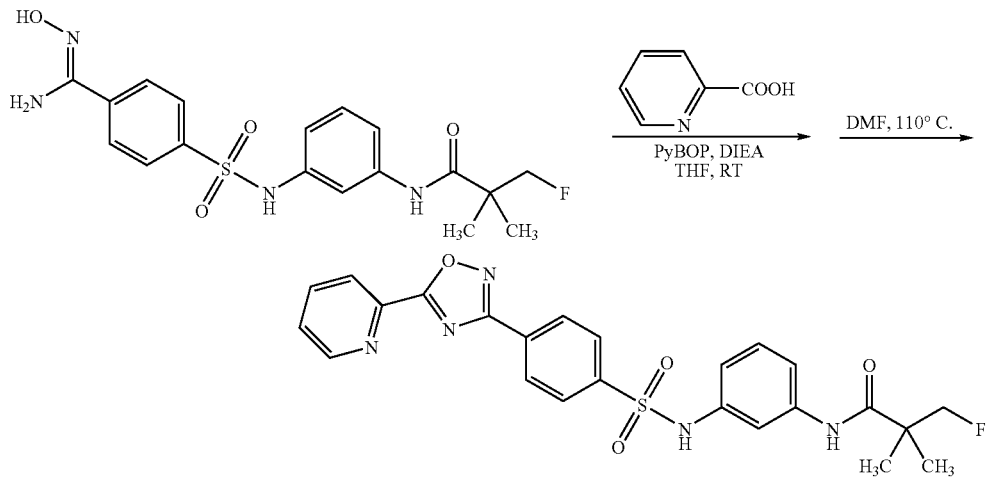
Scheme 3:
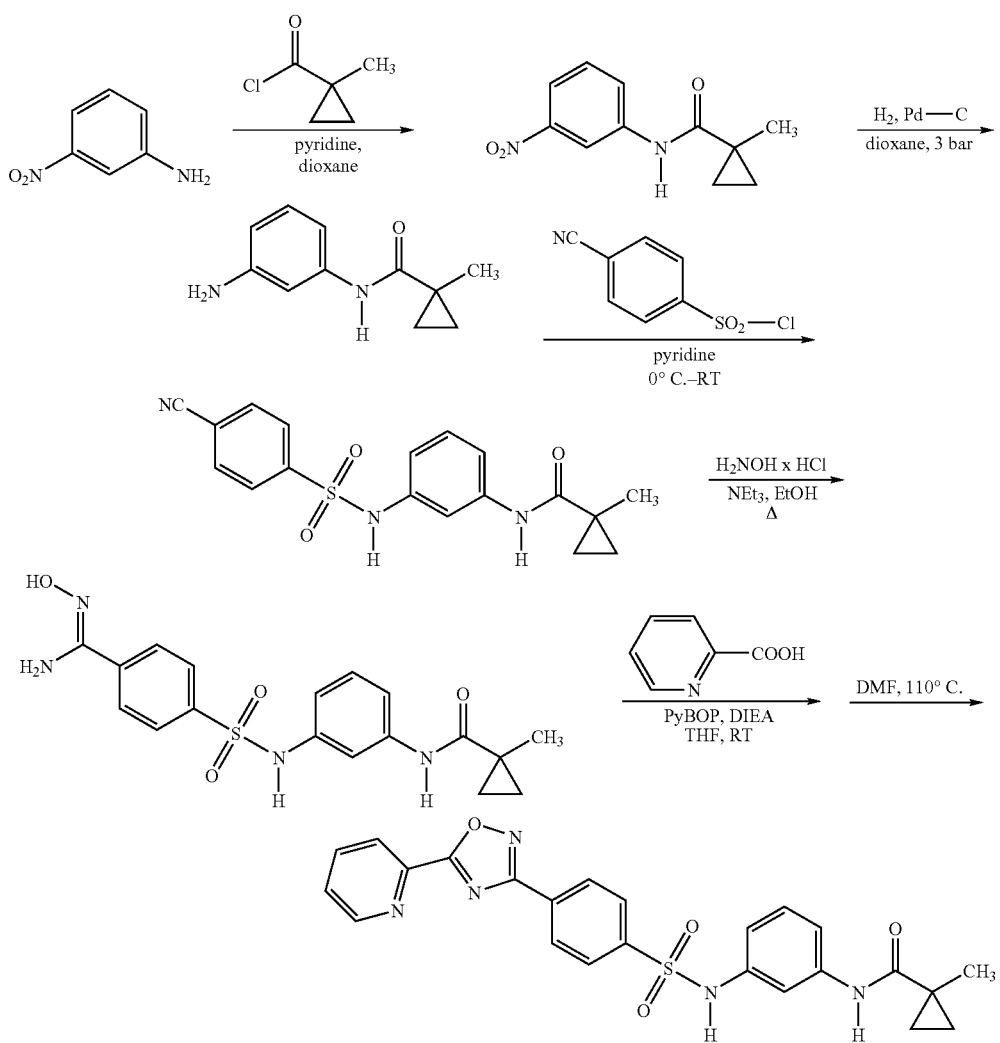

Solvents suitable for all process steps are the customary inert solvents which do not change under the reaction conditions. These preferably include organic solvents, such as ethers, for example diethyl ether, glycol monomethyl ether or glycol dimethyl ether, dioxane or tetrahydrofuran, or alcohols, such as methanol, ethanol, n-propanol, iso-propanol, n-butanol or tert-butanol, or hydrocarbons, such as benzene, toluene, xylene, cyclohexane or mineral oil fractions, or halogenated hydrocarbons, such as methylene chloride, chloroform or carbon tetrachloride, or dimethyl sulphoxide, dimethylformamide, hexamethylphosphoric triamide, ethyl acetate, pyridine, triethylamine or picoline. It is also possible to use mixtures of the solvents mentioned, if appropriate also with water. Particular preference is given to methylene chloride, tetrahydrofuran, dioxane and dioxane/water and in particular to the solvents mentioned in the section "General Procedures".

Suitable bases are organic amines, such as tri-($C_1$–$C_6$)-alkylamines, for example triethylamine, or heterocycles, such as pyridine, methylpiperidine, piperidine or N-methylmorpholine. Preference is given to triethylamine and pyridine.

The bases are generally employed in an amount of from 0.1 mol to 5 mol, preferably from 1 mol to 3 mol, in each case based on 1 mol of the compounds of the general formulae [A-1], [B-1], [C-2], [D-1] and [E-1].

The reactions can be carried out at atmospheric pressure, but also at elevated or reduced pressure (for example from 0.5 to 3 bar). In general, the reactions are carried out at atmospheric pressure.

The reactions are carried out in a temperature range of from 0° C. to 150° C., preferably from 0° C. to 30° C., and at atmospheric pressure. The conversion of the compounds [G-2] into [H-1] is carried out at elevated temperature, preferably at temperatures above 100° C.

The reductions can generally be-carried out using hydrogen in inert organic solvents, such as dimethylformamide, alcohols, ethers or acetic esters, or mixtures thereof, using catalysts such as Raney-nickel, palladium, palladium on carbon or platinum, or using hydrides or boranes, or using inorganic reducing agents, such as, for example, tin(II) chloride, in inert solvents, if appropriate in the presence of a catalyst. Preference is given to palladium on carbon.

The reaction can be carried out at atmospheric or at elevated pressure (for example from 1 to 5 bar). In general, the reaction is carried out at atmospheric pressure. Hydrogenations are preferably carried out under elevated pressure, in general at 3 bar.

The reductions are generally carried out in a temperature range of from 0° C. to +60° C., preferably at from +10° C. to +40° C.

Solvents which are suitable for the acylation are customary organic solvents which do not change under the reaction conditions. These preferably include ethers, such as diethyl ether, dioxane, tetrahydrofuran or glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethylformamide, acetonitrile or acetone. It is also possible to use mixtures of the solvents mentioned. Preference is given to dichloromethane, tetrahydrofuran and pyridine.

The acylation is carried out in the solvents listed above, at temperatures of from 0° C. to +150° C., preferably from room temperature to +100° C., and at atmospheric pressure.

The compounds of the general formulae [A-1], [A-2], [C-1], [E-1], [F-1] and [G-1] are known per se or can be prepared by methods known from the literature.

Further compounds of the general formula (I) in which A represents a 1,3,4-oxadiazole can be prepared, for example, on a polymeric support using the IRORI system according to the "Split & Mix" method, as shown below in Scheme 4:

Scheme 4:

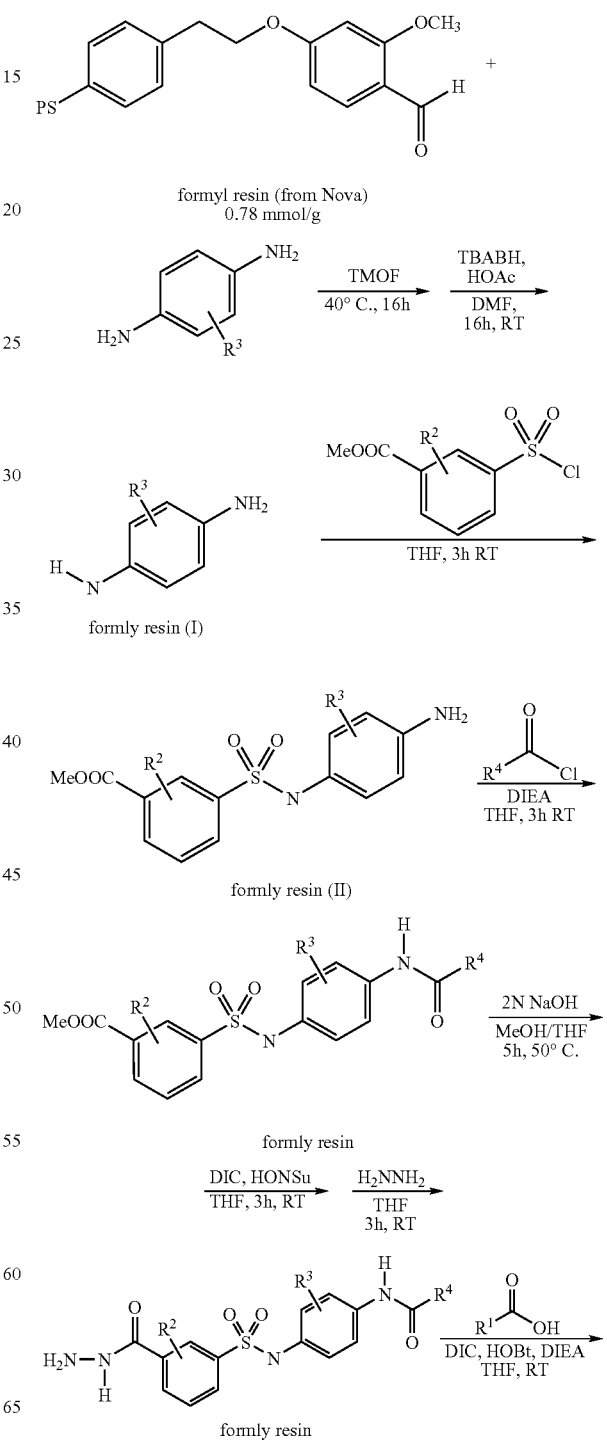

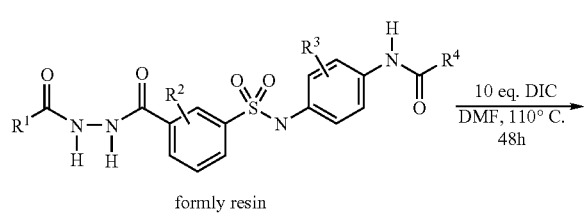
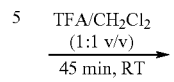
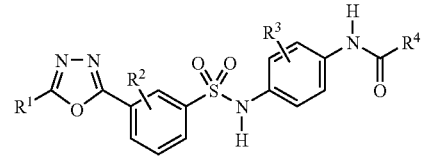
Compounds of the general formula (I) are furthermore obtained, for example, by a process according to Scheme 5 which is carried out in a mixed procedure involving solid-phase synthesis and synthesis in solution.
Scheme 5:
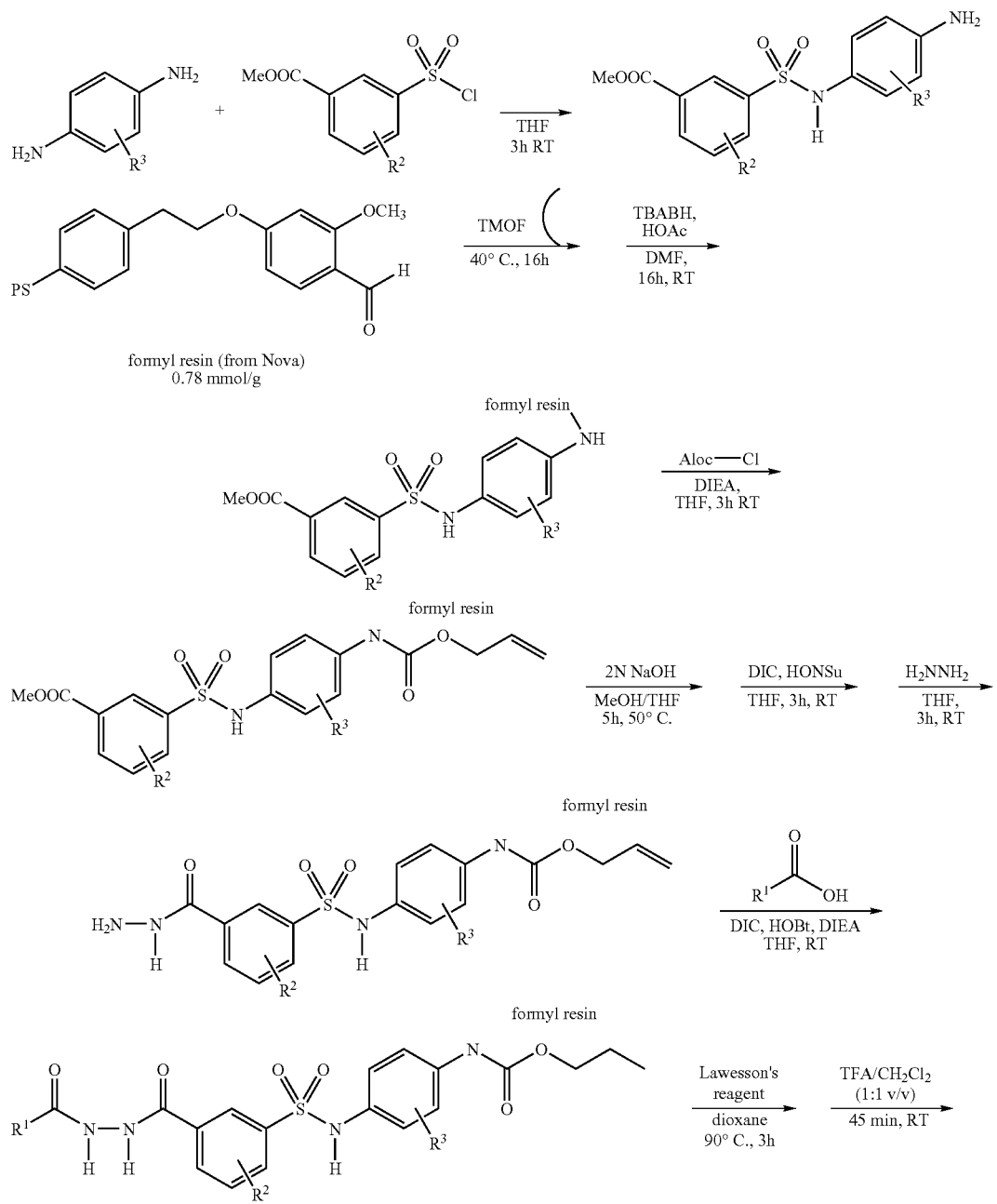

-continued

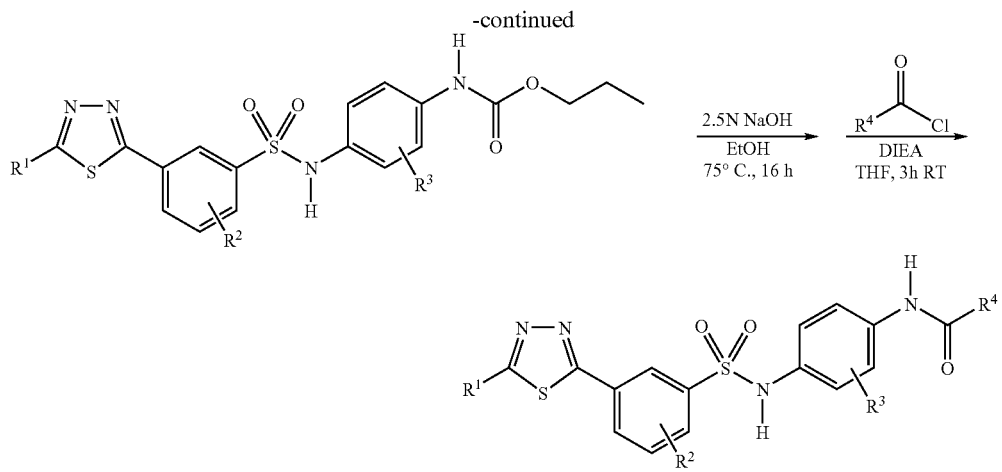

The processes shown in Schemes 4 and 5 also permit the preparation of further compounds of the general formula (I) according to the invention in which
X represents oxygen and
A represents the radical (A-II)

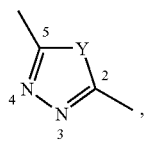
(A-II)

which is attached to the adjacent phenyl ring via one of the carbon atoms in position 2 or 5,
and in which
Y represents oxygen,
by cyclizing hydrazides of the general formula [H-2]

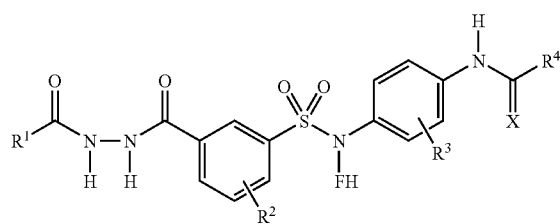
[H-2]

in which X, $R^1$, $R^2$, $R^3$, $R^4$ have one of the meanings given above, and
FH represents hydrogen, an amino protective group or a polymeric support, with elimination of water, to give the compounds of the general formula (I).

They further permit the preparation of compounds of the general formula (I) in which
X represents oxygen and
A represents the radical (A-II)

(A-II)

which is attached to the adjacent phenyl ring via one of the carbon atoms of position 2 or 5,
and in which
Y represents sulphur,
by cyclizing hydrazides of the general formula [H-3]

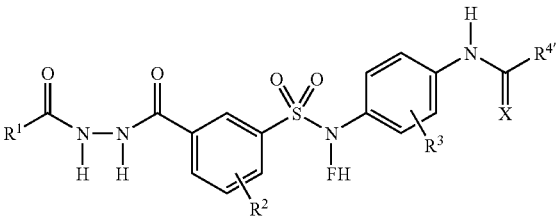
[H-3]

in which $R^1$, $R^2$, $R^3$ are as defined above,
FH represents hydrogen, an amino protective group or a polymeric support, and
$R^{4'}$ represents $(C_1-C_6)$-alkoxy, $(C_1-C_6)$-alkenoxy or aralkoxy,
in the presence of a thio donor, preferably Lawesson's reagent, to give compounds of the general formula (I) in which Y represents sulphur, then removing group —C(O)—$R^{4'}$ and finally reacting with compounds of the general formula

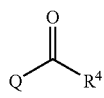

in which $R^4$ and Q are as defined above.

The compounds of the general formula (I) according to the invention show a surprising range of actions which could not have been predicted. They show an antiviral action on representatives of the group of the Herpes viridae, in particular on human cytomegalovirus (HCMV). They are thus suitable for the treatment and prophylaxis of disorders caused by Herpes viridae, in particular disorders caused by human cytomegaloviruses.

Owing to their particular properties, the compounds of the general formula (1) can be used for preparing medicaments suitable for the prophylaxis or treatment of diseases, in particular viral disorders.

Owing to their properties, the compounds according to the invention are useful active compounds for the treatment and prophylaxis of infections by human cytomegaloviruses and disorders caused by these infections. Examples of areas of indication which may be mentioned are:
1) Treatment and prophylaxis of HCMV infections in AIDS patients (retinitis, pneumonitis, gastrointestinal infections).
2) Treatment and prophylaxis of cytomegalovirus infections in bone marrow and organ transplant patients who often suffer life-threatening HCMV pneumonitis or encephalitis, or gastrointestinal or systemic HCMV infections.
3) Treatment and prophylaxis of HCMV infections in neonates and in infants.
4) Treatment of an acute HCMV infection in pregnant women.
5) Treatment of HCMV infections in immunosuppressed patients suffering from cancer and undergoing cancer therapy.

The novel active compounds can be used on their own and, if required, also in combination with other antiviral active compounds, such as, for example, gancycloyir or acylovir.

Descriptions of Biological Tests:

In Vitro Action:

Anti-HCMV (Anti-Human Cytomegalovirus) and anti-MCMV (Anti-Murine Cytomegalovirus) cytopathogenicity tests:

The test compounds were employed as 50 millimolar (mM) solutions in dimethyl sulphoxide (DMSO). Ganciclovir, foscarnet and cidofovir served as reference compounds. Following the addition of in each case 2 µl of the 50, 5, 0.5 and 0.05 mM DMSO stock solutions to in each case 98µ of cell culture medium in row 2 A-H, in duplicate determinations, 1:2 dilutions with in each case 50 µl of medium were prepared up to row 11 of the 96-well plate. The wells in rows 1 and 12 each contained 50 µl of medium. 150 µl of a suspension of $1 \times 10^4$ cells (human lung fibroblasts [HELF]) (row 1=cell control) or, in rows 2–12, a mixture of HCMV-infected and non-infected HELF cells (M.O.I.=0.001–0.002), i.e. 1–2 infected cells per 1000 non-infected cells, were then pipetted into each of the wells. Row 12 (without substance) served as virus control. The final test concentrations were 250–0.0005 µM. The plates were incubated at 37° C./5% $CO_2$ for 6 days, i.e. until all cells in the virus controls had been infected (100% cytopathogenic effect [CPE]). The wells were then fixed and stained by adding a mixture of Formalin and Giemsa Stain (30 minutes), washed with doubly distilled water and dried in a drying cabinet at 50° C. The plates were then evaluated visually using an overhead microscope (plaque multiplier from Technomara).

From the test plates, the following data were determined:
$CC_{50}$ (HELF)=substance concentration in µM at which, compared to the untreated cell control, no visible cytostatic effects on the cells were noticeable;
$EC_{50}$ (HCMV)=substance concentration in µM which inhibits the CPE (cytopathic effect) by 50% compared to the untreated virus control;
SI (selectivity index)=$CC_{50}$ (HELF)/EC50 (HCMV).

Compared to the process described above for HCMV, the anti-MCMV test was carried out with the following changes: a cell-free virus suspension was mixed with a concentrated cell suspension (3T3 mouse cells) and incubated for 15 minutes for adsorption of the viruses, and the suspension was then diluted with medium to $1.3 \times 10^5$ cells/ml with a final multiplicity of infection (M.O.I.) of from 0.05–0.1, and in each case 150 µl were dispensed into the wells. The incubation time was 5 days.

Representative activity data for the compounds according to the invention are given in Table 1:

TABLE 1

| Example No. | HELF $CC_{50}$ [µM] | HCMV $EC_{50}$ [µM] | SI HCMV | 3T3 $CC_{50}$ [µM] | MCMV $EC_{50}$ [µM] | SI MCMV |
|---|---|---|---|---|---|---|
| 1 | 110 | 0.055 | 2000 | 33 | 0.019 | 1737 |
| 2 | <16 | 0.05 | <320 | 0.9 | 0.045 | 20 |
| 3 | <140 | 0.018 | <7778 | 23 | 0.008 | 2875 |
| 4 | >63 | 0.01 | >6300 | 11 | 0.015 | 733 |
| 5 | >16 | 0.016 | >1000 | >31 | 0.014 | >2214 |
| 6 | 39 | 0.02 | 2053 | 2.9 | 0.041 | 71 |
| 7 | 47 | 0.025 | 1880 | 12 | 0.025 | 480 |
| 8 | >2.2 | 0.02 | >110 | >3.9 | 0.024 | >163 |
| 9 | 39 | 0.018 | 2167 | 4 | 0.068 | 59 |
| 10 | >3.9 | 0.008 | >488 | >7.8 | 0.007 | >975 |
| 11 | >16 | 0.015 | >1040 | >12 | 0.002 | >5850 |
| 12 | 14 | 0.058 | 241 | 7 | 0.058 | 121 |
| 13 | <8 | 0.04 | <200 | <16 | 0.03 | <533 |
| 131 | >28 | 0.02 | >1555 | | | |
| 132 | 47 | 0.006 | 7833 | 2.3 | 0.003 | 767 |
| 134 | 94 | 0.009 | 10444 | 8 | 0.0047 | 1617 |
| 135 | 47 | 0.0052 | 9039 | 3 | 0.011 | 273 |

In Vivo Action:

MCMV Lethality Test:

Animals:

2–3-week old female immunocompetent mice (12–14 g), strain Balb/C AnN or CD1, were purchased from commercial breeders (Bomholtgaard, Iffa, Credo). The animals were not kept under sterile conditions.

Virus Cultivation:

Murine cytomegalovirus (MCMV), Smith strain, was passaged repeatedly in vivo in female CD1 mice. 21 days after intraperitoneal infection ($2 \times 10^4$ plaque forming units/ 0.2 ml/mouse), the salivary glands were removed, taken up in three times the volume of Minimal Essential Medium (MEM)+10% foetal calf serum (FCS) and homogenized using an Ultraturrax. 10% DMSO v/v were added, 1 ml aliquots were prepared and the virus suspension was stored at −140° C. Following serial dilution of the salivary gland isolate in steps of ten, the titre was determined in cell culture for NIH 3T3 cells after staining with Giemsa stain, and the lethal dose was determined in vivo in 2–3 week old Balb/C mice.

Virus Infection of the Test Animals Treatment and Evaluation:

2–3 week old female immunocompetent Balb/C mice (12–14 g) were infected intraperitoneally with $3 \times 1$ PFU/0.2 ml/mouse. Starting 6 hours after the infection, the mice were treated orally with substance twice a day (8.00 and 16.00 hours) for a period of 5 days. The dose was 3, 10, 30 or 90 mg/kg of body weight, and the volume administered was 10 ml/kg of body weight. The substances were formulated in the form of a 0.5% strength Tylose suspension, with 2% of DMSO. The placebo-treated control animals die within a period of 4–8 days after the infections. Evaluation was carried out by determining the percentage of surviving animals following treatment with substance, compared to the placebo-treated control group.

HCMV Xenograft Gelfoam® Model:

Animals:

3–4-week old female immunodeficient mice (16–18 g), Fox Chase SCID or Fox Chase SCID-NOD, were purchased from commercial breeders (Bomholtgaard, Jackson). The animals were kept under sterile conditions (including bedding and feed) in isolators.

Virus Cultivation:

Human cytomegalovirus (HCMV) Davis Smith strain, was cultivated in vitro on human embryonal foreskin fibroblasts (NHDF cells). The virus-infected cells were harvested 5–7 days after infection of the NHDF cells with a multiplicity of infection (M.O.I) of 0.01 and stored in the presence of Minimal Essential Medium (MEM), 10% foetal calf serum (FCS) with 10% DMSO, at −140° C. Following serial dilution of the virus-infected cells in steps of ten, the titre was determined on 24-well plates of confluent NHDF cells, after vital staining with Neutral Red.

Preparation of the Sponges, Transplantation, Treatment and Evaluation:

Collagen sponges (dimensions 1×1×1 cm, Gelfoam®; from Peasel & Lorey, order No. 407534; K. T. Chong et al., Abstracts of 39$^{th}$ Interscience Conference on Anti-microbial Agents and Chemotherapy, 1999, p. 439) are initially wetted with phosphate-buffered saline (PBS) and the enclosed air bubbles are removed by degassing, and the sponges are then stored in MEM+10% FCS. 3 hours after the infection, 1×10$^6$ virus-infected NHDF cells (infection with HCMV-Davis M.O.I=0.01) are detached and, in 20 μl MEM, 10% FCS, added dropwise to a moist sponge. 12–13 hours later, the infected sponges are incubated with 5 ng/μl of basic Fibroblast Growth Factor (bFGF) in 25 μl of PBS/0.1% BSA/1 mM DTT. For transplantation, the immunodeficient mice are anesthetized with Avertin, the fur on the back is removed using an electric shaver, the epidermis is opened 1–2 cm and relieved and the moist sponges are transplanted under the skin of the back. The wound caused by the surgery is closed using tissue glue. 24 hours after the transplantation, the mice were treated orally with substance twice daily (8.00 and 16.00 hours) over a period of 8 days. The dose was 10 or 30 mg/kg of body weight, the administration volume was 10 ml/kg of body weight. The substances were formulated in the form of a 0.5% strength Tylose suspension with 2% of DMSO. 10 days after the transplantation and 16 hours after the last administration of substance, the animals were painlessly sacrificed and the sponge was removed. The virus-infected cells were released from the sponge by digestion with collagenase (330 U/1.5 ml) and stored in the presence of MEM, 10% foetal calf serum, 10% DMSO at −140° C. Following serial dilution of the virus-infected cells in steps of ten, evaluation was carried out by titre determination on 24-well plates of confluent NHDF cells, after vital staining with Neutral Red. What was determined was the number of infectious virus particles after treatment with substance, compared to the placebo-treated control group.

The test described below is used to examine the substances according to the invention for potential side-effects with respect to an induction of cytochrome P450 enzymes.

Examination of the Induction of Cytochrome P450 Enzymes in Human Liver Cell Cultures:

At a cell density of 2.5×10$^5$ cells, primary human hepatocytes were cultivated between two layers of collagen in 24-well microtitre plates, at 37° C. and 5% $CO_2$, for 8 days. The cell culture medium was changed daily.

After 48 hours in culture, the hepatocytes were treated for 5 days with different concentrations of the test substances, compared to the inductors rifampicin (50 μM) and phenobarbital (2 mM), each test being carried out twice. The final concentrations of the test substances were 0.1–10 μg/ml.

Using the cell cultures, the inductive effect of the test substances on the cytochrome (CYP) P450 enzymes 1A2, 2B6, 2C19 and 3A4 was determined on day 8 by addition of the substrates 7-ethoxyresorufin (CYP1A2), [$^{14}$C]S-mephenytoin (CYP2B6 and 2C19) and [$^{14}$C]testosterone (CYP3A4). The inductive potential of the test substances was determined using the measured enzyme activities CYP1A2, 2B6, 2C19 and 3A4 of treated cells compared to untreated cells.

The novel active compounds can be converted in a known manner into the customary formulations, such as tablets including coated tablets, pills, granules, aerosols, syrups, emulsions, suspensions and solutions, using inert, non-toxic, pharmaceutically suitable excipients or solvents. In this case, the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifying agents and/or dispersing agents, it being possible, for example if the diluent used is water, to use organic solvents as auxiliary solvents, if appropriate.

Administrations carried out in a customary manner, preferably orally, parenterally or topically, in particular perlingually or intravenously.

In the case of parenteral administration, solutions of the active compounds using suitable liquid carrier materials can be employed.

In general, it has been found to be advantageous in the case of intravenous administration to administer amounts of from about 0.001 to 10 mg/kg, preferably from about 0.01 to 5 mg/kg, of body weight to achieve effective results, and in the case of oral administration the dose is about 0.01 to 25 mg/kg, preferably from 0.1 to 10 mg/kg, of body weight.

In spite of this, it may be necessary, if appropriate, to depart from the amounts mentioned, namely depending on the body weight or on the type of administration route, on the individual response towards the medicament, the manner of its formulation and the time or interval at which administration takes place. Thus, in some cases it may be adequate to manage with less than the above-mentioned minimum amount, while in other cases the upper limit mentioned must be exceeded. In the case of the administration of relatively large amounts, it may be advisable to divide these into several individual administrations over the course of the day.

Abbreviations:
Aloc-Cl allyl chloroformate
DCM dichloromethane
DIC N,N'-diisopropylcarbodiimide
DIEA diisopropylethylamine DMF dimethylformamide
eq. equivalent(s)
sat. saturated
HOAc acetic acid
HOBt hydroxybenzotriazole
HONSu N-hydroxysuccinimide
MTP microtitre plate
PS- polystyrene-resin-
PyBOP benzotriazolyl-N-oxi-tris(dimethylamino)phosphonium hexafluorophosphate
Rt retention time
RT room temperature
TBABH tetrabutylammonium borohydride
TFA trifluoroacetic acid
THF tetrahydrofuran
TMOF trimethyl orthoformate General Procedure for the Reaction of Compounds of the Formula [A-1] with Compounds of the Formula [A-2] (GP 1):

1.0 eq. of [A-1] are dissolved in dioxane (0.2 M solution), 2.5 eq. of pyridine are added, the solution is cooled to 5° C. and 1.1 eq. of [A-2], in which Q is preferably chlorine, are added dropwise as a 1.0 M solution. The mixture is stirred at 5° C. for another 30 min and cooling is then removed, and the mixture is stirred at room temperature for 16 h. The mixture is poured into $H_2O$ and the precipitated product is filtered off with suction, washed with $H_2O$ and dried under high vacuum.

General Procedure for the Hydrogenation of Compounds of the Formula [A-3] (GP 2):

0.14 mol of the compounds [A-3] is dissolved in 500 ml of DMF or ethanol and, under argon, a suspension of 6.0 g of 10% of Pd—C is added. The mixture is then hydrogenated at a hydrogen pressure of 3 bar. After the reaction has gone to completion (monitored by TLC or HPLC), the Pd—C catalyst is filtered off and the solvent is removed under reduced pressure. The crude products of the general formula [B-1] are reacted further without further purification.

General Procedure for the Sulphonylation of the Compounds of the General Formula [B-1] (GP 3):

Under argon, 1.0 eq. of the compounds [B-1] is dissolved in dioxane (0.2 M solution), and 2.5 eq. of pyridine are added. The mixture is stirred at room temperature for 30 min, and 1.1 eq. of the compounds of the general formula [C-1], in which Z is preferably chlorine, dissolved in dioxane (1.0 M solution) are then added and the mixture is stirred at room temperature for 16 h. The solution is then poured into $H_2O$ and extracted 3 times with DCM. The organic phase is washed with sat. $NaHCO_3$ solution, dried over $Na_2SO_4$ and filtered, and the solvent is removed under reduced pressure. The residue [C-2] is dried under high vacuum and then reacted further without further purification.

General Procedure for the Synthesis of Compounds of the General Formula [D-1] from Compounds of the General Formula [C-2] (GP 4):

The compounds of the formula [C-2] (1.0 eq.) are dissolved in ethanol (0.1 M solution), hydroxylamine hydrochloride (1.5 eq.) and triethylamine (1.6 eq.) are added to the solution and the solution is then heated under reflux for 4 h and stirred at room temperature for another 16 h. The solvent is removed under reduced pressure, the residue is taken up in ethyl acetate and extracted 3× with water, the organic phase is dried over $MgSO_4$ and filtered and the solvent is removed under reduced pressure. The residue [D-1] is dried under high vacuum.

General Procedure for the Reaction of the Compounds of the General Formula [D-1] with Compounds [E-1] (GP 5):

1.0 eq. of the compounds of the general formula [D-1], 1.05 eq. of carboxylic acid [E-1] and 1.1 eq. of PyBOP are initially charged in THF (0.1 M solution), 1.1 eq. of N,N-diisopropylethylamine are added to the suspension and the resulting solution is stirred at room temperature for 16 h. The mixture is then diluted with 10 ml of DCM and extracted in each case once with 1 N HCl, sat. $NaHCO_3$ solution and sat. NaCl solution. The organic phase is dried over $Na_2SO_4$ and filtered and the solvent is removed under reduced pressure. The crude product is directly reacted further.

General Procedure for the Synthesis of a 1,2,4-Oxadiazole from the Crude Product Obtained According to GP 5 (GP 6):

1.0 mmol of crude product, obtained according to GP 5, is taken up in 10 ml of DMF, and the solution is heated at 110° C. Once the reaction has gone to completion (monitored by TLC or HPLC, about 2–16 h), the mixture is diluted with DCM and extracted twice with $H_2O$. The combined aqueous phases are extracted twice with DCM, the organic phases are combined, dried over $Na_2SO_4$ and filtered and the solvent is removed under reduced pressure. The resulting compounds of the general formula (I) are purified by silica gel chromatography (cyclohexane/ethyl acetate) or by preparative HPLC.

General Procedures for Syntheses Using Polymeric Supports:

General Procedure for the Synthesis of 1,3,4-Oxadiazoles According to Scheme 4:

The reactions according to Scheme 4 were carried out on a polymeric support using the IRORI system according to the "Split & Mix" method, known to the solid-phase chemist, employing 4 carbonyl chlorides, 24 carboxylic acids and the two meta- or para-isomers of the phenylenediamine or sulphonyl chloride. Here, the first two steps were carried out in a flask, the other steps in IRORI MiniKans (100 mg of resin per can).

Synthesis of the Starting Resins (I) and (II) for the Syntheses on the Polymeric Support According to Scheme 4:

Reductive Amination of Formyl Resin (from Nova Biochem, 0.78 mmol/g):

The formyl resin (1.0 eq.) is, in a flask, suspended in TMOF/DMF (100 ml per 12.5 g of resin), and the diamine (6.0 eq.) is added. The suspension is shaken at 40° C. for 16 h, and a freshly prepared solution of TBABH (4.0 eq.) and HOAc (16.0 eq.) in DMF is then added. After 8 h at RT, the solvent is filtered off, and once more, reduction solution is added to the resin. After a further 16 h at RT, the solvent is filtered off with suction and the resin (I) is washed in each case 2× with in each case 200 ml of 50% strength HOAc, DMT, THF and DCM and dried under high vacuum.

Sulphonylation of Polymer-Bound Phenylenediamine:

The resin (I) (1.0 eq.) is taken up in THF, and the sulphonyl chloride (1.5 eq.) is added. The suspension is shaken at RT for 16 h, and the solvent is filtered off with suction. The resin (H) is then washed in each case 2× with in each case 100 ml of 50% strength HOAc, DMF, THF and DCM and dried under high vacuum.

Preparation of the Resin for the IRORI System:

The resins of type II are distributed as a suspension (per 3.0 g of resin: 30 ml of DMF/DCM 2:1 v/v) into each case 96 MiniKans (1 ml suspension per Kan) and washed in each case three times with DCM, and the Kans are dried under reduced pressure.

Reaction Sequence (IRORI):

Acylation with Acid Chlorides:

The Kans are sorted and taken up in THF, 5.0 eq. of DIEA and 5.0 eq. of acid chloride are added and the Kans are evacuated briefly and shaken at RT for 3 h. The reaction solutions are then separated off and the Kans are combined and washed (in each case 2×50% strength HOAc, DMF, THF, DCM).

Hydrazide Synthesis:

The combined Kans are taken up in a mixture of 2 N NaOH/MeOH/THF (5:7:15 v/v), evacuated briefly and stirred at 50° C. for 5 h. The Kans are then washed (in each case 2×50% strength HOAc, DMF, THF, DCM) and dried under reduced pressure.

The Kans are then taken up in THF, 5 eq. of DIC and 10 eq. of HONSu are added and the Kans are shaken at RT for 3 h. The Kans are filtered off, washed 2× with THF and then once more taken up in THF, and 3 eq. of hydrazine hydrate are added. After a further 3 h at RT, the Kans are filtered off with suction and washed in each case 2× with 50% strength HOAc, DMF, THF and DCM.

Acylation with Carboxylic Acids/DIC/HOBt:

3 eq. of DIC, 6 eq. of DIEA and 6 eq. of HOBt are added to the carboxylic acids (3 eq.) in THF. After 60 min of activation at RT, the solution is added to the Kans, which have been sorted beforehand, and is shaken at RT for 16 h. The Kans are then combined, washed (in each case 2× with 50% strength HOAc, DoF, THF, DCM) and dried under reduced pressure.

Cyclization to the 1,3,4-oxadiazole:

The combined Kans are taken up in DMF, DCI (10 eq.) is added and the Kans are evacuated briefly and stirred at 110° C. for 48 h. The Kans are then washed (in each case 2× with 50% strength HOAc, DMF, THF, DCM) and dried under reduced pressure.

Cleavage from the Polymeric Support:

After sorting into IRORI cleavage blocks, the Kans are cut open, the resin is distributed into FlexChem blocks and the products are cleaved in a Deep-Well MTP using in each case 1.0 ml of TFA/DCM (1:1 v/v) at RT for 45 min. The resin is washed with DCM and the solvent is evaporated.

General Procedure for the Synthesis of the 1,3,4-thiadiazoles According to Scheme 5:

The synthesis is carried out by a mixed approach of solid-phase synthesis and synthesis in solution.

Synthesis of the Monosulphonylated Phenylenediamine:

The phenylenediamine (1.0 eq.) is dissolved in TBF (0.4 M solution), 1.0 eq. of sulphonyl chloride are added and the mixture is stirred at RT for 16 h. The mixture is then diluted with DCM and extracted 2× with water, the aqueous phases are reextracted 1× with DCM and the org. phases are combined, dried over $Na_2SO_4$ and concentrated using a rotary evaporator. The crude product is reacted further without further purification.

Attachment to the Polymeric Support and Synthesis of the Thiadiazole:

Reductive Amination of Formyl Resin (from Nova Biochem, 0.78 mmol./g):

The formyl resin (1.0 eq.) is, in a flask, suspended in TMOF/DMF (100 ml per 12.5 g of resin), and the sulphonylated phenylenediamine (6.0 eq.) is added. The suspension is shaken at 40° C. for 16 h, and a freshly prepared solution of TBABH (4.0 eq.) and HOAc (16.0 eq.) in DMF is then added. After 8 h at RT, the solvent is filtered off, and once more, reduction solution is added to the resin. After a further 16 h at RT, the solvent is filtered off with suction and the resin is washed in each case 2× with in each case 200 ml of 50% strength HOAc, DMF, THF and DCM and dried under high vacuum.

Acylation of the Resin:

In a syringe with PE fritt (from MultiSyntech), the resin is suspended in THF, and 3.0 eq. of DIEA and 3.0 eq. of carbonyl chloride are added. The suspension is shaken at RT for 3 h and then filtered off with suction, and the resin is washed in each case 2× with 50% strength HOAc, DMF, THF and DCM.

Hydrazide Synthesis:

In a syringe with PE fritt (from MultiSyntech), the resin is taken up in a mixture of 2 N NaOH/MeOH/THF (5:7:15 v/v), stirred at 50° C. for 5 h and then washed (in each case 2× with 50% strength HOAc, DMF, THF, DCM). The resin is then taken up in THF, 5 eq. of DIC and 10 eq. of HONSu are added and the mixture is shaken at RT for 3 h. The resin is filtered off, washed 2× with THF and then once more taken up in THF, and 3 eq. of hydrazine hydrate are added. After a further 3 h at RT, the resin is filtered off with suction and washed (in each case 2× with 50% strength HOAc, DMF, THF, DCM).

Acylation of the Hydrazide with Carboxylic Acids/DIC/HOBt:

3 eq. of DIC, 6 eq. of DIEA and 6 eq. of HOBt are added to the carboxylic acid (3 eq.) in THF. After 6 min of activation at room temperature, the solution is added to the resin (1 ml per 100 mg of resin), and the mixture is shaken at RT for 16 h. The resin is then filtered off with suction and washed (in each case 2× with 50% strength HOAc, DMF, THF, DCM). The LC-MS of the cleaved sample shows that the double bond of the allyloxycarbonyl group is hydrogenated in this reaction.

Thiadiazole Synthesis:

The resin is initially charged in dioxane (1 ml per 100 mg of resin), 5.0 eq. of Lawesson's reagent are added and the mixture is stirred at 90° C. for 3 h. The resin is then filtered off with suction and washed in each case 2× with DMF, 50% strength HOAc, DMF, THF and DCM.

Cleavage from the Polymeric Support, Removal of the Carbonate Protective Group and Synthesis of the Amide:

The resin is treated with TFA/DCM (1:1 v/v, 1 ml per 100 mg of resin) and, after 45 min, filtered off and washed with DCM (same volume). TFA and DCM are removed under reduced pressure and the residue is taken up in ethanol/2.5 N NaOH (1:1 v/v, 0.5 M solution), stirred at 75° C. for 16 h, diluted with DCM and extracted 2× with water, the aqueous phase is adjusted to pH 7 using 1 N HCl and extracted 3× with DCM, all org. phases are combined, washed 2× with water, dried over $Na_2SO_4$ and concentrated using a rotary evaporator. The residue is taken up in THF, 1.05 eq. of DEA and 1.05 eq. of acid chloride are added and the mixture is shaken at RT for 16 h. Volatile components are then removed under reduced pressure and the product is isolated by preparative HPLC.

Starting Materials:

EXAMPLE I

1-Methyl-N-(3-nitrophenyl)-cyclopropanamide

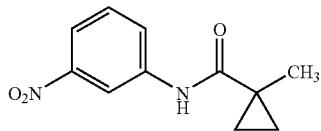

This compound is prepared according to GP 1 from 80.0 g of 3-nitroaniline.
Yield: 107 g (81% of theory)

EXAMPLE II

3-Fluor-2,2-dimethyl-N-(3-aminophenyl)-propanamide

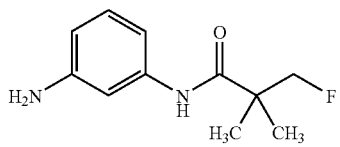

This compound is prepared according to GP 1 and GP 2 from 3-nitroaniline, without purification of the intermediate.
Yield: 85% of theory (over 2 steps)

EXAMPLE III

1-Methyl-N-(3-aminophenyl)-cyclopropanamide

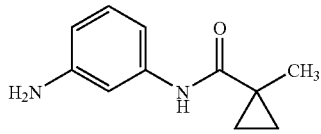

This compound is prepared according to GP 2 from 107 g of the compound from Example 1.
Yield: 80 g (87% of theory)

EXAMPLE IV

3-Fluoro-2,2-dimethyl-N-(3-{[(4-methylphenyl)sulphonyl]amino}phenyl)-propanamide

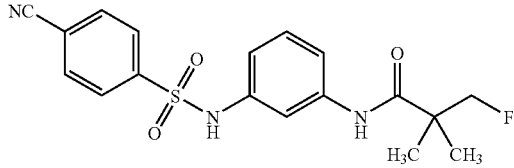

This compound is prepared according to GP 3 from 18.68 g of the compound from Example II.
Yield: 19.96 g (78% of theory)

EXAMPLE V

N-{3-[({4-[Amino(hydroxyimino)methyl]phenyl}sulphonyl)amino]phenyl}-3-fluoro-2,2-dimethylpropanamide

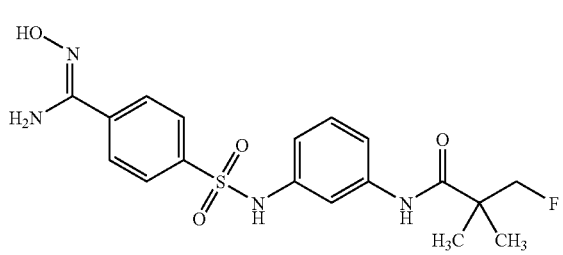

This compound is prepared according to GP 4 from 10.0 g of the compound from Example IV.
Yield: 10.5 g (97% of theory)

EXAMPLE VI

N-(3-{[(4-Cyanophenyl)sulphonyl]amino}phenyl)-1-methylcyclopropanecarboxamide

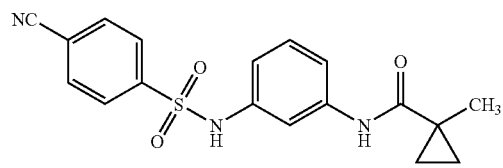

This compound is prepared according to GP 3 from 90 g of the compound from Example III.
Yield: 150 g of crude product (quant.) HPLC: Rt=2.87 min (HPLC method/instrument 9)

EXAMPLE VII

N-{3-[({4-[Amino(hydroxyimino)methyl]phenyl}sulphonyl)amino]phenyl}-1-methyl-cyclopropanecarboxamide

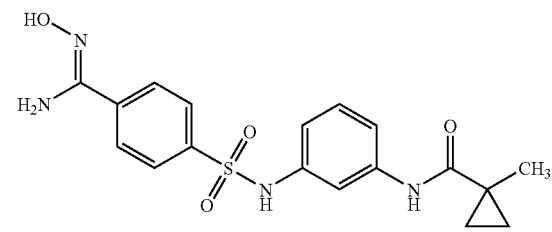

This compound is prepared according to GP 3 from 168 g of the compound from Example VI (as crude product).
Yield: 118 g (57% of theory) HPLC: Rt=2.7 min (HPLC method/instrument 5) MW 388.45; m/z found: 389.

EXAMPLE VIII

2-Aminoacetyl-picoline

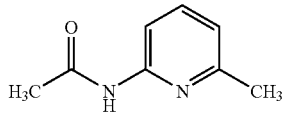

25.0 g (0.23 mol) of 6-aminopicoline are dissolved in 250 ml of acetic acid, and 47.2 g (0.46 mol) of acetic anhydride are added with stirring and ice-cooling. Initially, the mixture is stirred with ice-cooling for another 30 min, and the ice bath is then removed and stirring is continued at room temperature for 16 h. The clear solution is then concentrated under reduced pressure. The oily residue is crystallized in an ice bath and the crystals are dried under reduced pressure.

Yield: 28 g (80.6% of theory) $^1$H-NMR (200 MHz, DMSO-$d_6$): δ=10.41 (s, 1H), 7.87 (d, 1H), 7.63 (t, 1H), 6.93 (d, 1H), 2.39 (s, 3H), 2.06 (s, 3H).

EXAMPLE IX

2-Aminoacetyl-picolinic acid

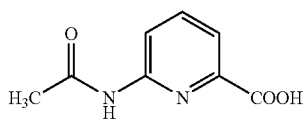

31.0 g (0.21 mol) of 2-aminoacetylpicoline are dissolved in 310 ml of water and heated at 75° C., and 60.0 g (0.38 mol) of potassium permanganate are added a little a time over a period of 3 h such that the violet colour disappears again in each case. The mixture is stirred at 75° C. for another 5 h, and the hot reaction mixture is then filtered. The aqueous phase is extracted four times with dichloromethane and then acidified to pH 4 using 1 N hydrochloric acid. The precipitate is filtered off, washed with 0.1 N hydrochloric acid and dried under reduced pressure.

Yield: 15.5 g (42% of theory) HPLC: Rt=1.11 min (HPLC method/instrument 3) MW 180.16; m/z found: 181 $^1$H-NMR (200 MHz, DMSO-$d_6$): δ=13.23 (br s, 1H), 10.81 (s, 1H), 8.28 (d, 1H), 7.94 (t, 1H), 7.73 (dd, 1H), 2.12 (s, 3H).

WORKING EXAMPLES

The 1,2,4-oxadiazoles attached in the 3-position shown in the working examples below were prepared from compounds of type Example V according to GP 5 and GP 6.

Example 1

3-Fluoro-2,2-dimethyl-N-{3-[({4-[5-(2-pyridinyl)-1,2,4-oxadiazol-3-yl]phenyl}-sulphonyl)amino]phenyl}propanamide

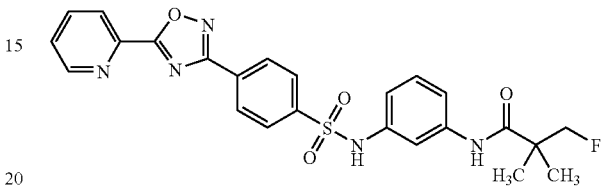

5.93 g (45.92 mmol) of N,N-diisopropylethylamine, 5.65 g (45.92 mmol) of picolinic acid and 23.89 g (45.92 mmol) of PyBOP are initially charged in 70 ml of THF, the mixture is stirred at room temperature for 30 min, 17.05 g (41.74 mmol) of amidoxime from Example V are then added and the solution is stirred at room temperature for 16 h. The reaction mixture is concentrated under reduced pressure, the residue is taken up in 50 ml of DMF and the solution is stirred at 110° C. for 4 h. The mixture is then diluted with 300 ml of DCM, and the organic phase is extracted three times with in each case 200 ml of 2 N $H_2SO_4$ and once with sat. $NaHCO_3$ solution. The organic phase is dried over $Na_2SO_4$ and filtered, and the solvent is removed under reduced pressure (43.5 g of crude product). The product is purified by silica gel chromatography using cyclohexane/ethyl acetate (6:4 v/v) and, after purification, stirred with cyclohexane, and the solid is filtered off with suction and dried under reduced pressure.

Yield: 12.59 g (61% of theory) of a white solid m.p.: 178.9° C. MW 495.53; m/z found: 496 HPLC Rt: 4.38 min. (LC method/instrument 3) $^1$H-NMR (300 MHz, DMSO): δ=1.20 (s, 3 H), 1.21 (s, 3 H), 4.48 (d, 2 H), 6.81 (d, 1 H), 7.14 (t, 1 H), 7.31 (d, 1 H), 7.58 (s, 1 H), 7.71–7.78 (m, 1 H), 7.99 (d, 2 H), 8.09–8.18 (m, 1 H), 8.27 (d, 2 H), 8.34 (d, 1 H), 8.86 (d, 1 H), 9.35 (s, 1 H), 10.43 (s, 1 H).

Example 2

N-(3-{[(4-{5-[3-(Dimethylamino)phenyl]-1,2,4-oxadiazol-3-yl}phenyl)sulphonyl]-amino}phenyl)-1-methylcyclopropanecarboxamide

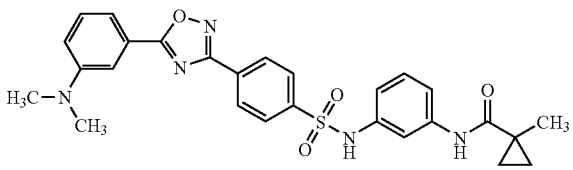

MW 517.61; m/z found: 518 HPLC Rt: 3.25 min. (HPLC method/instrument: 3) $^1$H-NMR (300 MHz, DMSO): δ=0.54–0.64 (m, 2 H), 1.00–1.09 (m, 2 H), 1.36 (s, 3 H), 3.00 (s, 6 H), 6.79 (d, 1 H), 7.02–7.50 (m, 6 H), 7.57 (t, 1 H), 7.97 (d, 2 H), 8.24 (d, 2 H), 9.15 (s, 1 H), 10.34 (s, 1 H).

Example 3

1-Methyl-N-{3-[({4-[5-(2-pyridinyl)-1,2,4-oxadiazol-3-yl]phenyl}sulphonyl)-amino]phenyl}cyclopropanecarboxamide

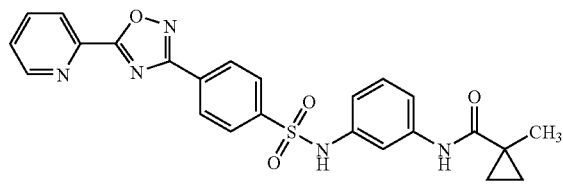

20.0 g (51.59 mmol) of the appropriate amidoxime, 6.66 g (54.06 mmol) of picolinic acid and 29.47 g (56.66 mmol) of PyBOP are initially charged in 60 ml of THF, 7.32 g (56.66 mmol) of N,N-diisopropylethylamine are added at room temperature to the suspension and the resulting clear solution is stirred at room temperature for 16 h. The mixture is then diluted with 250 ml of DCM and extracted in each case once with in each case 250 ml of 1 N HCl, sat. NaHCO$_3$ solution and sat. NaCl solution. The organic phase is dried over Na$_2$SO$_4$ and filtered, and the solvent is removed under reduced pressure. The crude product (25.41 g) is taken up in 250 ml of DMF, and the solution is stirred at 110° C. for 2.5 h. The mixture is then diluted with 250 ml of DCM, and the organic phase is extracted twice with in each case 250 ml of H$_2$O. The combined aqueous phases are extracted twice with in each case 250 ml of DCM, the organic phases are combined, dried over Na$_2$SO$_4$ and filtered and the solvent is removed under reduced pressure (43.5 g of crude product). The product is purified by chromatography on silica gel 60 using cyclohexane/ethyl acetate 1:1 v/v.

Yield: 18.35 g (75% of theory) of a white solid m.p.: 202° C. MW 475.53; m/z found: 476 HPLC Rt: 4.0 min. (HPLC method/instrument: 6) $^1$H-NMR (200 Mz, DMSO): δ=0.55–0.64 (m, 2 H), 1.00–1.10 (m, 2 H), 1.36 (s, 3 H), 6.78 (d, 1 H), 7.11 (t, 1 H), 7.27 (d, 1 H), 7.57 (s, 1 H), 7.70–7.79 (m, 1 H), 8.08 (d, 2 H), 8.09–8.19 (m, 1 H), 8.26 (d, 2 H), 8.34 (d, 1 H), 8.87 (d, 1 H), 9.17 (s, 1 H), 10.38 (s, 1 H).

Example 4

N-{3-[({4-[5-(2-Amino-1,3-thiazol-4-yl)-1,2,4-oxadiazol-3-yl])phenyl}sulphonyl)-amino]phenyl}-1-methylcyclopropanecarboxamide

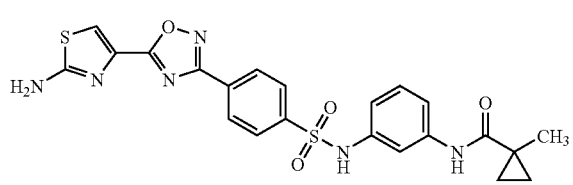

MW 496.57; m/z found: 497 HPLC Rt: 2.508 min. (HPLC method/instrument: 8) $^1$H-NMR (200 MHz, DMSO): δ=0.54–0.64 (m, 2 H), 1.00–1.09 (m, 2 H), 1.36 (s, 3 H), 6.78 (d, 1 H), 7.12 (t, 1 H), 7.28 (d, 1 H), 7.52 (s, 1 H), 7.57 (s, 1 H), 7.82 (s, 1 H), 7.95 (d, 2 H), 8.19 (d, 2 H), 9.18 (s, 1 H), 10.38 (s, 1 H).

Example 5

1-Methyl-N-{3-[({4-[5-(6-methyl-2-pyridinyl)-1,2,4-oxadiazol-3-yl]phenyl}-sulphonyl)amino]phenyl}cyclopropanecarboxamide

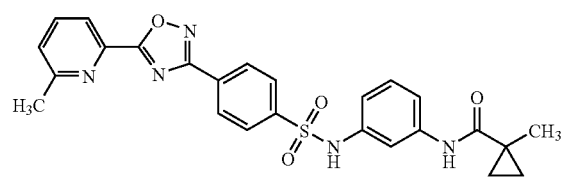

MW 489.55; m/z found: 490 HPLC Rt: 4.76 min. (HPLC method/instrument: 6) $^1$H-NMR (200 MHz, DMSO): δ=0.54–0.63 (m, 2 H), 1.00–1.09 (m, 2 H), 1.36 (s, 3 H), 2.61 (s, 3 H), 6.77 (d, 1 H), 7.10 (t, 1 H), 7.26 (d, 1 H), 7.50–7.65 (m, 2 H), 7.92–8.06 (m, 3 H), 8.14 (d, 1 H), 8.25 (d, 2 H), 9.17 (s, 1 H), 10.39 (s, 1 H).

Example 6

1-Methyl-N-{3-[({4-[5-(3-methyl-1H-pyrazol-5-yl)-1,2,4-oxadiazol-3-yl]phenyl}-sulphonyl)amino]phenyl}cyclopropanecarboxamide

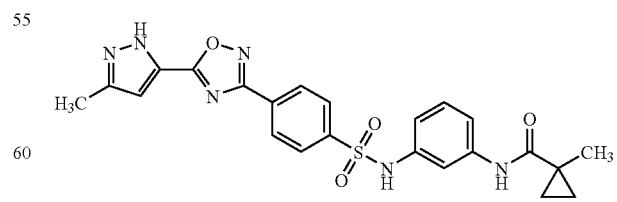

MW 478.53; m/z found: 479 HPLC Rt: 3.77 min. (HPLC method/instrument: 6) $^1$H-NMR (200 MHz, DMSO): δ=0.54–0.65 (m, 2 H), 0.99–1.12 (m, 2 H), 1.36 (s, 3 H), 2.34 (s, 3 H), 6.77 (d, 1 H), 7.10 (t, 1 H), 7.25 (d, 1 H), 7.54 (s, 1 H), 7.95 (d, 2 H), 8.20 (d, 2 H), 9.16 (s, 1 H), 10.38 (s, 1 H), 13.58 (s, 1 H).

Example 7

1-Methyl-N-{3-[({4-[5-(1,3-thiazol-4-yl)-1,2,4-oxadiazol-3-yl]phenyl}sulphonyl)-amino]phenyl}cyclopropanecarboxamide

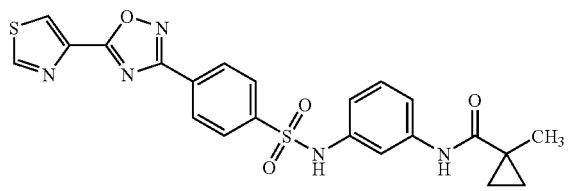

MW 481.56; m/z found: 482 HPLC Rt: 2.689 min. (HPLC method/instrument: 8) $^1$H-NMR (300 Mz, DMSO): δ=0.55–0.63 (m, 2 H), 1.01–1.09 (m, 2 H), 1.36 (s, 3 H), 6.77 (d, 1 H), 7.12 (t, 1 H), 7.28 (d, 1 H), 7.58 (s, 1 H), 7.98 (d, 2 H), 8.24 (d, 2 H), 8.95 (d, 1 H), 9.19 (s, 1 H), 9.40 (d, 1 H), 10.39 (s, 1 H).

Example 8

N-{3-[({4-[5-(1,5-Dimethyl-1H-pyrazol-3-yl)-1,2,4-oxadiazol-3-yl]phenyl}-sulphonyl)amino]phenyl}-1-methylcyclopropanecarboxamide

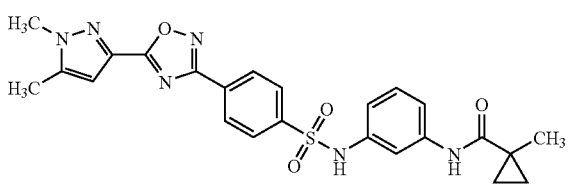

MW 492.56; m/z found: 493 HPLC Rt: 2.788 min. (HPLC method/instrument: 8) $^1$H-NMR (200 MHz, DMSO): δ=0.53–0.64 (m, 2 H), 0.97–1.12 (m, 2 H), 1.36 (s, 3 H), 2.35 (s, 3 H), 3.89 (s, 3 H), 6.77 (d, 1 H), 6.85 (s, 1 H), 7.11 (t, 1 H), 7.27 (d, 1 H), 7.56 (s, 1 H), 7.95 (d, 2 H), 8.21 (d, 2 H), 9.18 (s, 1 H), 10.38 (s, 1 H).

Example 9

1-Methyl-N-{3-[({4-[5-(5-methyl-1H-pyrazol-3-yl)-1,2,4-oxadiazol-3-yl]phenyl}-sulphonyl)amino]phenyl}cyclopropanecarboxamide

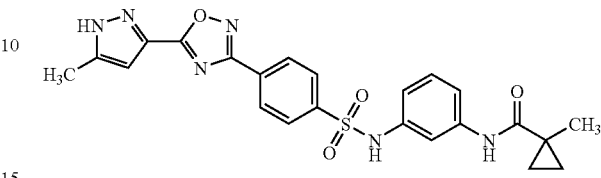

MW 478.53; m/z found: 479 HPLC Rt: 2.614 min. (HPLC method/instrument: 8) $^1$H-NMR (300 MHz, DMSO): δ=0.57–0.63 (m, 2 H), 1.01–1.08 (m, 2 H), 1.36 (s, 3 H), 2.34 (s, 3 H), 6.75–6.80 (m, 2 H), 7.10 (t, 1 H), 7.26 (d, 1 H), 7.54 (s, 1 H), 7.96 (d, 2 H), 8.20 (d, 2 H), 9.16 (s, 1 H), 10.38 (s, 1 H), 13.58 (s, 1 H).

Example 10

N-{3-[({4-[5-(1-Isoquinolinyl)-1,2,4-oxadiazol-3-yl]phenyl}sulphonyl)-amino]phenyl}-1-methylcyclopropanecarboxamide

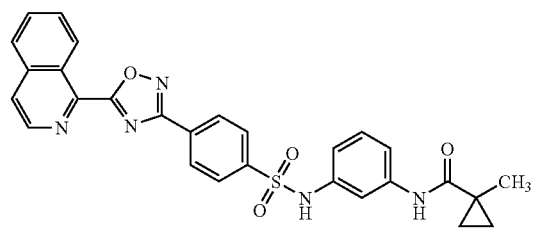

MW 525.59; m/z found: 526 HPLC Rt: 4.34 min. (HPLC method/instrument: 5) $^1$H-NMR (200 MHz, DMSO): δ=0.54–0.67 (m, 2 H), 0.99–1.11 (m, 2 H), 1.36 (s, 3 H), 6.80 (d, 1 H), 7.12 (t, 1 H), 7.28 (d, 1 H), 7.58 (s, 1 H), 7.86–7.99 (m, 2 H), 8.01 (d, 2 H), 8.15–8.29 (m, 1 H), 8.26 (d, 1 H), 8.36 (d, 2 H), 8.82 (d, 1 H), 9.18 (s, 1 H), 9.26–9.36 (m, 1 H), 10.41 (s, 1 H).

Example 11

1-Methyl-N-{3-[({4-[5-(2-methyl-1,3-thiazol-4-yl)-1,2,4-oxadiazol-3-yl]phenyl}-sulphonyl)amino]phenyl}cyclopropanecarboxamide

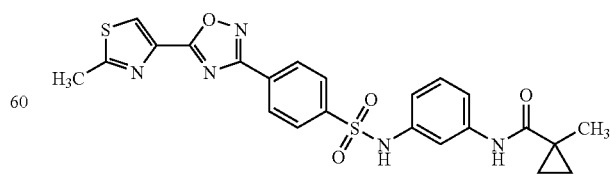

MW 495.58; m/z found: 496 HPLC Rt: 2.813 min. (HPLC method/instrument: 8) $^1$H-NMR (200 MHz, DMSO):

δ=0.55–0.63 (m, 2 H), 1.00–1.09 (m, 2 H), 1.36 (s, 3 H), 2.78 (s, 3 H), 6.78 (d, 1 H), 7.12 (t, 1 H), 7.28 (d, 1 H), 7.58 (s, 1 H), 7.97 (d, 2 H), 8.23 (d, 2 H), 8.73 (s, 1 H), 9.19 (s, 1 H), 13.39 (s, 1 H).

Example 12

N-(3-{[(4-{5-[2-(Aminomethyl)-1,3-thiazol-4-yl]-1,2,4-oxadiazol-3-yl}phenyl)-sulphonyl]amino}phenyl)-1-methylcyclopropanecarboxamide

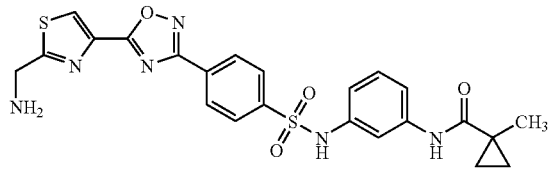

MW 510.60, m/z found: 511 HPLC Rt: 1.71 min. (HPLC method/instrument: 8) $^1$H-NMR (200 MHz, DMSO): δ=0.54–0.64 (m, 2 H), 0.99–1.09 (m, 2 H), 1.36 (s, 3 H), 4.09 (s, 2 H), 6.77 (d, 1 H), 7.11 (t, 1 H), 7.27 (d, 1 H), 7.56 (s, 1 H), 7.96 (d, 2 H), 8.22 (d, 2 H), 8.75 (s, 1 H), 9.18 (s, 1 H).

Example 13

3-Fluoro-2,2-dimethyl-N-[4-({[3-(5-phenyl-1,2,4-oxadiazol-3-yl)phenyl]sulphonyl}-amino)phenyl]propanamide

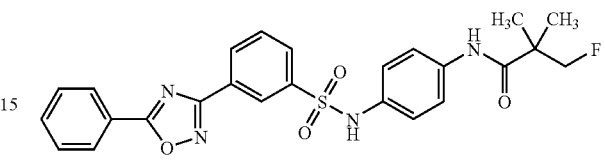

MW 494.54; m/z found: 495 HPLC Rt: 4.8 min. (HPLC method/instrument: 3) $^1$H-NMR (300 MHz, DMSO): δ=1.17 (s, 6 H), 4.44 (d, 2 H), 7.04 (d, 2 H), 7.48 (d, 2 H), 7.63–7.81 (m, 4 H), 7.90 (d, 1 H), 8.22 (d, 2 H), 8.30 (d, 1 H), 8.45 (s, 1 H), 10.31 (s, 1 H).

Further 1,2,4-oxadiazole derivatives which are attached via position 3 and were prepared in accordance with the processes according to the invention are listed in Table 2:

| Example No. | Structure | MW | HPLC R$_t$ [min] | HPLC method/ instrument | m/z found [M + H] |
|---|---|---|---|---|---|
| 14 | 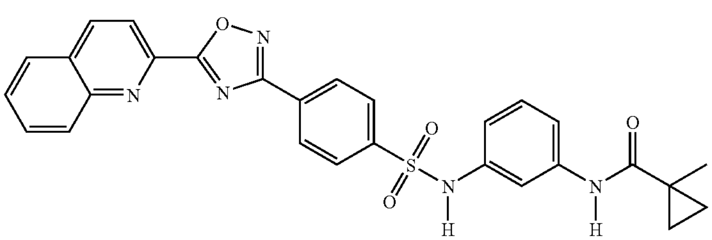 | 525.59 | 5.03 | 6 | 526 |
| 15 | 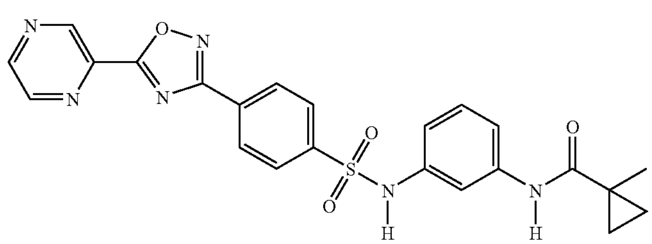 | 476.51 | 2.63 | 8 | 477 |
| 16 | 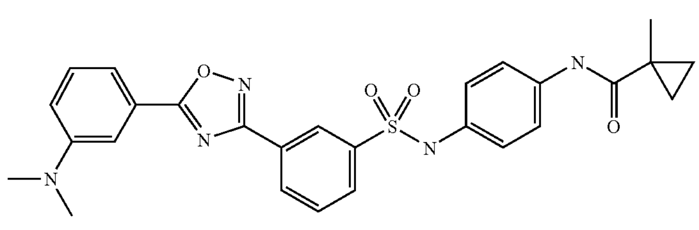 | 517.61 | 4.28 | 3 | 518 |

-continued

| Example No. | Structure | MW | HPLC R$_t$ [min] | HPLC method/ instrument | m/z found [M + H] |
|---|---|---|---|---|---|
| 17 | 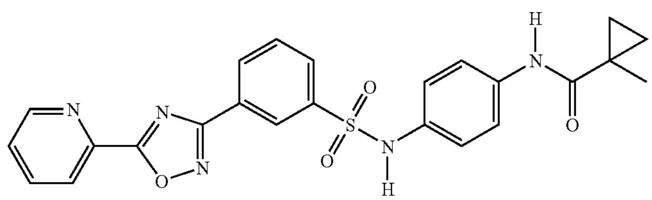 | 475.53 | 3.90 | 6 | 476 |
| 18 | 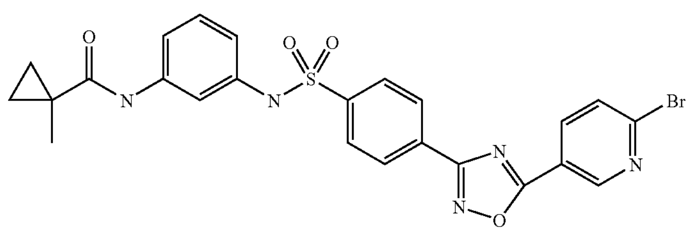 | 554.42 | 4.80 | 3 | 554 (79Br) |
| 19 | 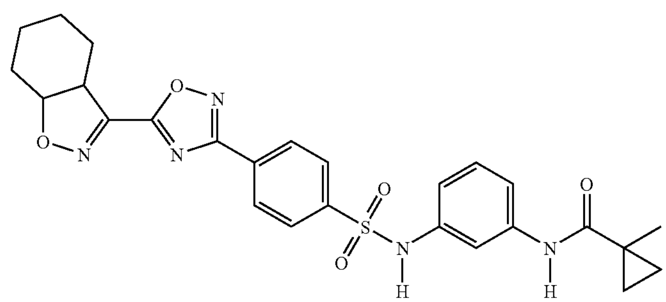 | 521.60 | 3.14 | 8 | 522 |
| 20 | 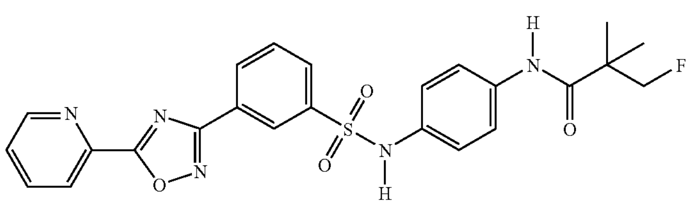 | 495.53 | 4.34 | 3 | 496 |
| 21 | 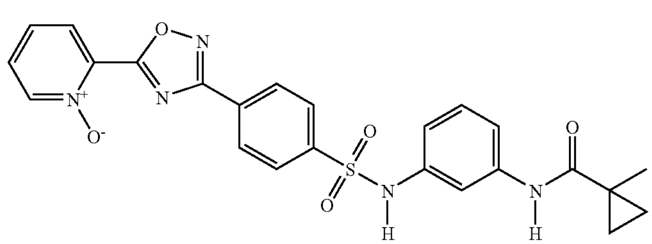 | 491.53 | 3.40 | 6 | 492 |
| 22 | 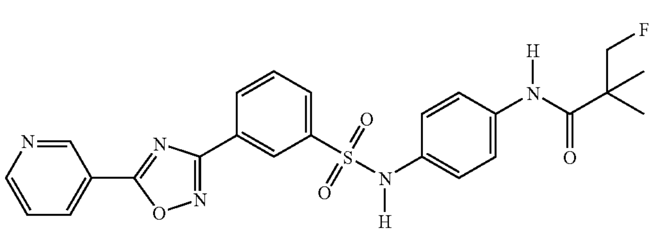 | 495.53 | 4.13 | 3 | 496 |

-continued

| Example No. | Structure | MW | HPLC R₁ [min] | HPLC method/ instrument | m/z found [M + H] |
|---|---|---|---|---|---|
| 23 | 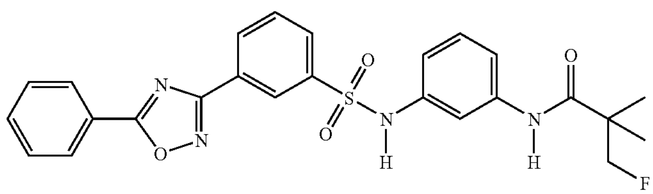 | 494.54 | 4.95 | 3 | 495 |
| 24 | 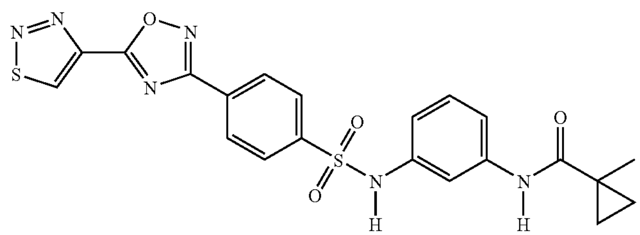 | 482.54 | 2.72 | 8 | 483 |
| 25 | 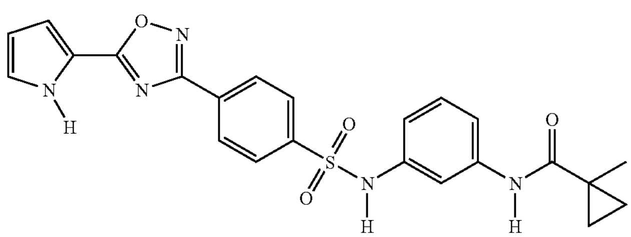 | 463.52 | 2.83 | 8 | 464 |
| 26 | 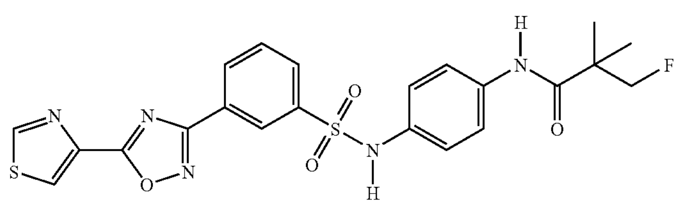 | 501.56 | 4.41 | 3 | 502 |
| 27 | 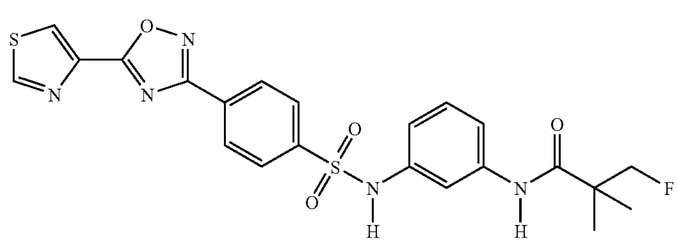 | 501.56 | 4.96 | 3 | 502 |
| 28 | 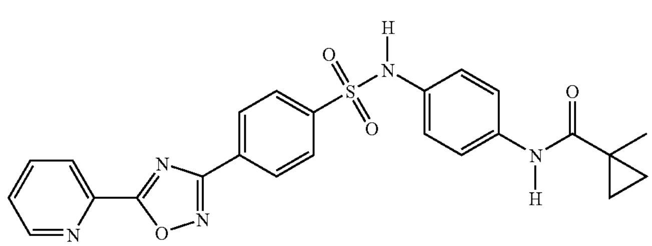 | 475.53 | 2.66 | 8 | 476 |

-continued
| Example No. | Structure | MW | HPLC $R_t$ [min] | HPLC method/ instrument | m/z found [M + H] |
|---|---|---|---|---|---|
| 29 | 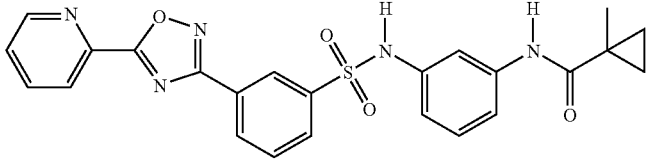 | 475.53 | 2.70 | 8 | 476 |
| 30 | 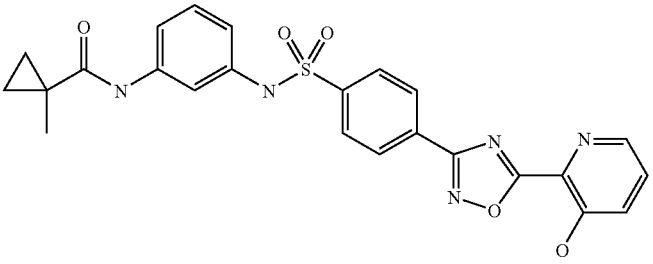 | 492.00 | 4.46 | 3 | 493 |
| 31 | 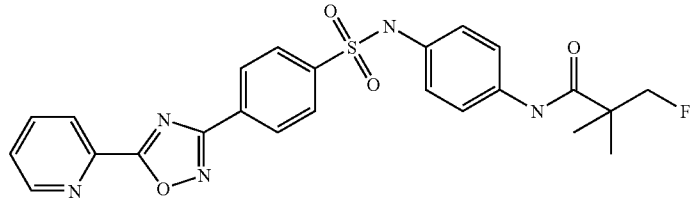 | 495.53 | 4.44 | 3 | 496 |
| 32 | 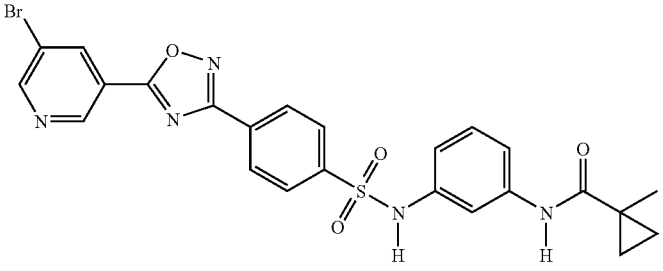 | 554.42 | 4.75 | 3 | 555 |
| 33 | 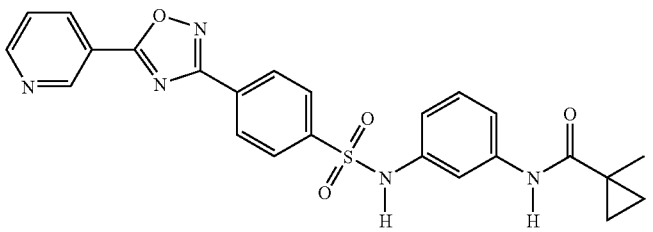 | 475.53 | 3.89 | 6 | 476 |
| 34 | 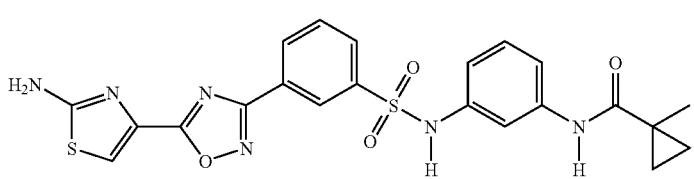 | 496.57 | 3.65 | 5 | 497 |

-continued

| Example No. | Structure | MW | HPLC R$_t$ [min] | HPLC method/ instrument | m/z found [M + H] |
|---|---|---|---|---|---|
| 35 | 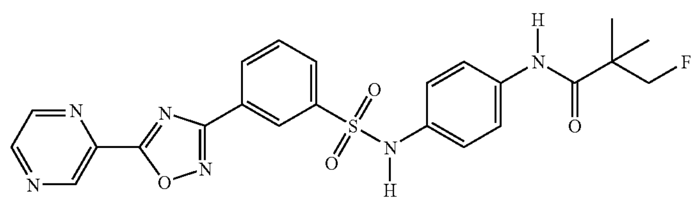 | 496.52 | 4.30 | 3 | 497 |
| 36 | 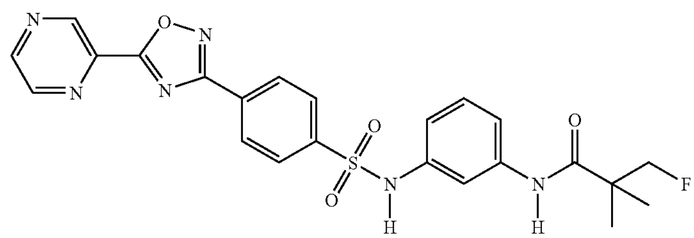 | 496.52 | 4.33 | 3 | 497 |
| 37 | 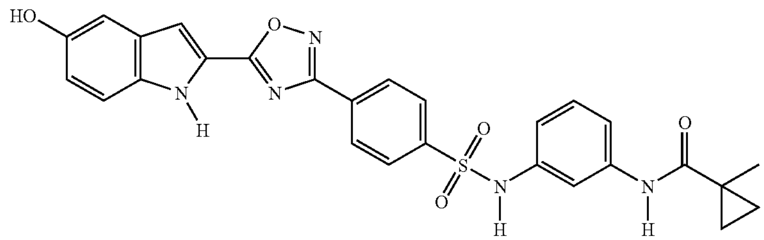 | 529.58 | 2.68 | 8 | 530 |
| 38 | 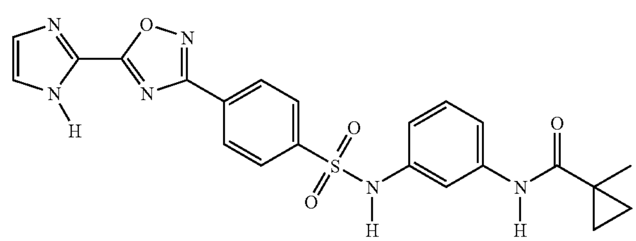 | 464.50 | 2.36 | 8 | 465 |
| 39 | 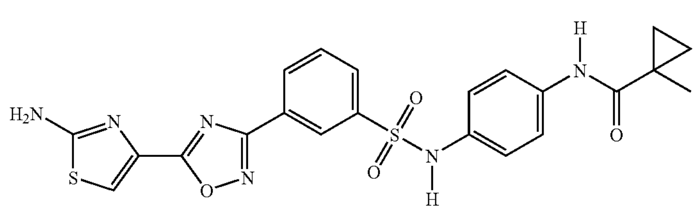 | 496.57 | 2.52 | 8 | 497 |
| 40 | 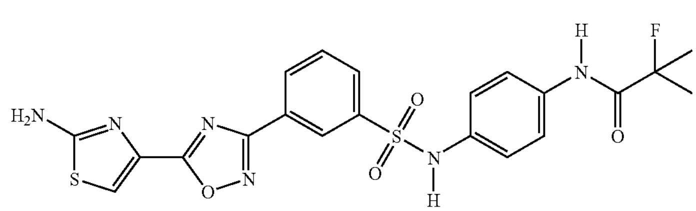 | 516.58 | 4.19 | 3 | 517 |

-continued

| Example No. | Structure | MW | HPLC R₁ [min] | HPLC method/ instrument | m/z found [M + H] |
|---|---|---|---|---|---|
| 41 | 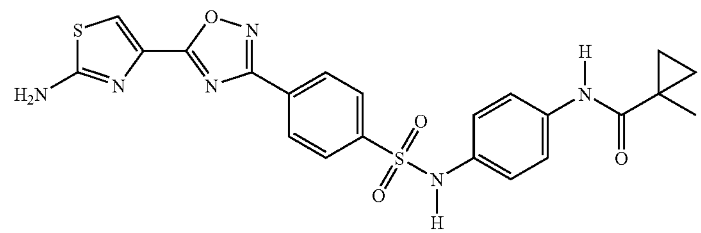 | 496.57 | 3.59 | 5 | 497 |
| 42 | 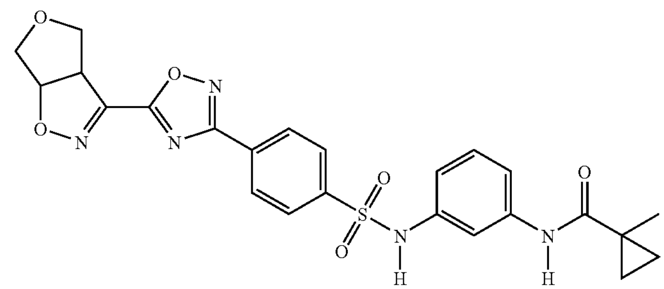 | 509.54 | 2.69 | 8 | 510 |
| 43 | 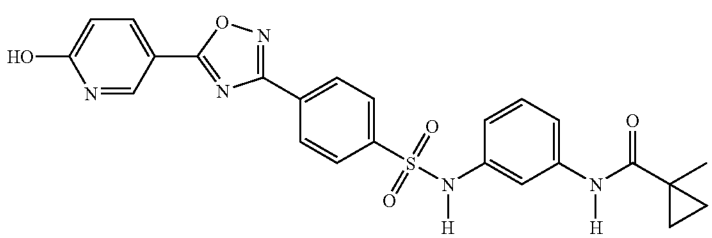 | 491.53 | 3.98 | 3 | 492 |
| 44 | 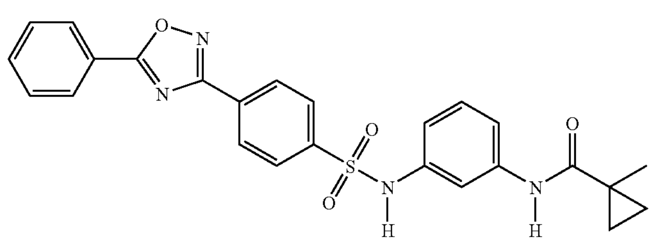 | 474.54 | 4.55 | 6 | 475 |
| 45 | 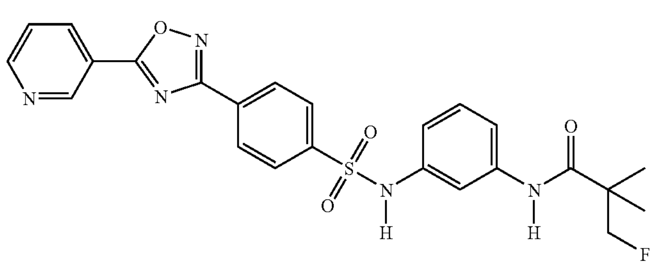 | 495.53 | 4.17 | 3 | 496 |
| 46 | 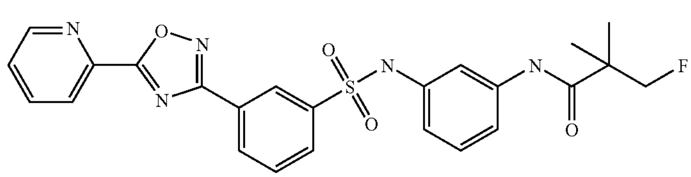 | 495.53 | 4.49 | 3 | 496 |

-continued

| Example No. | Structure | MW | HPLC R₁ [min] | HPLC method/ instrument | m/z found [M + H] |
|---|---|---|---|---|---|
| 47 | 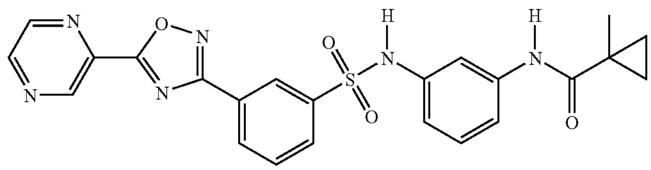 | 475.52 | 2.63 | 8 | 476 |
| 48 | 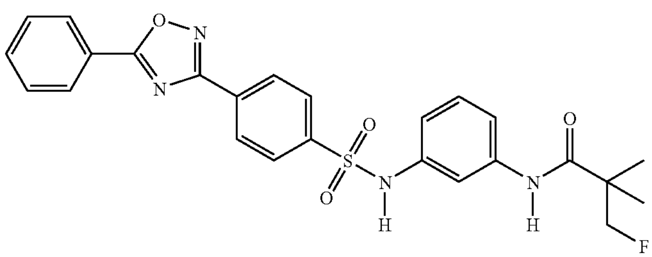 | 494.54 | 4.87 | 3 | 495 |
| 49 | 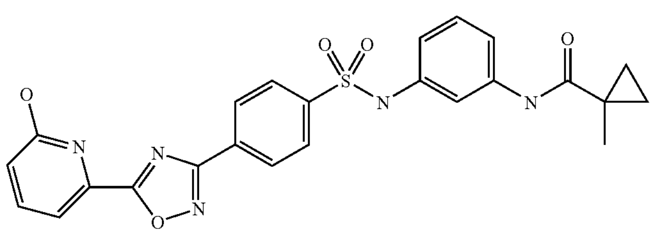 | 492.00 | 4.10 | 3 | 493 |
| 50 | 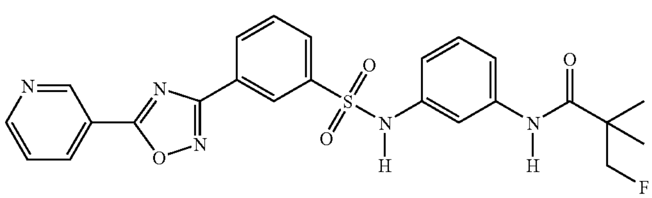 | 495.53 | 4.18 | 3 | 496 |
| 51 | 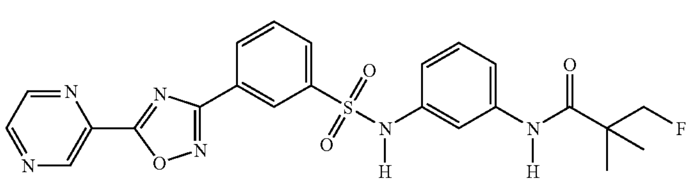 | 496.52 | 4.32 | 3 | 497 |

-continued
| Example No. | Structure | MW | HPLC R$_1$ [min] | HPLC method/ instrument | m/z found [M + H] |
|---|---|---|---|---|---|
| 52 | 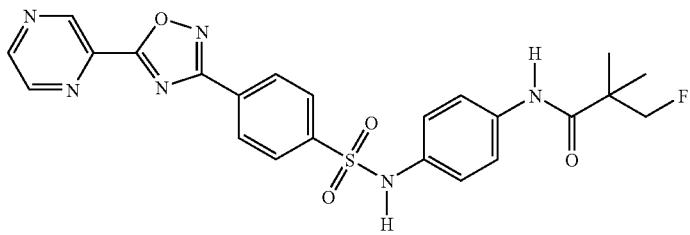 | 496.52 | 4.35 | 3 | 497 |
| 53 | 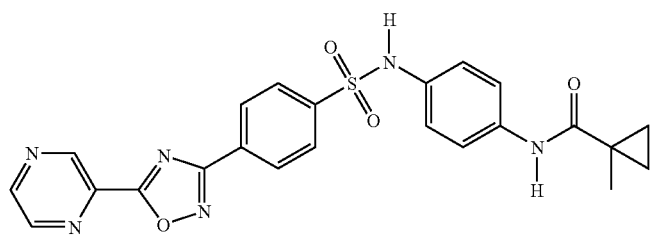 | 475.52 | 2.60 | 8 | 476 |
| 54 | 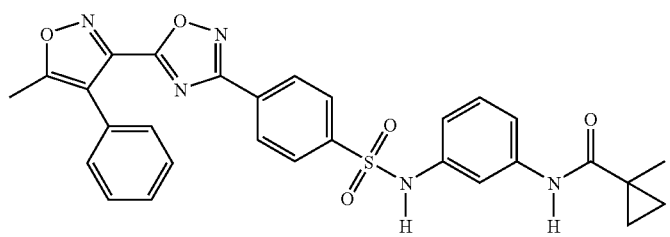 | 555.61 | 4.64 | 6 | 556 |

Further 1,3,4-oxadiazole derivatives attached via position 5 and prepared according to the processes according to the invention are listed in Table 3:

| Example No. | Structure | MW | m/z found [M + H] | HPLC R$_t$ [min] | HPLC method/ instrument |
|---|---|---|---|---|---|
| 55 | 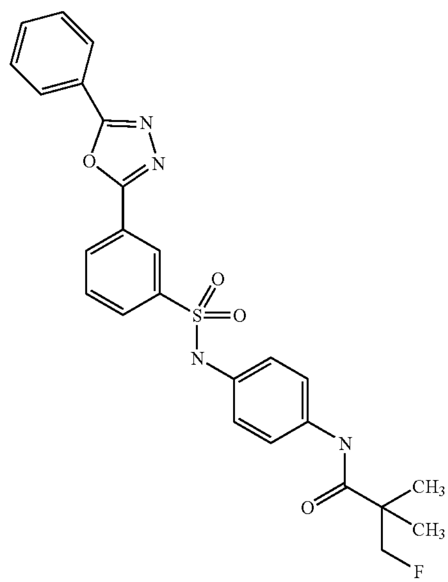 | 494.55 | 495 | 4.15 | 6 |
| 56 | 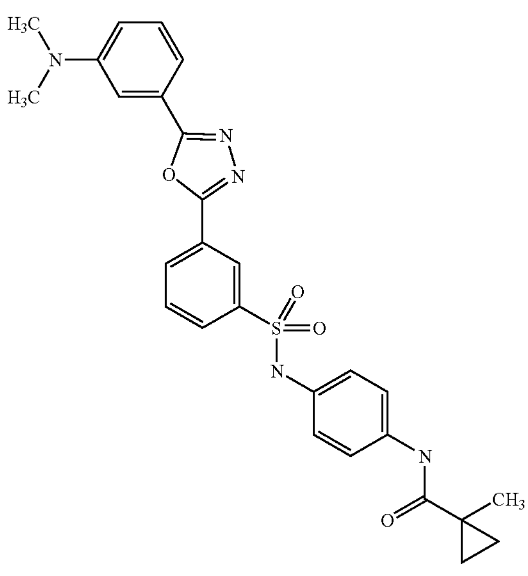 | 517.61 | 515 | 4.26 | 6 |

-continued
| Example No. | Structure | MW | m/z found [M + H] | HPLC R₁ [min] | HPLC method/ instrument |
|---|---|---|---|---|---|
| 57 | 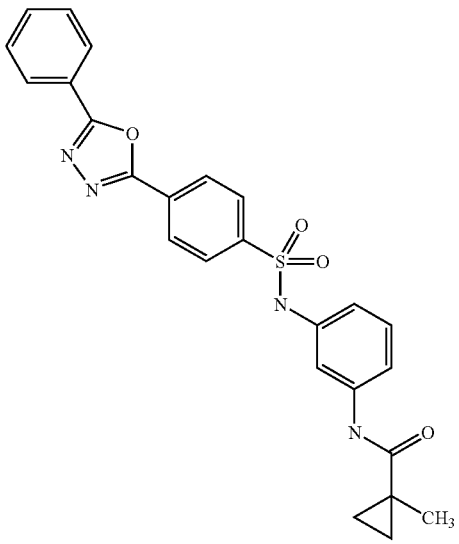 | 474.54 | 475 | 4.17 | 6 |
| 58 | 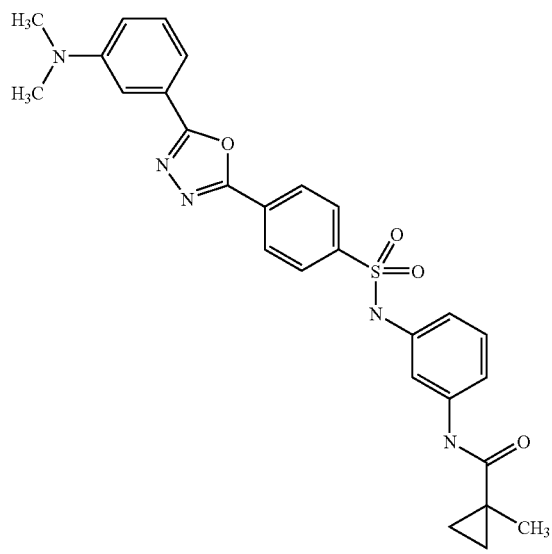 | 517.61 | 518 | 4.35 | 6 |

-continued
| Example No. | Structure | MW | m/z found [M + H] | HPLC R₁ [min] | HPLC method/ instrument |
|---|---|---|---|---|---|
| 59 | 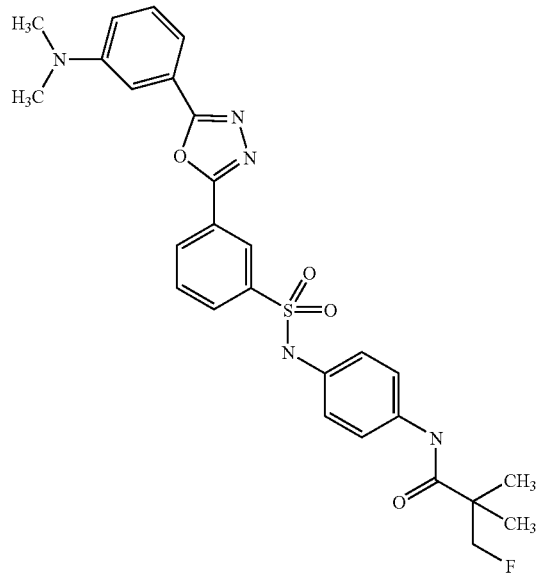 | 537.62 | 538 | 4.3 | 6 |
| 60 | 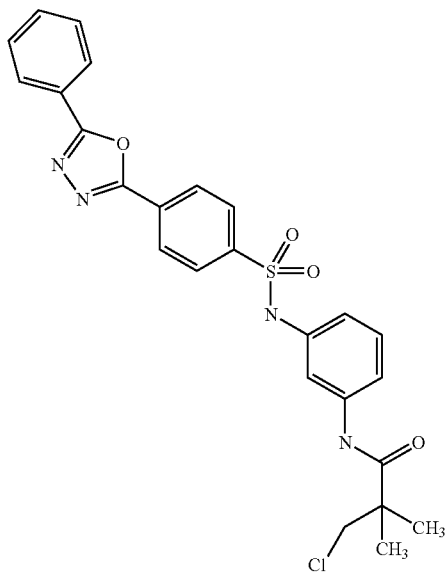 | 511.00 | 511, 513 (35Cl, 37Cl) | 4.31 | 6 |

-continued
| Example No. | Structure | MW | m/z found [M + H] | HPLC R$_t$ [min] | HPLC method/ instrument |
|---|---|---|---|---|---|
| 61 | 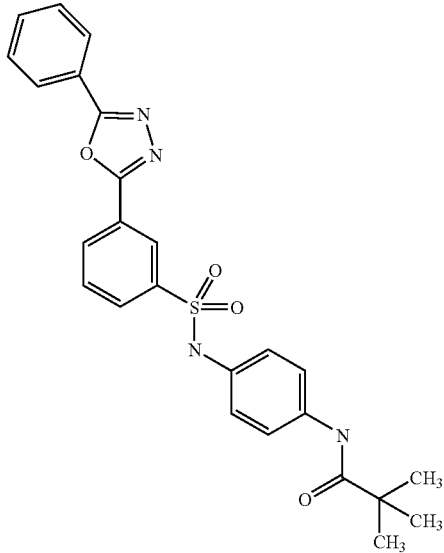 | 476.58 | 477 | 4.23 | 6 |
| 62 | 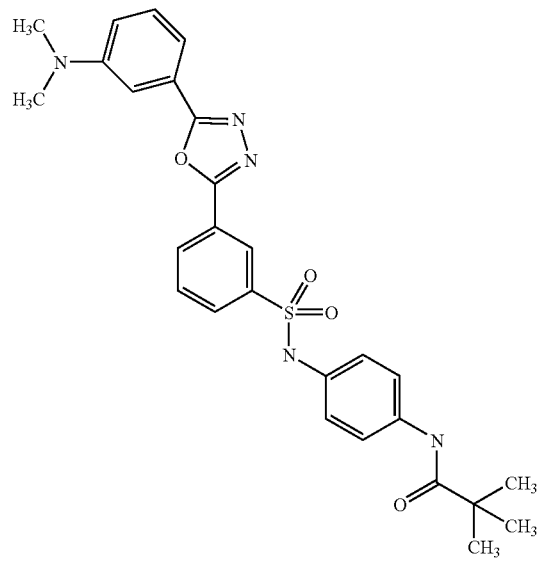 | 519.63 | 520 | 4.38 | 6 |

-continued

| Example No. | Structure | MW | m/z found [M + H] | HPLC R$_t$ [min] | HPLC method/ instrument |
|---|---|---|---|---|---|
| 63 | 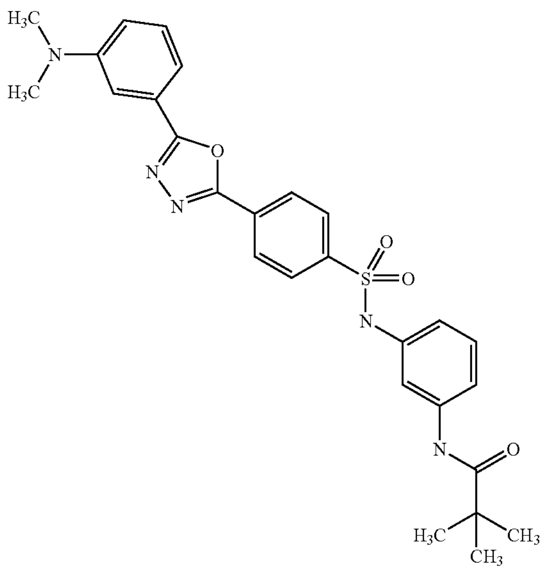 | 519.63 | 520 | 4.44 | 6 |
| 64 | 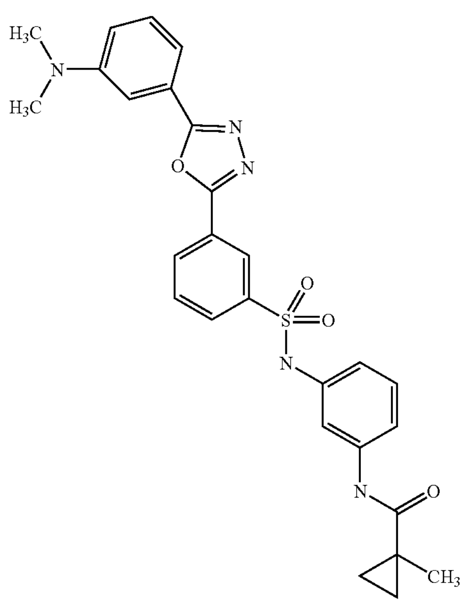 | 517.61 | 518 | 4.33 | 6 |

-continued
| Example No. | Structure | MW | m/z found [M + H] | HPLC R$_t$ [min] | HPLC method/ instrument |
|---|---|---|---|---|---|
| 65 | 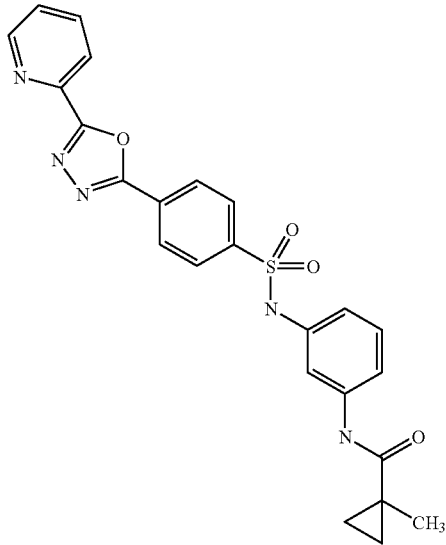 | 475.53 | 476 | 3.66 | 6 |
| 66 | 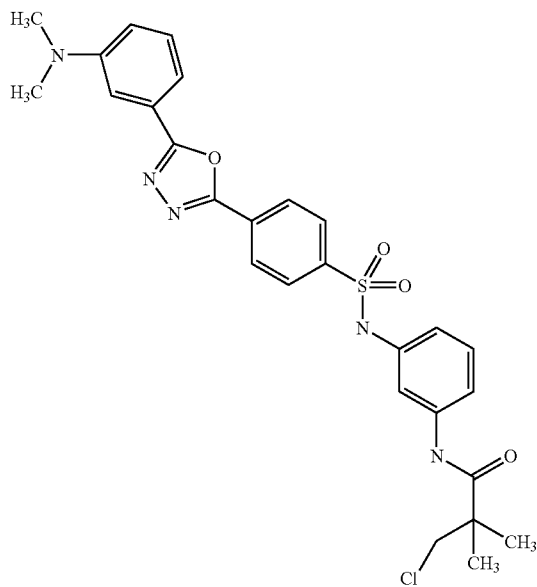 | 554.07 | 554, 556 (35Cl, 37Cl) | 4.48 | 6 |

-continued

| Example No. | Structure | MW | m/z found [M + H] | HPLC R$_t$ [min] | HPLC method/ instrument |
|---|---|---|---|---|---|
| 67 | 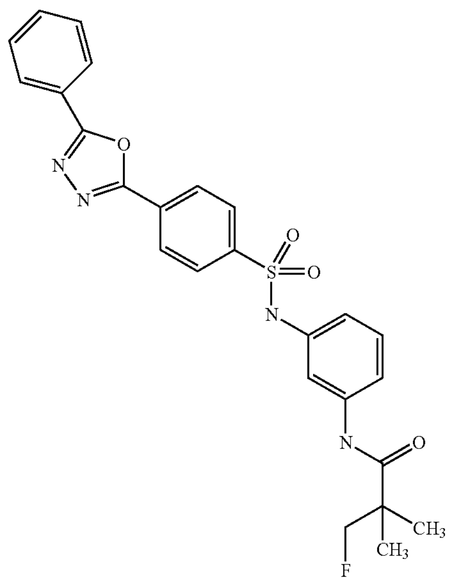 | 494.55 | 495 | 4.20 | 6 |
| 68 | 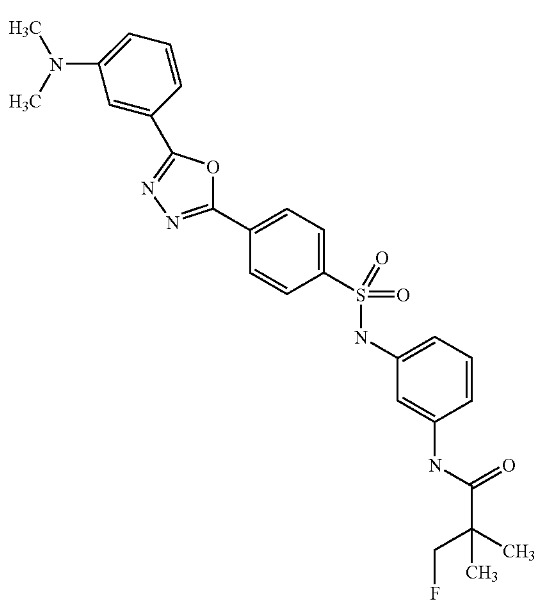 | 537.62 | 538 | 4.37 | 6 |

-continued
| Example No. | Structure | MW | m/z found [M + H] | HPLC R$_t$ [min] | HPLC method/ instrument |
|---|---|---|---|---|---|
| 69 | 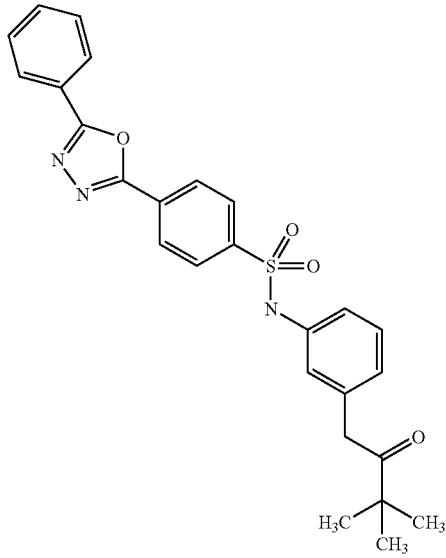 | 476.56 | 477 | 4.27 | 6 |
| 70 | 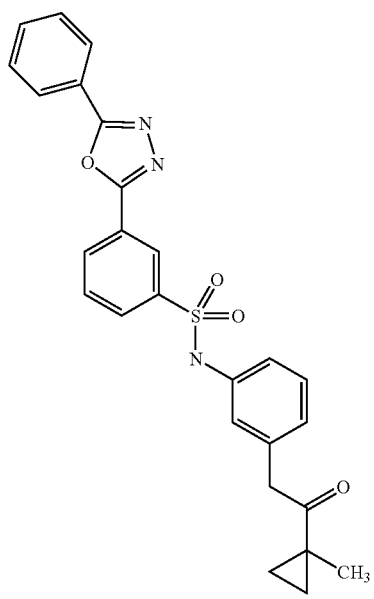 | 474.54 | 475 | 4.17 | 6 |

-continued

| Example No. | Structure | MW | m/z found [M + H] | HPLC R$_t$ [min] | HPLC method/ instrument |
|---|---|---|---|---|---|
| 71 | 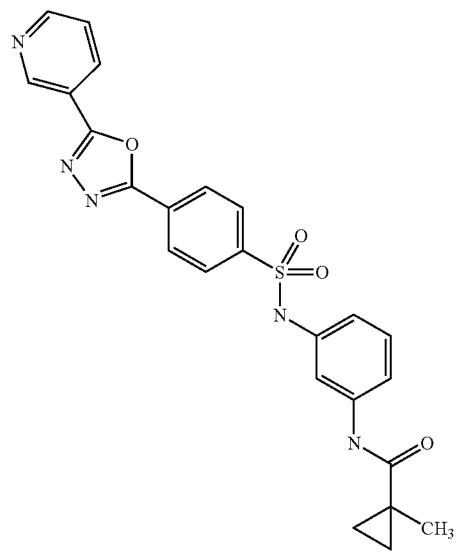 | 475.53 | 476 | 3.60 | 6 |
| 72 | 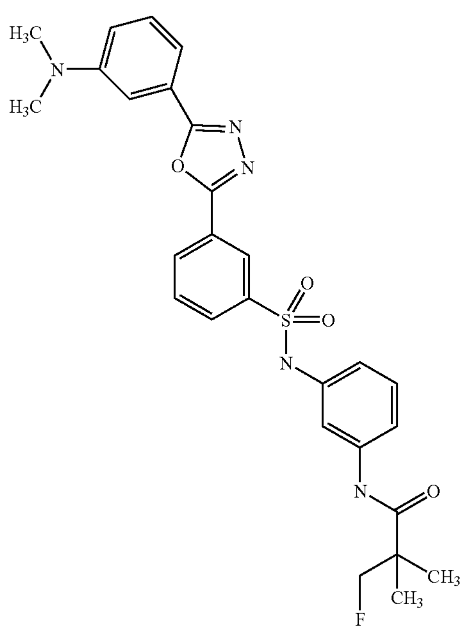 | 537.62 | 538 | 4.35 | 6 |

-continued
| Example No. | Structure | MW | m/z found [M + H] | HPLC R$_t$ [min] | HPLC method/ instrument |
|---|---|---|---|---|---|
| 73 | 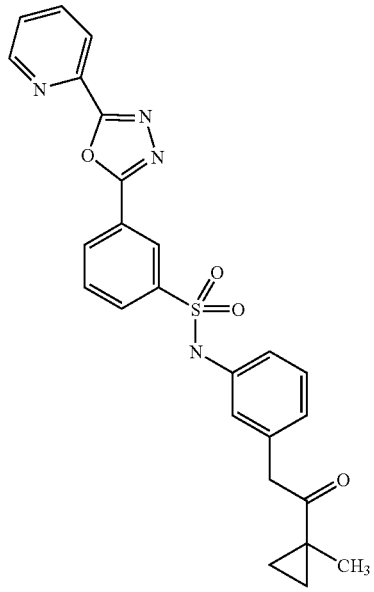 | 475.53 | 475 | 3.69 | 6 |
| 74 | 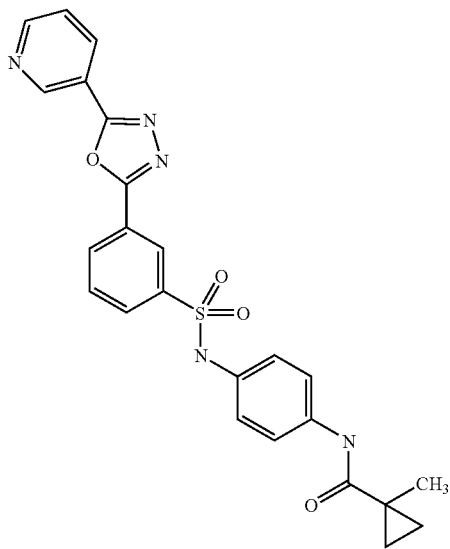 | 475.53 | 476 | 3.54 | 6 |

-continued
| Example No. | Structure | MW | m/z found [M + H] | HPLC R_t [min] | HPLC method/ instrument |
|---|---|---|---|---|---|
| 75 | 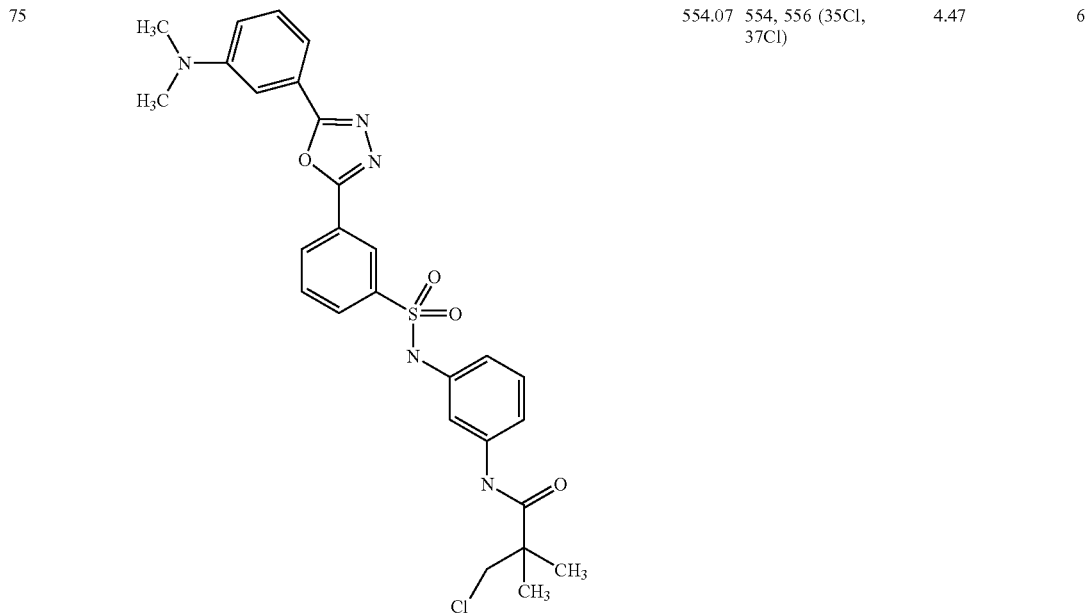 | 554.07 | 554, 556 (35Cl, 37Cl) | 4.47 | 6 |
| 76 | 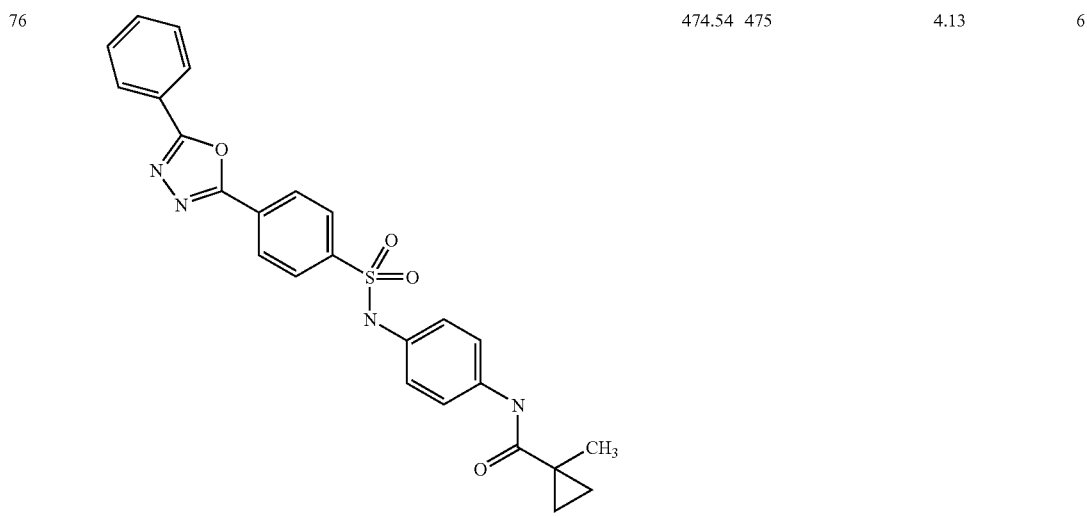 | 474.54 | 475 | 4.13 | 6 |

| Example No. | Structure | MW | m/z found [M + H] | HPLC R$_t$ [min] | HPLC method/ instrument |
|---|---|---|---|---|---|
| 77 | 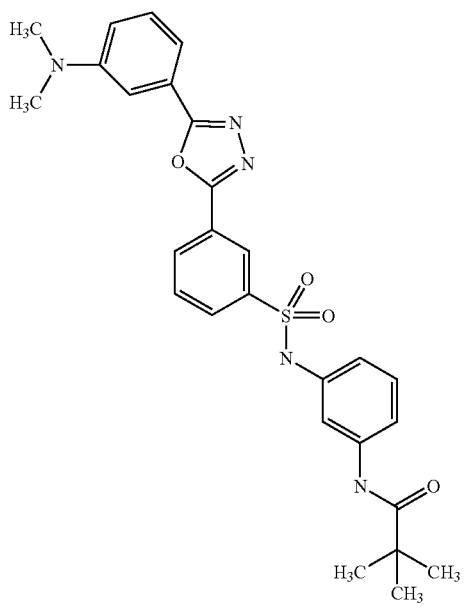 | 519.63 | 520 | 4.43 | 6 |
| 78 | 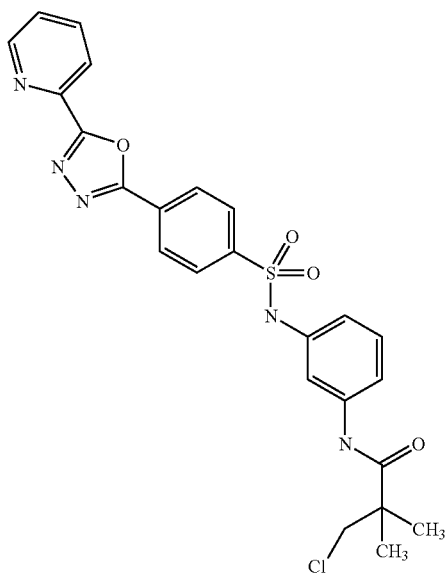 | 511.99 | 512, 514 (35Cl, 37Cl) | 3.84 | 6 |

-continued
| Example No. | Structure | MW | m/z found [M + H] | HPLC R$_t$ [min] | HPLC method/ instrument |
|---|---|---|---|---|---|
| 79 | 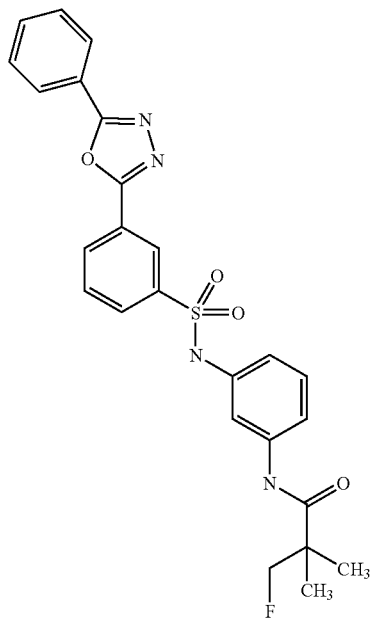 | 494.55 | 495 | 4.2 | 6 |
| 80 | 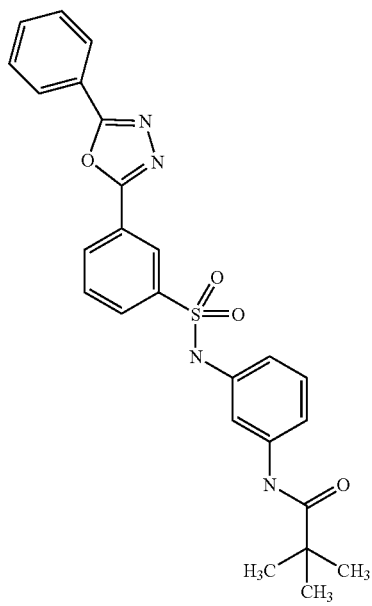 | 476.56 | 477 | 4.28 | 6 |

-continued
| Example No. | Structure | MW | m/z found [M + H] | HPLC R₁ [min] | HPLC method/ instrument |
|---|---|---|---|---|---|
| 81 | 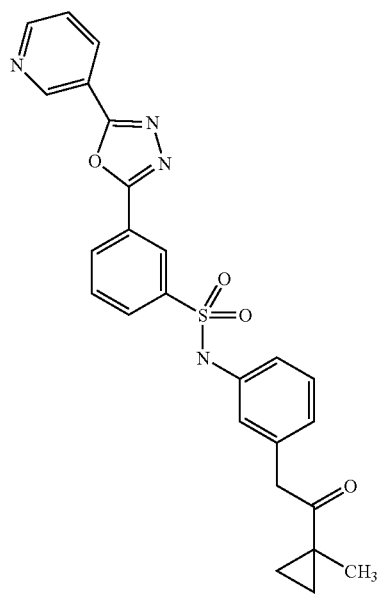 | 475.53 | 476 | 3.6 | 6 |
| 82 | 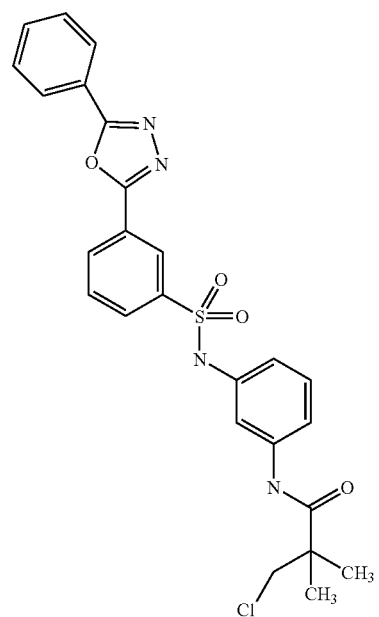 | 511.00 | 511, 513 (35Cl, 37Cl) | 4.32 | 8 |

-continued
| Example No. | Structure | MW | m/z found [M + H] | HPLC $R_t$ [min] | HPLC method/ instrument |
|---|---|---|---|---|---|
| 83 | 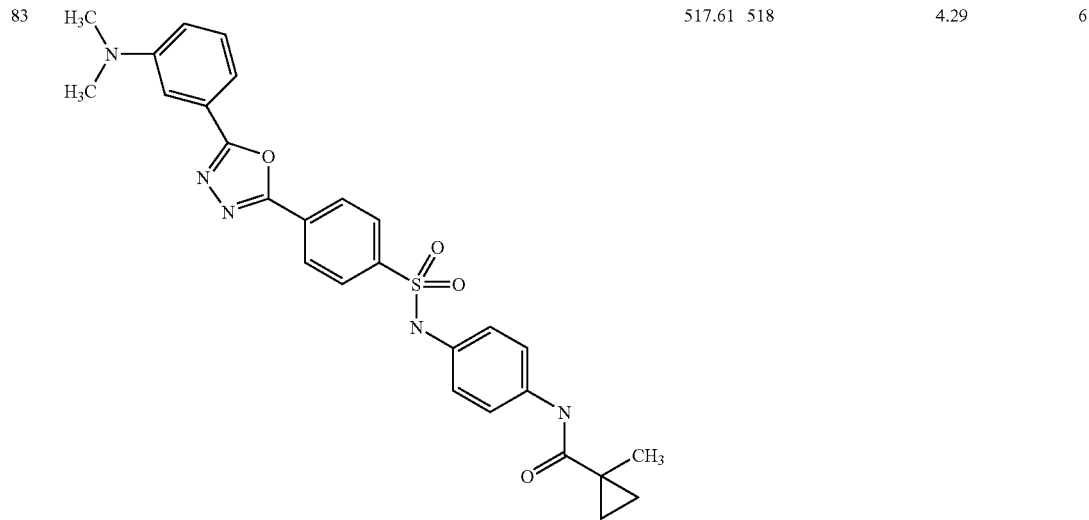 | 517.61 | 518 | 4.29 | 6 |
| 84 | 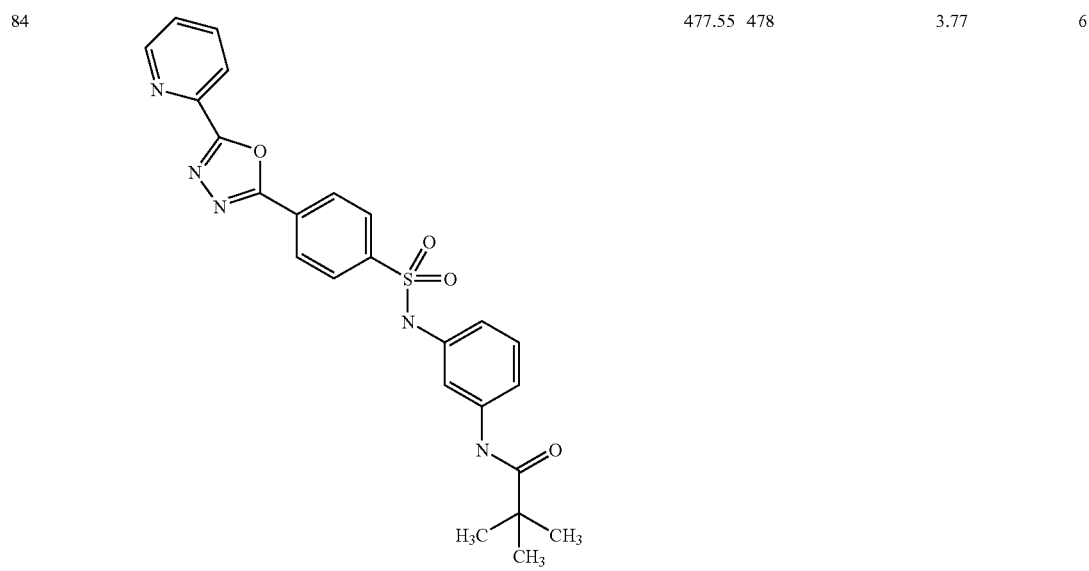 | 477.55 | 478 | 3.77 | 6 |

-continued
| Example No. | Structure | MW | m/z found [M + H] | HPLC $R_t$ [min] | HPLC method/ instrument |
|---|---|---|---|---|---|
| 85 | 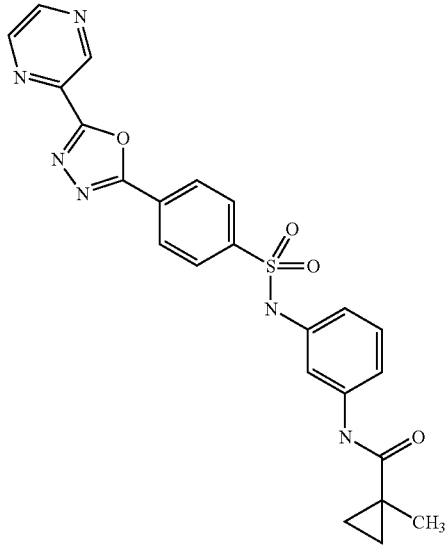 | 476.52 | 477 | 3.56 | 6 |
| 86 | 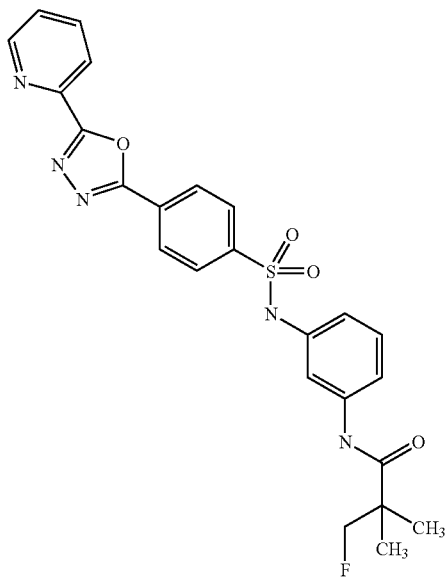 | 495.54 | 496 | 3.71 | 6 |

-continued

| Example No. | Structure | MW | m/z found [M + H] | HPLC R$_t$ [min] | HPLC method/ instrument |
|---|---|---|---|---|---|
| 87 | 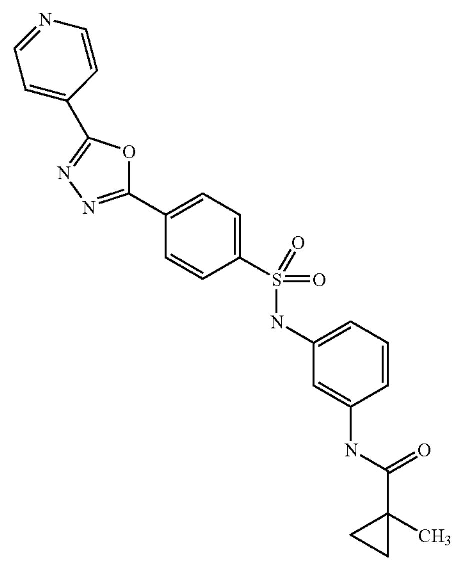 | 475.53 | 476 | 3.55 | 6 |
| 88 | 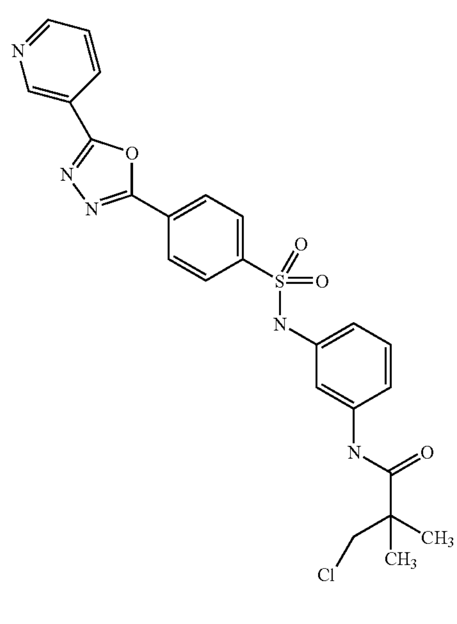 | 511.99 | 512, 514 (35Cl, 37Cl) | 3.78 | 6 |

-continued
| Example No. | Structure | MW | m/z found [M + H] | HPLC $R_t$ [min] | HPLC method/ instrument |
|---|---|---|---|---|---|
| 89 | 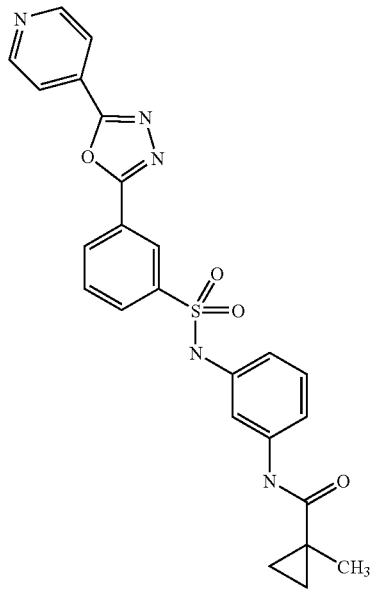 | 475.53 | 476 | 3.55 | 6 |
| 90 | 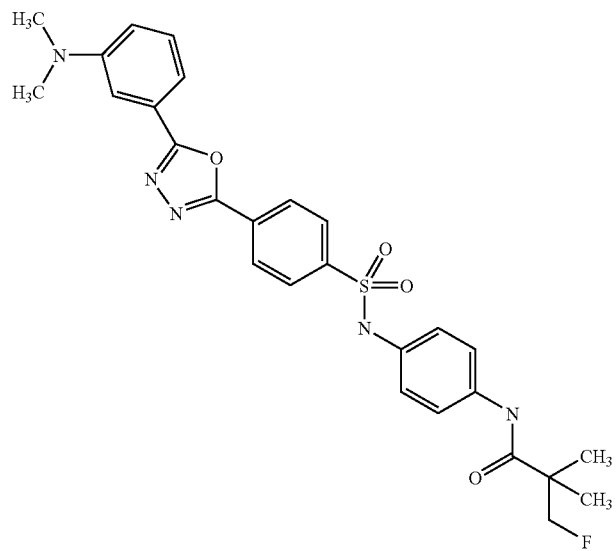 | 537.62 | 538 | 4.32 | 6 |

-continued
| Example No. | Structure | MW | m/z found [M + H] | HPLC $R_t$ [min] | HPLC method/ instrument |
|---|---|---|---|---|---|
| 91 | 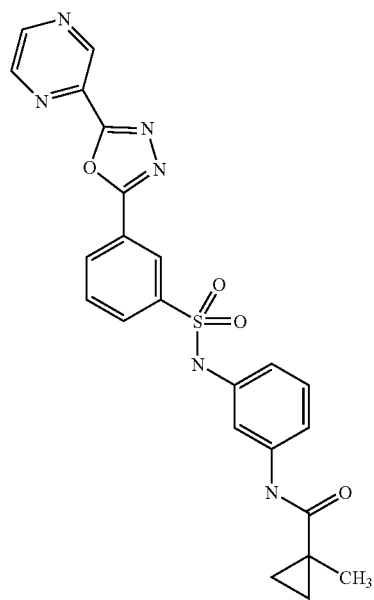 | 476.52 | 477 | 3.57 | 6 |
| 92 | 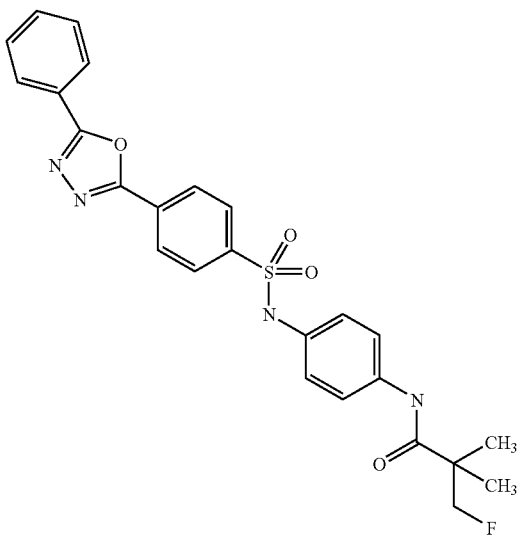 | 494.55 | 495 | 4.17 | 6 |

-continued

| Example No. | Structure | MW | m/z found [M + H] | HPLC R$_t$ [min] | HPLC method/ instrument |
|---|---|---|---|---|---|
| 93 | 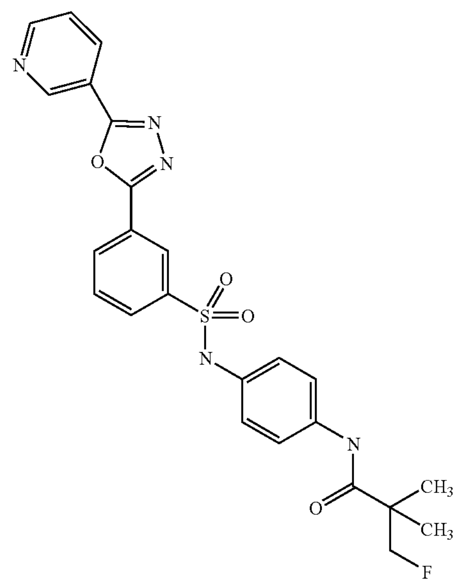 | 495.54 | 496 | 3.6 | 6 |
| 94 | 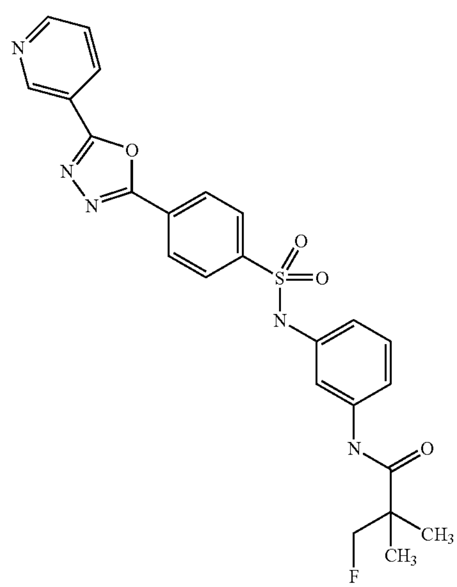 | 495.54 | 496 | 3.64 | 6 |

-continued

| Example No. | Structure | MW | m/z found [M + H] | HPLC R$_t$ [min] | HPLC method/ instrument |
|---|---|---|---|---|---|
| 95 | 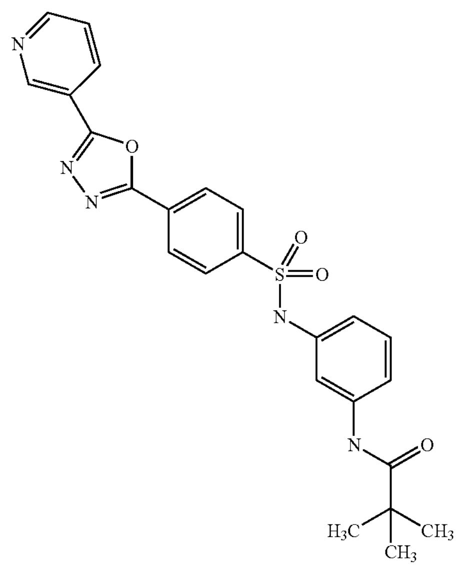 | 477.55 | 478 | 3.71 | 6 |
| 96 | 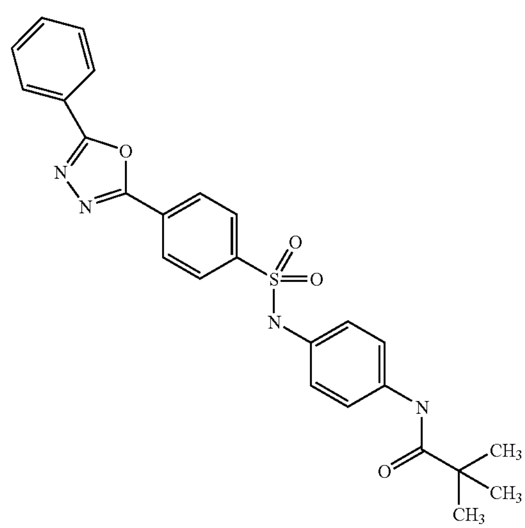 | 476.56 | 477 | 4.24 | 6 |

-continued
| Example No. | Structure | MW | m/z found [M + H] | HPLC R$_t$ [min] | HPLC method/ instrument |
|---|---|---|---|---|---|
| 97 | 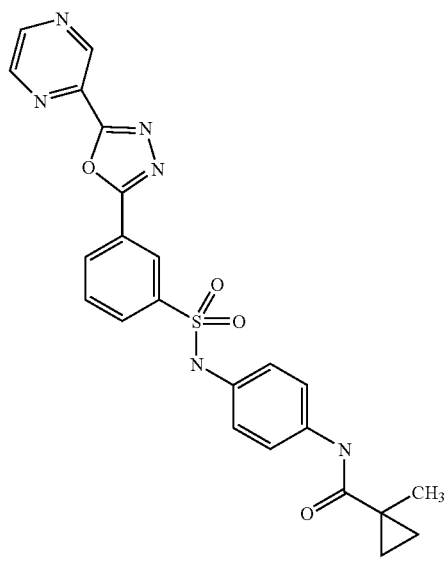 | 476.52 | 477 | 3.51 | 6 |
| 98 | 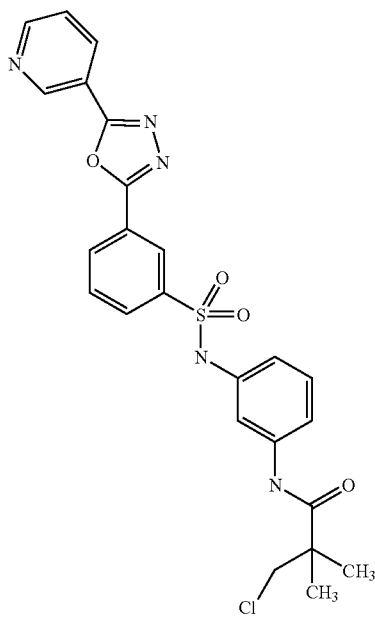 | 511.99 | 512, 514 (35Cl, 37Cl) | 3.78 | 6 |

-continued
| Example No. | Structure | MW | m/z found [M + H] | HPLC R$_t$ [min] | HPLC method/ instrument |
|---|---|---|---|---|---|
| 99 | 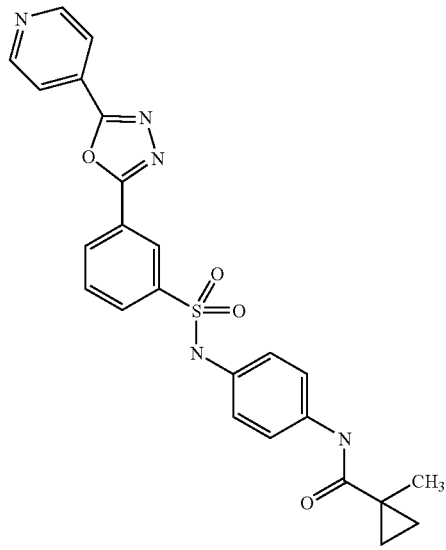 | 475.53 | 476 | 3.48 | 6 |
| 100 | 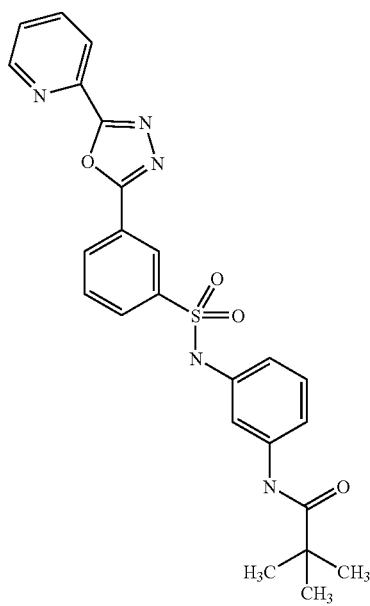 | 477.55 | 478 | 3.8 | 6 |

-continued

| Example No. | Structure | MW | m/z found [M + H] | HPLC $R_t$ [min] | HPLC method/ instrument |
|---|---|---|---|---|---|
| 101 | 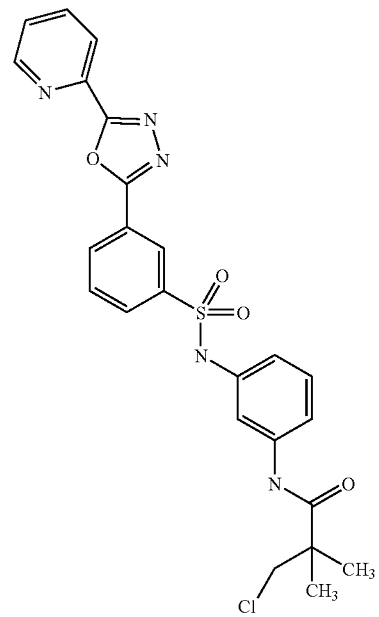 | 511.99 | 512, 514 (35Cl, 37Cl) | 3.87 | 6 |
| 102 | 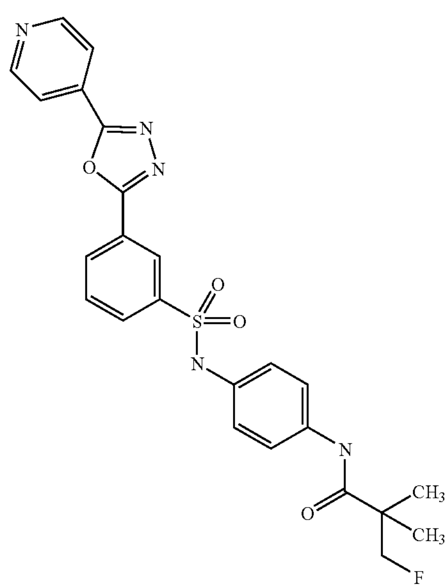 | 495.54 | 496 | 3.54 | 6 |

-continued

| Example No. | Structure | MW | m/z found [M + H] | HPLC R$_t$ [min] | HPLC method/ instrument |
|---|---|---|---|---|---|
| 103 | 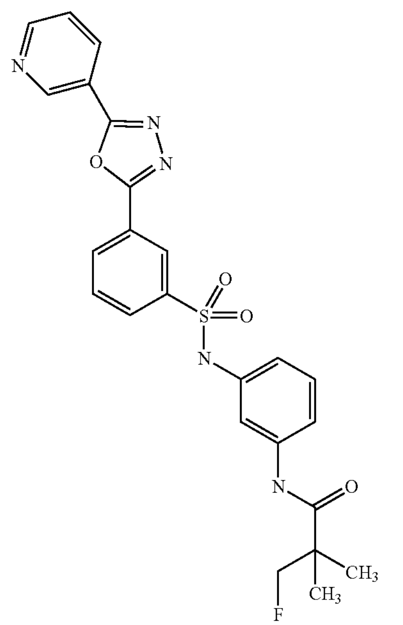 | 495.54 | 496 | 3.64 | 6 |
| 104 | 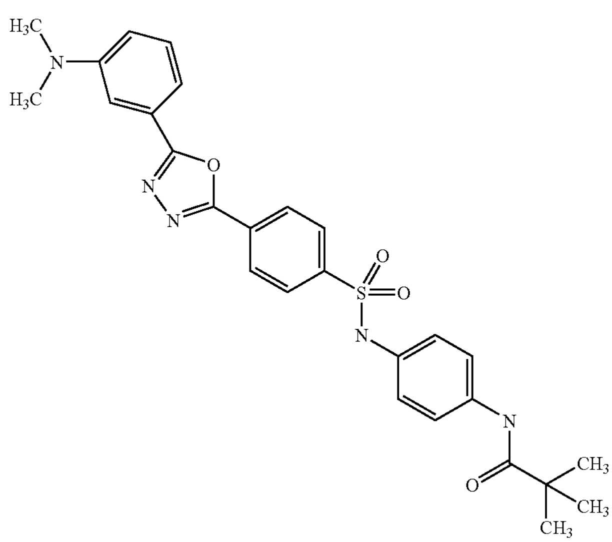 | 519.63 | 520 | 4.4 | 6 |

-continued
| Example No. | Structure | MW | m/z found [M + H] | HPLC R$_t$ [min] | HPLC method/ instrument |
|---|---|---|---|---|---|
| 105 | 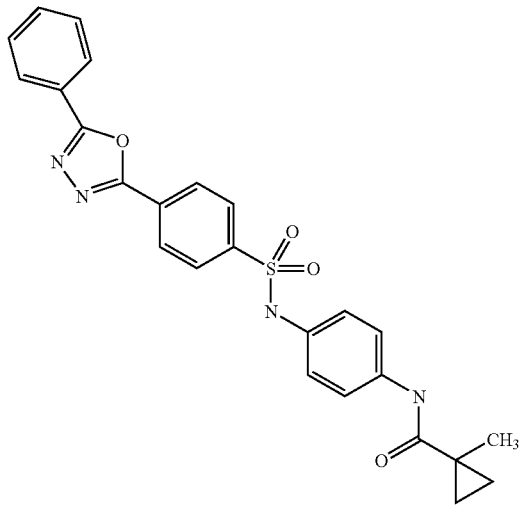 | 475.53 | 476 | 3.55 | 6 |
| 106 | 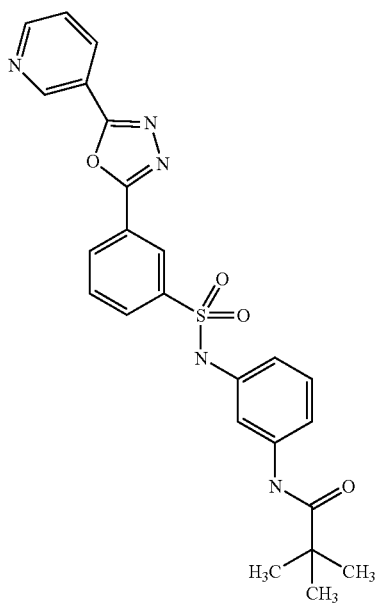 | 477.55 | 478 | 3.71 | 6 |

-continued
| Example No. | Structure | MW | m/z found [M + H] | HPLC $R_t$ [min] | HPLC method/ instrument |
|---|---|---|---|---|---|
| 107 | 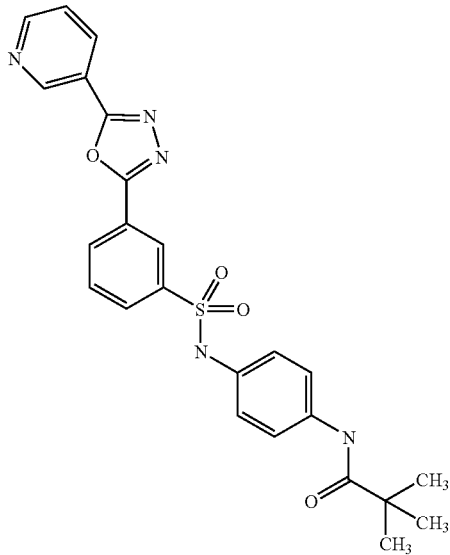 | 477.55 | 478 | 3.67 | 6 |
| 108 | 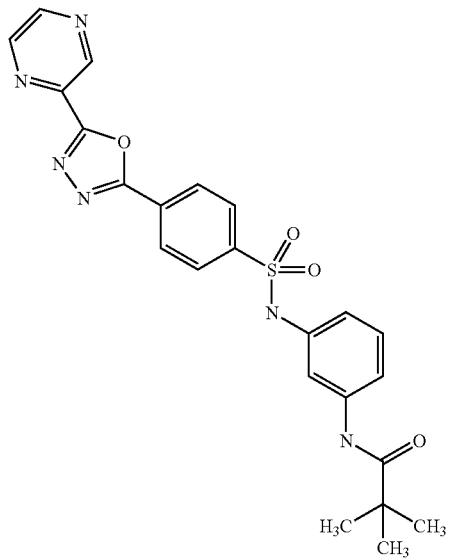 | 478.53 | 479 | 3.67 | 6 |

-continued
| Example No. | Structure | MW | m/z found [M + H] | HPLC $R_t$ [min] | HPLC method/ instrument |
|---|---|---|---|---|---|
| 109 | 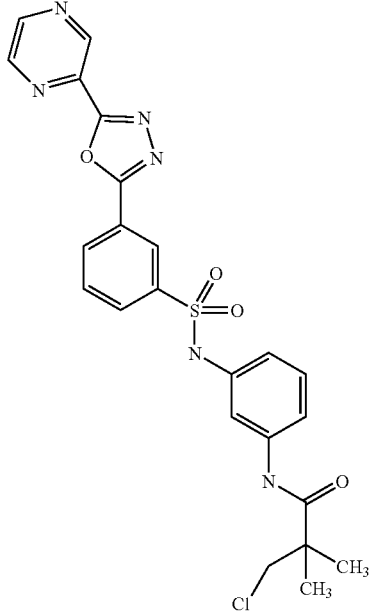 | 512.98 | 513, 515 (35Cl, 37Cl) | 3.76 | 6 |
| 110 | 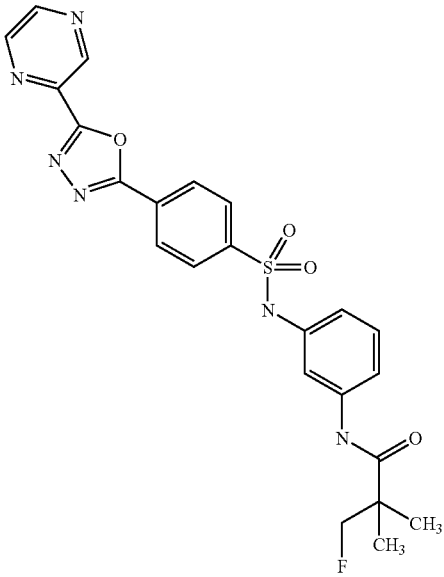 | 496.52 | 497 | 3.60 | 6 |

-continued
| Example No. | Structure | MW | m/z found [M + H] | HPLC R$_t$ [min] | HPLC method/ instrument |
|---|---|---|---|---|---|
| 111 | 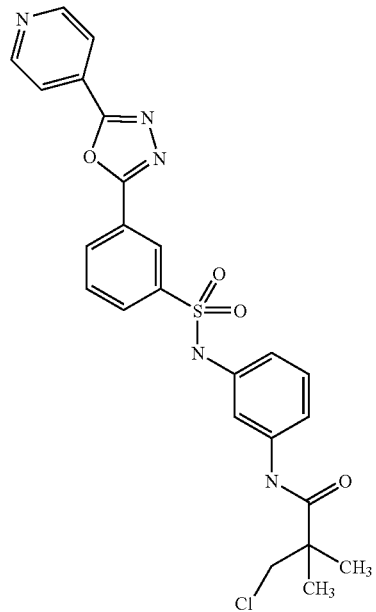 | 511.99 | 512, 514 (35Cl, 37Cl) | 3.73 | 6 |
| 112 | 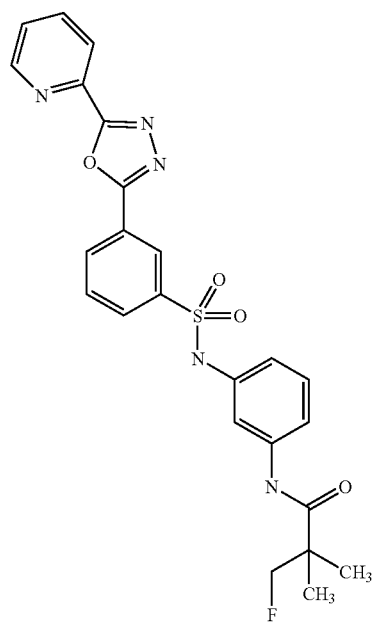 | 495.54 | 496 | 3.73 | 6 |

-continued

| Example No. | Structure | MW | m/z found [M + H] | HPLC R$_t$ [min] | HPLC method/ instrument |
|---|---|---|---|---|---|
| 113 | 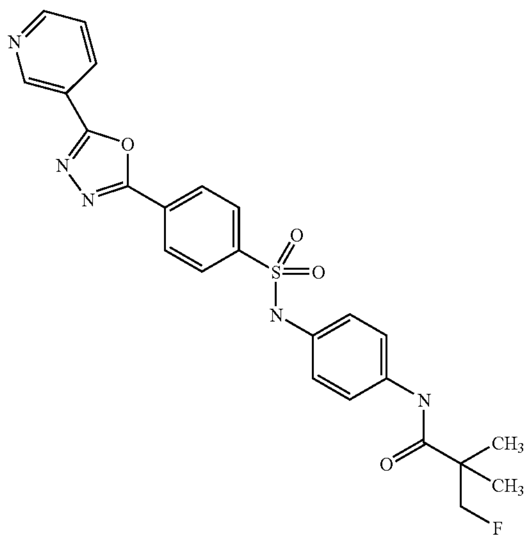 | 495.54 | 496 | 3.6 | 6 |
| 114 | 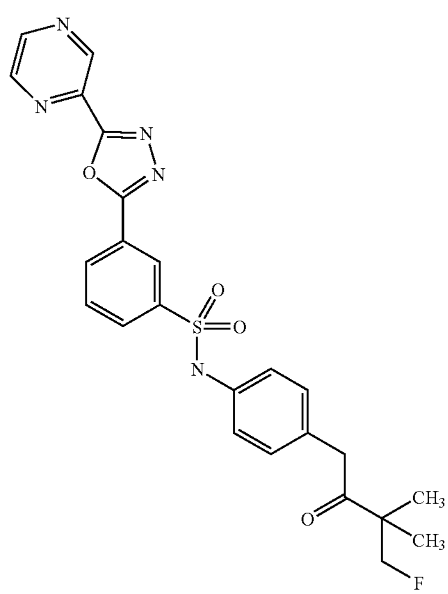 | 495.52 | 497 | 3.57 | 6 |

-continued

| Example No. | Structure | MW | m/z found [M + H] | HPLC R$_t$ [min] | HPLC method/ instrument |
|---|---|---|---|---|---|
| 115 | 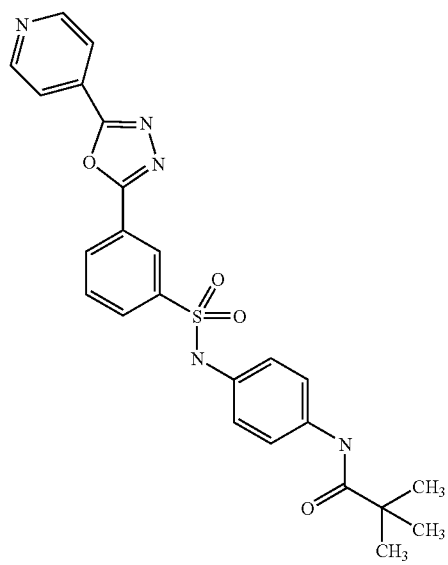 | 477.55 | 478 | 3.61 | 6 |
| 116 | 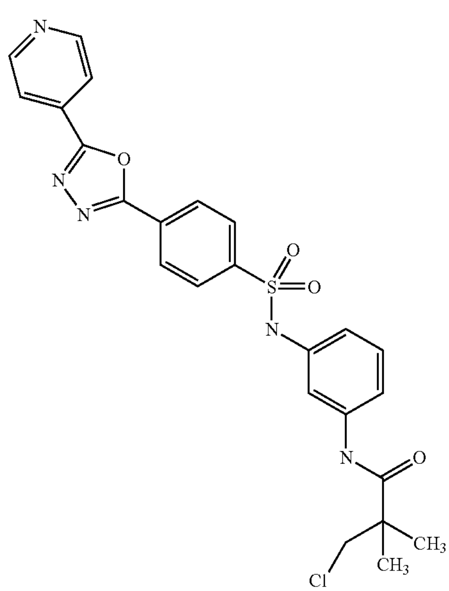 | 511.99 | 512, 514 (35Cl, 37Cl) | 3.74 | 6 |

| Example No. | Structure | MW | m/z found [M + H] | HPLC R₁ [min] | HPLC method/ instrument |
|---|---|---|---|---|---|
| 117 | 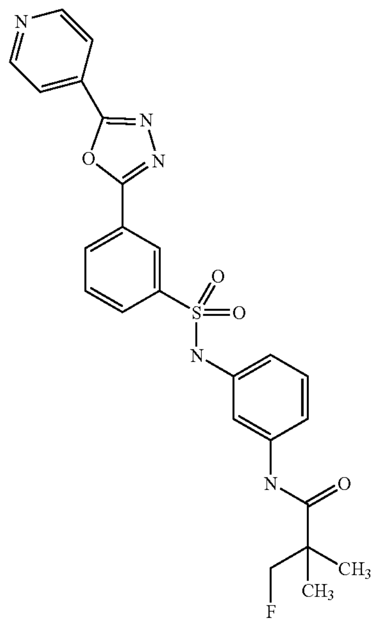 | 495.54 | 496 | 3.59 | 6 |
| 118 | 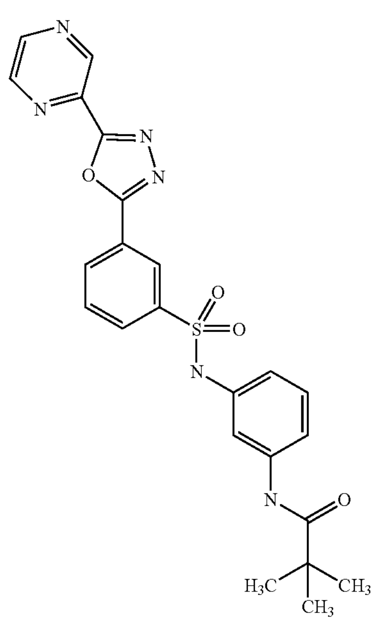 | 478.53 | 479 | 3.68 | 6 |

-continued
| Example No. | Structure | MW | m/z found [M + H] | HPLC R$_t$ [min] | HPLC method/ instrument |
|---|---|---|---|---|---|
| 119 | 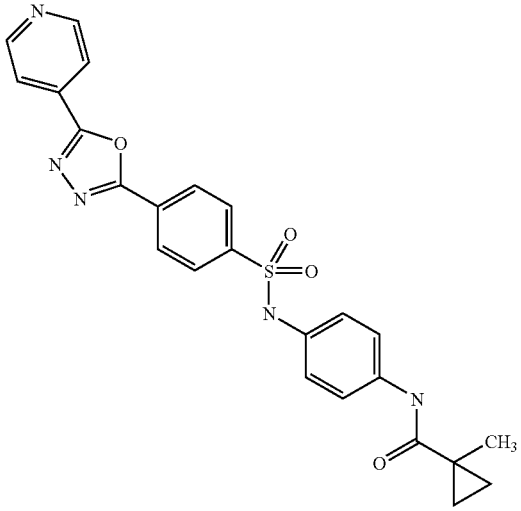 | 475.53 | 476 | 3.5 | 6 |
| 120 | 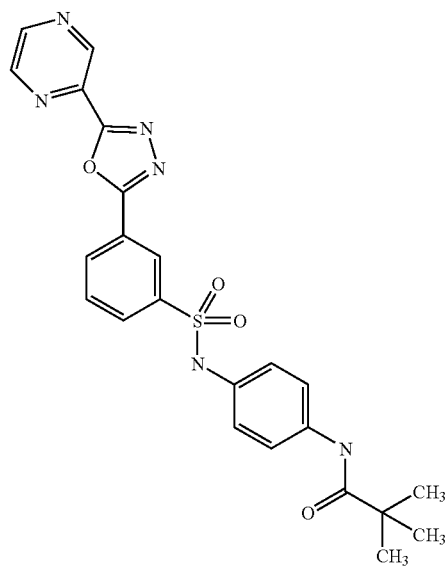 | 478.53 | 479 | 3.64 | 6 |

-continued

| Example No. | Structure | MW | m/z found [M + H] | HPLC R$_t$ [min] | HPLC method/ instrument |
|---|---|---|---|---|---|
| 121 | 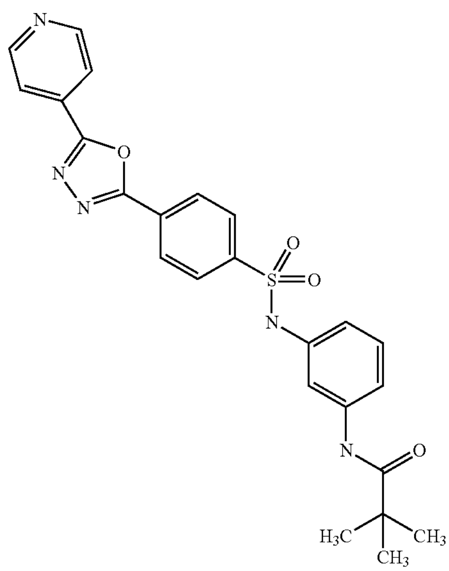 | 477.55 | 478 | 3.66 | 6 |
| 122 | 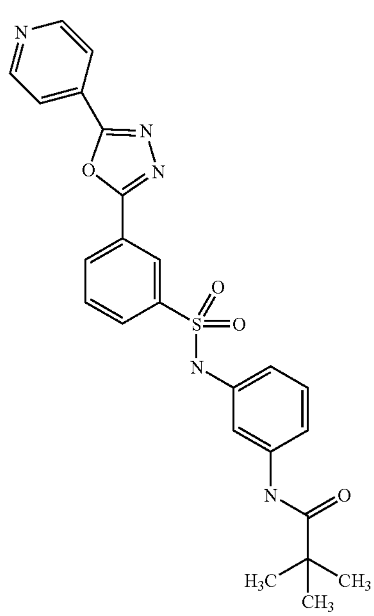 | 477.55 | 478 | 3.66 | 6 |

-continued

| Example No. | Structure | MW | m/z found [M + H] | HPLC R₁ [min] | HPLC method/ instrument |
|---|---|---|---|---|---|
| 123 | 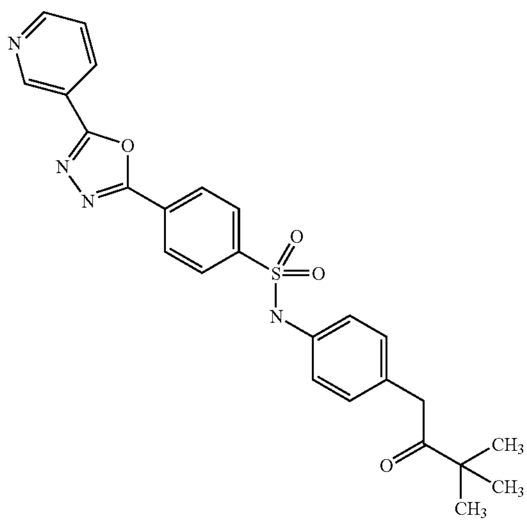 | 477.55 | 478 | 3.67 | 6 |
| 124 | 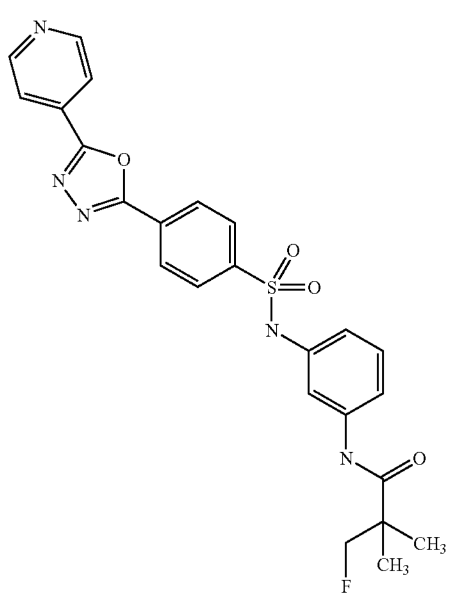 | 495.54 | 496 | 3.60 | 6 |

-continued

| Example No. | Structure | MW | m/z found [M + H] | HPLC R$_t$ [min] | HPLC method/ instrument |
|---|---|---|---|---|---|
| 125 | 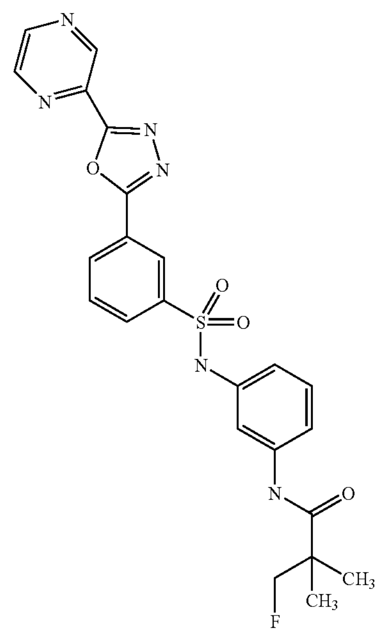 | 496.52 | 497 | 3.61 | 6 |
| 126 | 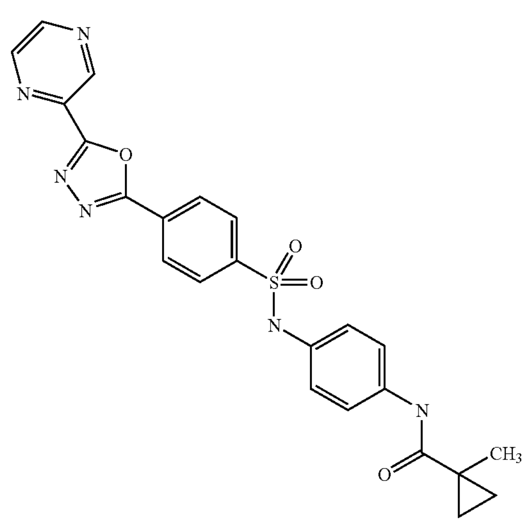 | 476.52 | 477 | 3.51 | 6 |

-continued
| Example No. | Structure | MW | m/z found [M + H] | HPLC $R_t$ [min] | HPLC method/ instrument |
|---|---|---|---|---|---|
| 127 | 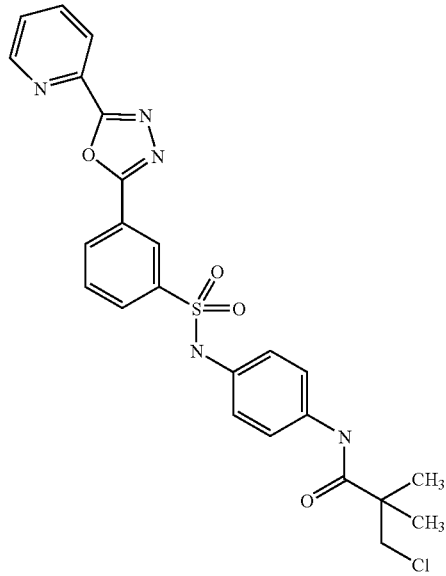 | 511.99 | 512, 514 (35Cl, 37Cl) | 3.86 | 6 |
| 128 | 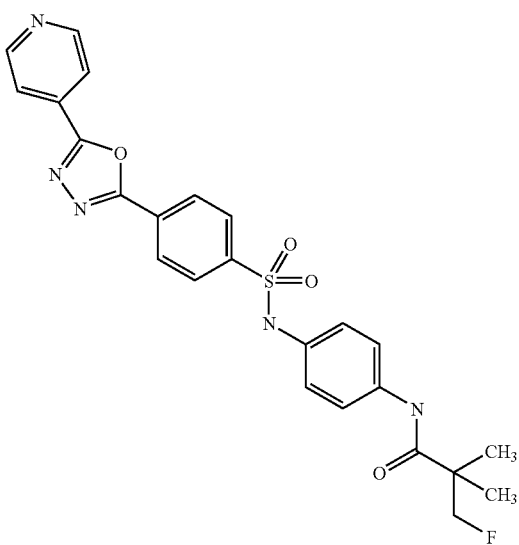 | 495.54 | 496 | 3.55 | 6 |

-continued

| Example No. | Structure | MW | m/z found [M + H] | HPLC R$_t$ [min] | HPLC method/ instrument |
|---|---|---|---|---|---|
| 129 | 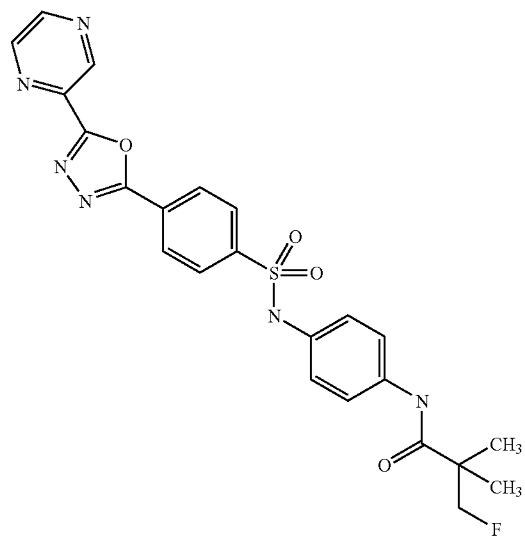 | 496.52 | 497 | 3.56 | 6 |
| 130 | 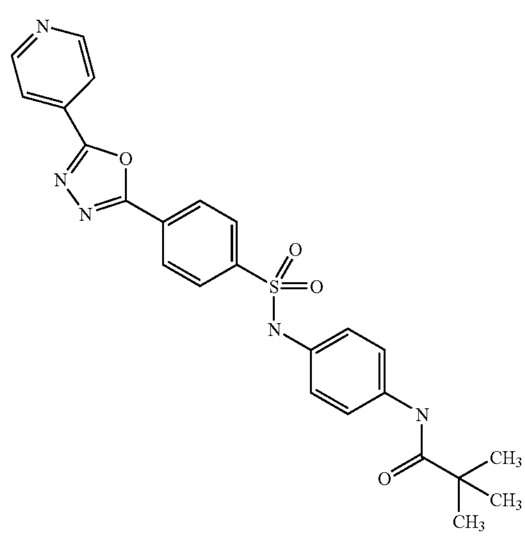 | 477.55 | 478 | 3.62 | 6 |

Example 131

1-Methyl-N-{4-[({3-[5-(2-pyridinyl)-1,3,4-thiadiazol-2-yl]phenyl}sulphonyl)amino]phenyl}cyclopropanecarboxamide

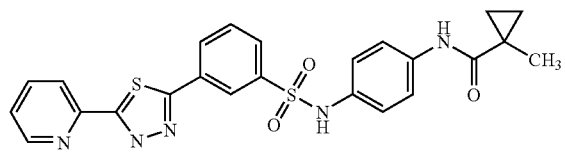

MW 491.59; m/z found: 490 (neg. ESI) HPLC Rt: 4.03 min. (HPLC method/instrument: 5) $^1$H-NMR (400 MHz, DMSO): δ=0.56–0.59 (m, 2 H), 1.01–1.06 (m, 2 H), 1.34 (s, 3 H), 7.04 (d, 2 H), 7.48 (d, 2 H), 7.63–7.65 (m, 1 H), 7.76 (t, 3H), 7.88 (d, 1H), 8.09 (dt, 1H), 8.26 (dt, 1H), 8.34 (d, 1H), 8.44 (t, 1H), 8.75–8.77 (m, 1H), 10.10 (s, 1 H), 10.27 (s, 1 H).

Example 132

N-(3-{[(4-{5-[6-(Acetylamino)-2-pyridinyl]-1,2,4-oxadiazol-3-yl}phenyl)sulphonyl]-amino}phenyl)-1-methylcyclopropanecarboxamide

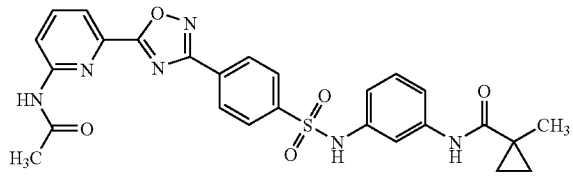

8.1 g (20.85 mmol) of amidoxime from Example VII are initially charged in 50 ml of THF, 4.13 g (22.94 mmol) of 2-aminoacetylpicolinic acid (Example IX) and 16.28 g (31.28 mmol) of PyBOP are then added, and 2.96 g (22.94 mmol) of N,N-diisopropylethylamine are then added dropwise. The mixture is stirred at room temperature for 16 h, and the reaction mixture is then concentrated under reduced pressure, taken up in dichloromethane and washed successively, in each case once, with 1 N hydrochloric acid and sat. sodium chloride solution. The organic phase is dried over sodium sulphate, filtered and concentrated under reduced pressure. The residue (8.26 g) is dissolved in 75 ml of N,N-dimethylformamide and stirred at 115° C. for 4 h. After cooling, 200 ml of ethyl acetate are added and the mixture is washed 1× with 1 N hydrochloric acid, 1× with sat. sodium chloride solution, 2× with sat. sodium bicarbonate solution and 1× with sat. sodium chloride solution. During washing, crystallization sets in in the organic phase. Accordingly, the organic phase is allowed to stand for 30 min and the precipitated crystals are filtered off with suction and washed with methanol [1. fraction, yield: 5.04 g (23% of theory)]. The mother liquor is dried over sodium sulphate, filtered and concentrated using a rotary evaporator. Stirring with dichloromethane gives two further fractions of crystalline product [fraction 2, yield: 3.5 g (16% of theory); fraction 3, yield: 1.1 g (5% of theory)]. The remaining mother liquor contains more product which can be purified chromatographically [yield: 1.01 g (5% of theory)].

HPLC: Rt=4.42 min (HPLC method/instrument 3) MW 550.59; m/z found: 551 $^1$H-NMR (200 MHz, DMSO-d$_6$): δ=11.00 (s, 1H); 10.41 (s, 1H); 9.18 (s, 1H); 8.40 (dd, 1H); 8.24 (d, 2H); 8.14–9.97 (m, 4H); 7.57 (t, 1H); 7.27 (d, 1H); 7.12 (t, 1H); 6.78 (d, 1H); 2.15 (s, 3H); 1.37 (s, 3H); 1.08–1.03 (m, 2H); 0.62–0.57 (m, 2H).

Example 133

N-(3-{[(4-{5-[6-(Acetylamino)-2-pyridinyl]-1,2,4-oxadiazol-3-yl}phenyl)sulphonyl]-amino}phenyl)-3-fluoro-2,2-dimethylpropanamide

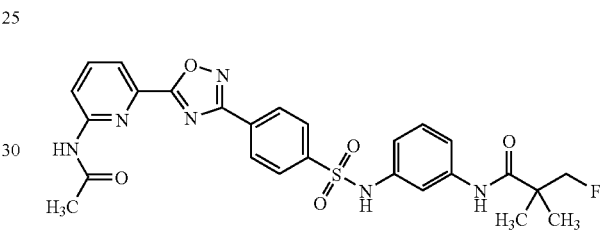

7.80 g (19.1 mmol) of the amidoxime from Example V are initially charged in 100 ml of THF, 3.78 g (21.0 mmol) of 2-aminoacetylpicolinic acid and 14.91 g (28.6 mmol) of PyBOP are then added, and 2.71 g (21.0 mmol) of N,N-diisopropylethylamine are finally added dropwise. The mixture is stirred at 40° C. for 16 h and the reaction mixture is then concentrated under reduced pressure, taken up in ethyl acetate and washed successively, in each case twice, with 1 N hydrochloric acid and sat. sodium chloride solution. The organic phase is dried over sodium sulphate, filtered and concentrated under reduced pressure. The product is purified by filtration through silica gel 0.60 using the mobile phase ethyl acetate. The resulting product (9.9 g) is dissolved in 90 ml of N,N-dimethylformamide and stirred at 115° C. for 4 h. After cooling, the solvent is removed under reduced pressure, 200 ml of ethyl acetate are added and the mixture is washed 1× with 1 N hydrochloric acid, 1× with sat. sodium chloride solution, 2× with sat. sodium bicarbonate solution and 1× with sat. sodium chloride solution. The organic phase is dried over sodium sulphate and the solvent is then removed. During concentration, a precipitate is formed, and the suspension is then diluted with dichloromethane and the precipitate is separated off and washed with dichloromethane.

Yield: 5.4 g (55% of theory) HPLC: Rt=4.44 min (HPLC method/instrument 3) MW 552.58; m/z found: 553 $^1$H-NMR (200 MHz, DMSO-d$_6$): δ=10.99 (s, 1H); 10.43 (s, 1H); 9.36 (s, 1H); 8.40 (dd, 1H); 8.25 (d, 2H); 8.13–7.98 (m, 4H); 7.59 (t, 1H); 7.30 (d, 1H); 7.15 (t, 1H); 6.81 (d, 1H); 4.48 (d, 1H); 2.16 (s, 3H); 1.21 (s, 6H).

Example 134

N-{3-[({4-[5-(6-Amino-2-pyridinyl)-1,2,4-oxadiazol-3-yl]phenyl}sulphonyl)amino]-phenyl}-1-methylcyclopropanecarboxamide

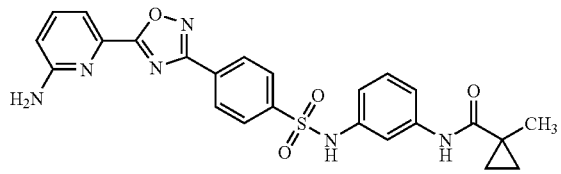

15 g (28.16 mmol) of the compound from Example 132 are suspended in 370 ml of ethanol, and 279 ml (281.7 mmol) of 1 N aqueous sodium hydroxide solution are added. The mixture is stirred at 45° C. for 5 h (the suspension dissolves slightly), and the mixture is then, in an ice bath, adjusted to pH=5 using 1 N hydrochloric acid, and the precipitated crystals are filtered off, washed with water and ethanol and dried at 80° C. under high vacuum for 16 h.

Yield: 12 g (85.5% of theory) HPLC: Rt=4.06 min (HPLC method/instrument 3) MW 490.54; m/z found: 491 $^1$H-NMR (200 MHz, DMSO-$d_6$): δ=10.40 (s, 1H); 9.15 (s, 1H); 8.21 (d, 2H); 7.96 (d, 2H); 7.68–7.43 (m, 3H); 7.25 (d, 1H); 7.10 (t, 1H); 6.76 (t, 2H); 6.56 (d, 2H); 1.36 (s, 3H); 1.08–1.03 (s, 2H); 0.62–0.57 (m, 2H).

Example 135

N-{3-[({4-[5-(6-Amino-2-pyridinyl)-1,2,4-oxadiazol-3-yl]phenyl}sulphonyl)amino]-phenyl}-3-fluoro-2,2-dimethylpropanamide

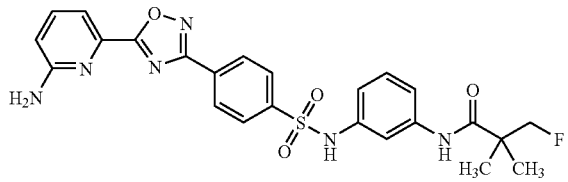

19.3 g (34.9 mmol) of the compound from Example 133 are taken up in 290 ml of a mixture of water/conc. hydrochloric acid (1:1 v/v), and the suspension is stirred at 100° C. for 4 h. The suspension is then filtered, the filter cake is stirred between sat. sodium bicarbonate solution and ethyl acetate, the organic phase is separated off and concentrated using a rotary evaporator and the crude product is purified chromatographically [silica gel 60, mobile phase toluene/acetone (8:2 v/v)]. To remove adhering residual solvent, the clean fractions are combined (6.8 g), dissolved, at 0° C., in 130 ml of 1 N aqueous sodium hydroxide solution (turbid solution), and this solution is acidified to pH=5 using 1 N hydrochloric acid. The precipitate is filtered off, washed with water and dried under high vacuum.

Yield: 6.4 g (36% of theory) HPLC: Rt=4.09 min (HPLC method/instrument 3) MW 510.55; m/z found: 511 $^1$H-NMR (500 MHz, DMSO-$d_6$): δ=10.42 (s, 1H); 9.33 (s, 1H); 8.21 (d, 2H); 7.97 (d, 2H); 7.64 (t, 1H); 7.53 (s, 1H); 7.45 (d, 1H); 7.27 (d, 1H); 7.12 (t, 1H); 6.78 (d, 1H); 6.73 (d, 1H); 6.57 (s, 2H); 4.48 (d, 2H); 1.21 (s, 6H).

Example 136

Ethyl ({6-[3-(4-{[(3-{[(1-methylcyclopropyl)carbonyl]amino}phenyl)amino]-sulphonyl}-phenyl)-1,2,4-oxadiazol-5-yl]-2-pyridinyl}amino)(oxo)-acetate

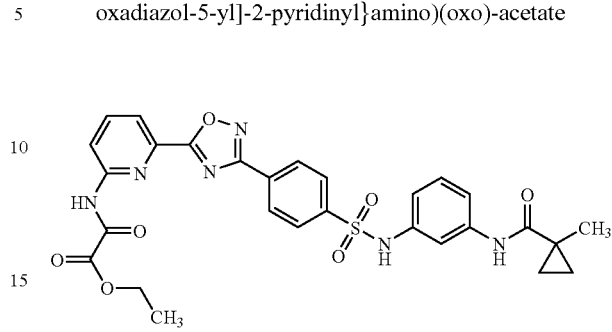

Under argon, 400 mg (0.82 mmol) of the compound from Example 134 are dissolved in 12 ml of dichloromethane, and 70 mg (0.09 mmol) of pyridine and 150 mg (1.1 mmol) of monoethyl oxalyl chloride are added with stirring. The solution is stirred at room temperature for another 30 min. The reaction mixture is then added to 25 ml of pH 7 buffer, the aqueous phase is extracted three times with dichloromethane and the combined organic phases are washed in each case twice with sat. sodium chloride solution, sodium bicarbonate solution and sat. sodium chloride solution. The organic phase is separated off, dried over sodium sulphate and concentrated under reduced pressure. The crude product is purified by chromatography on silica gel 60 using the mobile phase toluene/ethyl acetate (1:1 v/v).

Yield: 349 mg (72% of theory) HPLC: Rt=4.57 min (HPLC method/instrument 3) MW 590.61; m/z found: 591 $^1$H-NMR (200 MHz, DMSO-$d_6$): δ=11.41 (s, 1H); 10.42 (s, 1H); 9.20 (s, 1H); 8.28–8.16 (m, 6H); 8.00 (d, 1H); 7.60 (s, 1H); 7.28 (d, 1H); 7.13 (t, 1H); 6.79 (d, 1H); 4.32 (q, 2H); 1.37–1.29 (m, 6H); 1.08–1.03 (m, 2H); 0.63–0.58 (m, 2H).

Example 137

({6-[3-(4-{[(3-{[(1-Methylcyclopropyl)carbonyl]amino}phenyl)amino]sulphonyl}-phenyl)-1,2,4-oxadiazol-5-yl]-2-pyridinyl}amino)(oxo)-acetic acid

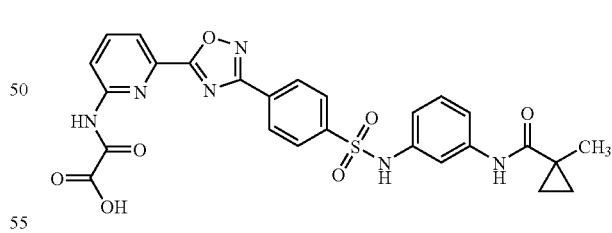

152 mg (0.26 mmol) of the compound from Example 136 are taken up in 7.5 ml of dioxane, and 0.75 ml (0.75 mmol) of 1 N aqueous sodium hydroxide solution is added. The mixture is stirred at room temperature for 16 h and then carefully acidified to pH=7 using 1 N hydrochloric acid, and the solvent is removed under reduced pressure. The crude product is purified by preparative HPLC (CromSil C18, 250×30 mm, flow rate 50 ml/min, runtime 35 min, detection at 254 nm, gradient 10% acetonitrile @ 3 min->90% acetonitrile @ 31 min->90% acetonitrile @ 34 min->10% acetonitrile @ 34.01 min).

Yield: 35 mg (24% of theory) HPLC: Rt=4.23 min (HPLC method/instrument 3) MW 562.56; m/z found: 563 ¹H-NMR (200 MHz, DMSO-d$_6$): δ=11.71 (s, 1H); 10.40 (s, 1H); 9.16 (s, 1H); 8.40 (d, 1H); 8.26 (d, 2H); 8.13 (t, 1H); 8.04–7.94 (m, 3H); 7.53 (s, 1H); 7.24 (d, 1H); 7.14 (t, 1H); 6.77 (d, 1H); 1.36 (s, 3H); 1.08–1.03 (m, 2H); 0.62–0.57 (m, 2H).

Example 138

1-Methyl-N-[3-({[4-(5-{6-[(methylsulphonyl)amino]-2-pyridinyl}-1,2,4-oxadiazol-3-yl)phenyl]sulphonyl}amino)phenyl]cyclopropanecarboxamide

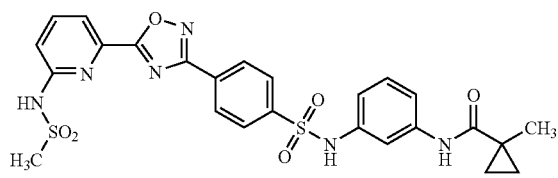

200 mg (0.38 mmol) of the compound from Example 134 are dissolved in 10 ml of THF and, under argon, 0.5 ml (6.18 mmol) of pyridine and 90 mg (0.75 mmol) of methanesulphonyl chloride are added. The mixture is stirred at room temperature for 16 h, the solvent is then removed under reduced pressure, the residue is taken up in 5 ml of methanol and again concentrated under reduced pressure, and the crude product is purified by preparative HPLC (CromSil C18, 250×30 mm, flow rate 50 ml/min, runtime 35 min, detection at 254 nm, gradient 10% acetonitrile @ 3 min->90% acetonitrile @ 31 min->90% acetonitrile @ 34 min->10% acetonitrile @ 34.01 min).

Yield: 82 mg (30% of theory) HPLC: Rt=4.30 min (HPLC method/instrument 3) MW 588.64; m/z found: 589 ¹H-NMR (200 MHz, DMSO-d$_6$): δ=10.99 (br s, 1H); 10.48 (br s, 1H); 9.36 (s, 1H); 8.25 (d, 1H); 8.09–7.96 (m, 4H); 7.59–7.57 (m, 1H); 7.33–7.11 (m, 6H); 6.81 (d, 1H); 4.43 (d, 2H); 3.48 (s, 3H); 1.27–1.14 (m, 6H).

Further 1,2,4-oxadiazole derivatives attached via position 3 and prepared according to the processes according to the invention are listed in Table 4:

| Ex. No. | Structure | MW | m/z found | HPLC Rt [min] | HPLC method |
|---|---|---|---|---|---|
| 139 | 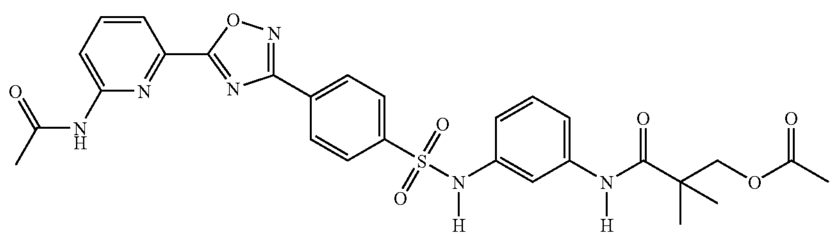 | 592 | 593 | 2.45 | 8 |
| 140 | 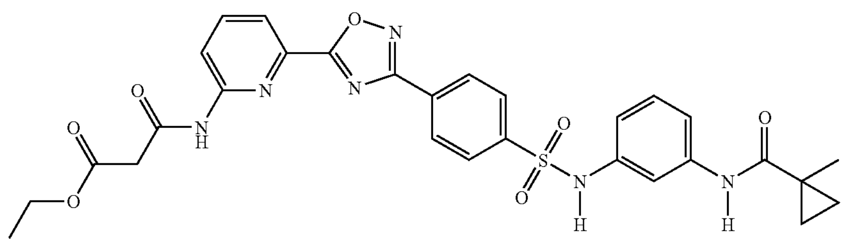 | 604 | 605 | 2.59 | 8 |
| 141 | 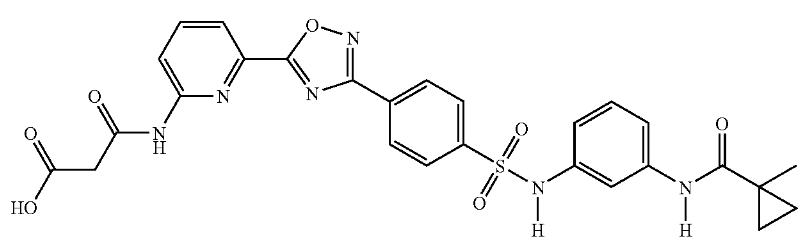 | 576 | 577 | 2.4 | 8 |
| 142 | 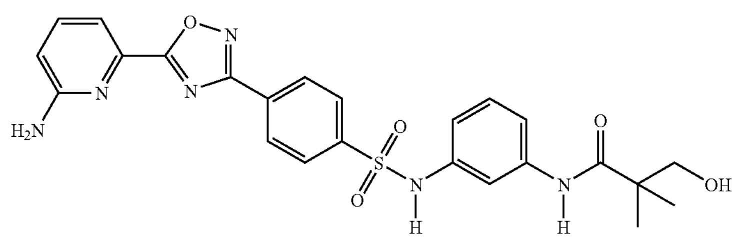 | 508 | 509 | 2.22 | 8 |

-continued

| Ex. No. | Structure | MW | m/z found | HPLC Rt [min] | HPLC method |
|---|---|---|---|---|---|
| 143 | 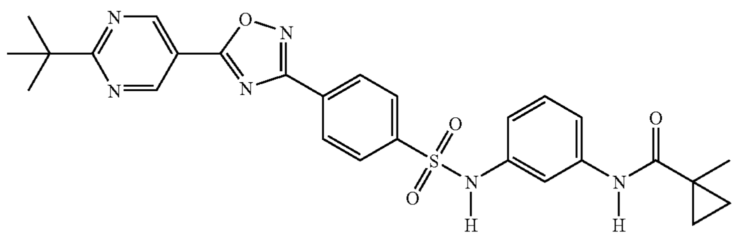 | 532 | | | |
| 144 | 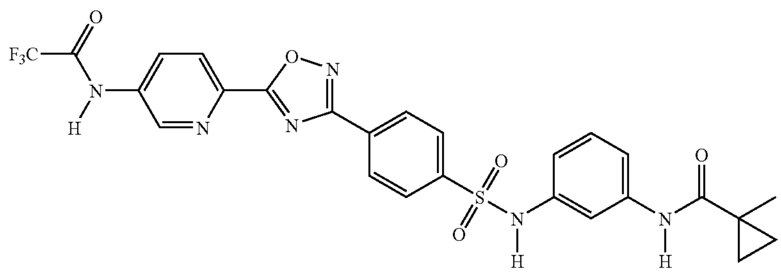 | 586 | | | |
| 145 | 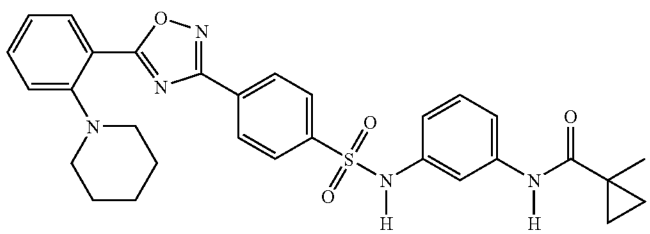 | 559 | 560 | 2.72 | 8 |
| 146 | 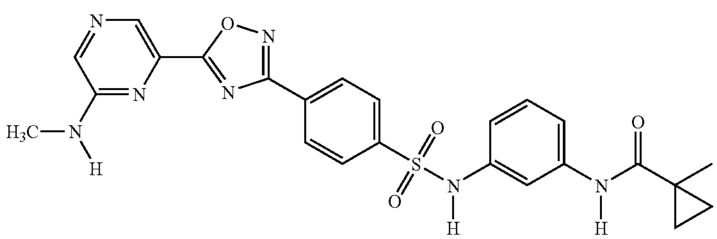 | 505 | 506 | 4.38 | 3 |
| 147 | 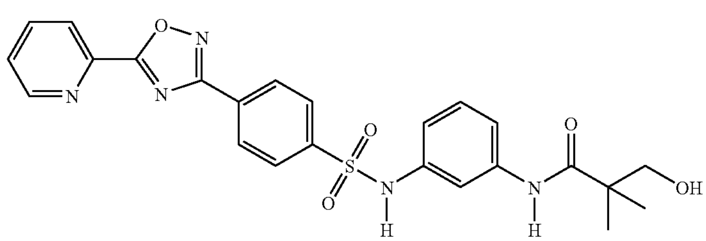 | 490 | | | |
| 148 | 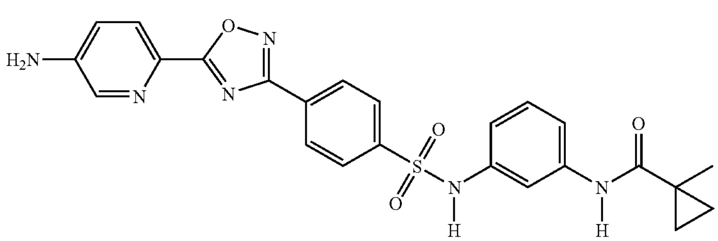 | 535 | | | |

-continued

| Ex. No. | Structure | MW | m/z found | HPLC Rt [min] | HPLC method |
|---|---|---|---|---|---|
| 149 | 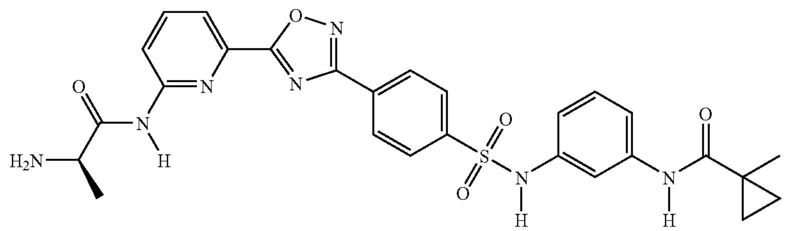 | 561 | 562 | 4.05 | 3 |
| 150 | 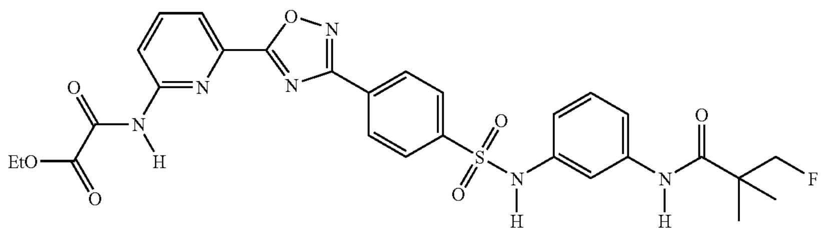 | 610 | 611 | 4.59 | 3 |
| 151 | 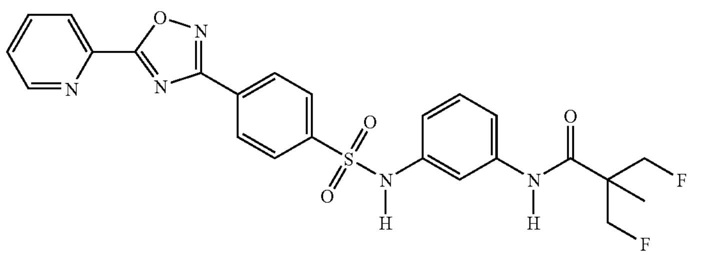 | 513 | 514 | 2.49 | 8 |
| 152 | 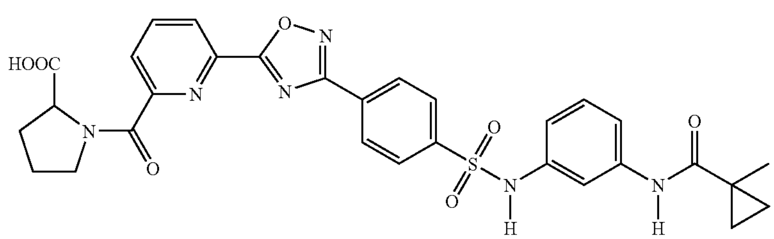 | 616 | 617 | | |
| 153 | 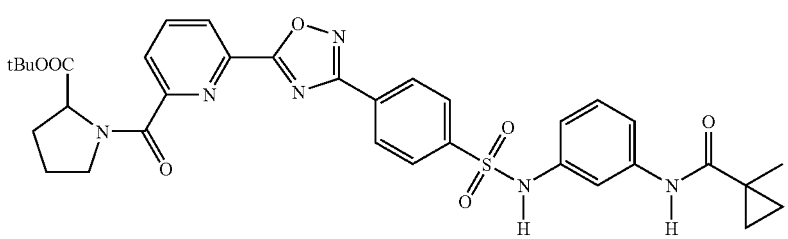 | 672 | 673 | 4.61 | 3 |
| 154 | 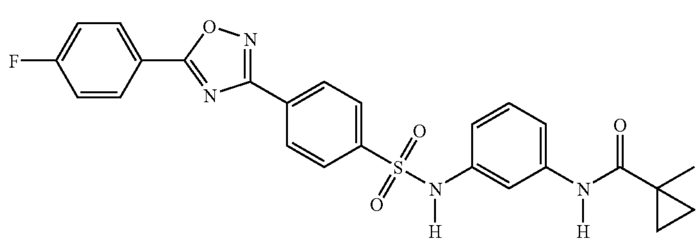 | 492 | 493 | 2.79 | 8 |

The compounds listed in the working examples and tables were characterized using the LC-MS and HPLC methods described below:

Method 1:
Column: Kromasil C18, L-R temperature: 30° C., flow rate=0.75 ml min$^{-1}$, mobile phase: A=0.01 M HClO$_4$, B=CH$_3$CN, gradient:→0.5 min 98% A→4.5 min 10% A→6.5 min 10% A Method 2:
Column: Kromasil C18 60×2 mm, L-R temperature: 30° C., flow rate=0.75 ml min$^{-1}$, mobile phase: A=0.01 M H$_3$PO$_4$, B=CH$_3$CN, gradient:→0.5 min 90% A→4.5 min 10% A→6.5 min 10% A Method 3:
Column: Kromasil C18 60×2 mm, L-R temperature: 30° C., flow rate=0.75 ml min$^{-1}$, mobile phase: A=0.005 M HClO$_4$, B=CH$_3$CN, gradient:→0.5 min 98% A→4.5 min 10% A→6.5 min 10% A Method 4:
Column: symmetry C18 2.1×150 mm, column oven: 50° C., flow rate=0.6 ml min$^{-1}$, mobile phase: A=0.6 g 30% strength HCl/1 water, B=CH$_3$CN, gradient: 0.0 min 90% A→4.0 min 10% A→9 min 10% A Method 5:
LC-MS:MHZ-2Q, Instrument Micromass Quattro LCZ Column: Symmetry C18 50 mm×2.1 mm, 3.5 μm, temperature: 40° C., flow rate=0.5 ml min$^{-1}$, mobile phase A=CH$_3$CN+ 0.1% formic acid, mobile phase B=water+0.1% formic acid, gradient: 0.0 min 10% A→4 min 90% A→6 min 90% A Method 6:
LC-MS: MHZ-2P, Instrument Micromass Platform LCZ Column: Symmetry C18 50 mm×2.1 mm, 3.5 μm, temperature: 40° C., flow rate=0.5 ml min$^{-1}$, mobile phase A=CH$_3$CN+0.1% formic acid, mobile phase B=water+0.1% formic acid, gradient: 0.0 min 10% A→4 min 90% A→6 min 90% A Method 7:
LC-MS: MHZ-7Q, Instrument Micromass Quattro LCZ Column: Symmetry C18 50 mm×2.1 mm, 3.5 μm, temperature: 40° C., flow rate=0.5 ml min$^{-1}$, mobile phase A=CH$_3$CN+0.1% formic acid, mobile phase B=water+0.1% formic acid, gradient: 0.0 min 5% A→1 min 5% A→5 min 90% A→6 min 90% A Method 8:
Column: Symmetry C18 2.1×150 mm, column oven: 50° C., flow rate=0.9 ml min$^{-1}$, mobile phase: A=0.3 g 30% strength HCl/1 water, B=CH$_3$CN, gradient: 0.0 min 90% A→3.0 min 10% A→6.0 min 10% A Method 9:
HP1100, column: LiChroCart 75-5 LiChrospher 100 RP-18 5 μm, column oven: 40° C., flow rate=2.5 ml min$^{-1}$, mobile phase: A=water having 0.05% TFA, B=CH$_3$CN having 0.05% TFA, gradient: 0.0 min 90% A→0.05 min 90% A→5.0 min 5% A→7.0 min 5% A→7.05 min 90% A→8.0 min 90% A

The invention claimed is:

1. A compound of the general formula (I)

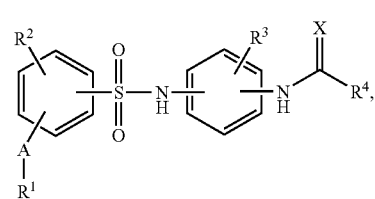

in which

R$^2$ and R$^3$ are identical or different and represent hydrogen, hydroxyl, halogen, nitro, cyano, trifluoromethyl, trifluoromethoxy, (C$_1$–C$_6$)-alkyl, (C$_1$–C$_6$)-alkoxy or represent a group of the formula

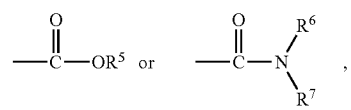

in which

R$^5$, R$^6$ and R$^7$ are identical or different and each represents hydrogen or (C$_1$–C$_6$)-alkyl which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring via a C atom and has one to three heteroatoms selected from the group consisting of N, O and S, R$^1$ represents (C$_6$–C$_{10}$)-aryl, 5- to 10-membered heteroaryl or 5- to 10-membered heterocyclyl having in each case one to three heteroatoms selected from the group consisting of N, O and S, where R$^1$ may be substituted by up to three substituents selected from the group consisting of hydroxyl, amino, mono-(C$_1$–C$_6$)-alkylamino, di-(C$_1$–C$_6$)-alkylamino, halogen, nitro, cyano, oxo, (C$_1$–C$_6$)-alkyl which for its part may be substituted by amino or hydroxyl, (C$_1$–C$_6$)-alkoxy, phenyl, 5- or 6-membered heterocyclyl having up to two heteroatoms selected from the group consisting of N, O and S, 5- or 6-membered heteroaryl having one or more heteroatoms selected from the group consisting of N, O and S, —C(O)—O—R$^8$, —C(O)—NR$^9$R$^{10}$, —NH—C(O)—R$^{11}$, —NH—C(O)—C(O)—R$^{12}$ and —NH—SO$_2$—R$^{13}$, where R$^8$, R$^9$ and R$^{10}$ are identical or different and each represents hydrogen or (C$_1$–C$_6$)-alkyl, or R$^9$ and R$^{10}$ together with the nitrogen atom to which they are attached form a 5- or 6-membered heterocycle which may contain a further nitrogen or oxygen heteroatom and which may be mono- or disubstituted by identical or different substituents from the group consisting of (C$_1$–C$_4$)-alkyl which for its part is optionally substituted by hydroxyl or amino, amino, hydroxyl, (C$_1$–C$_4$)-alkoxy, oxo, carboxyl and (C$_1$–C$_4$)-alkoxycarbonyl, $R^{11}$ and $R^{12}$ are identical or different and each represents trifluoromethyl, $(C_1-C_6)$-alkoxy, or hydroxyl or represents $(C_1-C_6)$-alkyl which is optionally mono- or disubstituted by identical or different constituents from the group consisting of amino, $(C_1-C_6)$-alkoxycarbonylamino, mono-$(C_1-C_6)$-acylamino, hydroxyl, amidino, guanidino, $(C_1-C_6)$-alkoxycarbonyl, carboxyl and phenyl, and $R^{13}$ represents $(C_1-C_6)$-alkyl or $(C_6-C_{10})$-aryl which may in each case be substituted by halogen, amino, hydroxyl, $(C_1-C_4)$-alkoxy or $(C_1-C_4)$-alkyl, $R^4$ represents $(C_1-C_6)$-alkyl which may be substituted up to three times by identical or different substituents from the group consisting of amino, hydroxyl, halogen, $(C_1-C_6)$-alkoxy, $(C_1-C_5)$-alkanoyloxy and phenyl, which for its part is optionally mono- or disubstituted by identical or different substituents from the group consisting of halogen, nitro, cyano, amino and hydroxyl, or represents $(C_3-C_7)$-cycloalkyl which may be substituted up to three times by identical or different substituents from the group consisting of amino, hydroxyl, halogen, $(C_1-C_6)$-alkoxy and $(C_1-C_6)$-alkyl, which for its part is optionally substituted up to three times by identical or different substituents from the group consisting of amino, hydroxyl, halogen and $(C_1-C_6)$-alkoxy, or represents $(C_6-C_{10})$-aryl which is optionally mono- or disubstituted by identical or different substituents from the group consisting of halogen, nitro, cyano, amino and hydroxyl, and in which X represents oxygen or sulphur, and in which nitrogen-containing heterocycles may also be present as N-oxides, or a tautomer, steroisomer, mixture of steroisomer, or pharmacologically acceptable salt thereof.

2. The compound of the general formula (I) according to claim 1, in which $R^2$ and $R^3$ are identical or different and represent hydrogen, hydroxyl, halogen, nitro, cyano, trifluoromethyl, trifluoromethoxy, $(C_1-C_6)$-alkyl, $(C_1-C_6)$-alkoxy or represent a group of the formula

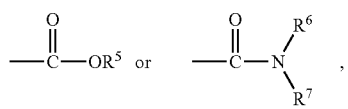

in which $R^5$, $R^6$ and $R^7$ are identical or different and each represents hydrogen of $(C_1-C_6)$-alkyl, which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring via a C atom and has one to three heteroatoms selected from the group consisting of N, O and S, $R^1$ represents $(C_6-C_{10})$-aryl, 5- to 10-membered heteroaryl or 5- to 10-membered heterocyclyl having in each case one to three heteroatoms selected from the group consisting of N, O and S, where $R^1$ may be substituted by up to three substituents selected from the group consisting of hydroxyl, amino, mono-$(C_1-C_6)$-alkylamino, di-$(C_1-C_6)$-alkylamino, halogen, nitro, cyano, oxo, $(C_1-C_6)$-alkyl which for its part may be substituted by amino or hydroxyl, $(C_1-C_6)$-alkoxy, phenyl, 5- or 6-membered heteroaryl having one or more heteroatoms selected from the group consisting of N, O and S, —C(O)—O—$R^8$, —C(O)—$NR^9R^{10}$ and —NH—C(O)—$R^{11}$, where $R^8$, $R^9$ and $R^{10}$ are identical or different and each represents hydrogen or $(C_1-C_6)$-alkyl, and $R^{11}$ represents $(C_1-C_6)$-alkyl which is optionally mono- or disubstituted by identical or different substituents from the group consisting of amino, hydroxyl, guanidino, carboxyl and phenyl, $R^4$ represents $(C_1-C_6)$-alkyl which may be substituted up to three times by identical or different substituents from the group consisting of amino, hydroxyl, halogen, $(C_1-C_6)$-alkoxy and phenyl, which for its part is optionally mono- or disubstituted by identical or different substituents from the group consisting of halogen, nitro, cyano, amino and hydroxyl, represents $(C_3-C_7)$-cycloalkyl which may be substituted up to three times by identical or different substituents from the group consisting of amino, hydroxyl, halogen, $(C_1-C_6)$-alkoxy and $(C_1-C_6)$-alkyl, which for its part is optionally substituted up to three times by identical or different substituents from the group consisting of amino, hydroxyl, halogen and $(C_1-C_6)$-alkoxy, or represents $(C_6-C_{10})$-aryl which is optionally mono- or disubstituted by identical or different substituents from the group consisting of halogen, nitro, cyano, amino and hydroxyl, and in which X represents oxygen or sulphur, and in which nitrogen-containing heterocycles may also be present as N-oxides, or a tautomer, stereoisomer, mixture of stereoisomers, or pharmacologically acceptable salt thereof.

3. The compound of the general formula (I) according to claim 1, in which $R^2$ and $R^3$ are identical or different and represent hydrogen, hydroxyl, halogen, nitro, cyano, trifluoromethyl, trifluoromethoxy, $(C_1-C_6)$-alkyl, $(C_1-C_6)$-alkoxy or represent a group of the formula

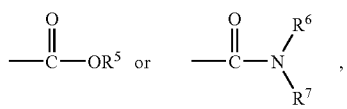

in which $R^5$, $R^6$ and $R^7$ are identical or different and each represents hydrogen or $(C_1-C_6)$-alkyl, which for its part may be substituted by one or two substituents selected from the group consisting of hydroxyl, halogen, cyano, trifluoromethyl and trifluoromethoxy, A represents five- or six-membered heteroaryl, which is attached to the adjacent phenyl ring, via a C atom and has one to three heteroatoms selected from the group consisting of N, O and S, R¹ represents $(C_6-C_{10})$-aryl, 5- to 10-membered heteroaryl or 5- to 10-membered heterocyclyl having in each case one to three heteroatoms selected from the group consisting of N, O and S, where R¹ may be substituted by up to three substituents selected from the group consisting of hydroxyl, amino, mono-$(C_1-C_6)$-alkylamino, di-$(C_1-C_6)$-alkylamino, halogen, nitro, cyano, oxo, $(C_1-C_6)$-alkyl which for its part may be substituted by amino or hydroxyl, $(C_1-C_6)$-alkoxy, phenyl, 5- or 6-membered heteroaryl having one or more heteroatoms selected from the group consisting of N, O and S, —C(O)—O—R⁸, —C(O)—NR⁹R¹⁰ and —NH—C(O)—R¹¹, where R⁸, R⁹ and R¹⁰ are identical or different and each represents hydrogen or $(C_1-C_6)$-alkyl, and R¹¹ represents $(C_1-C_6)$-alkyl, which is optionally mono- or disubstituted by identical or different substituents from the group consisting of amino, hydroxyl, guanidino, carboxyl and phenyl, R⁴ represents $(C_1-C_6)$-alkyl which may be substituted up to three times by identical or different substituents from the group consisting of amino, hydroxyl, halogen, $(C_1-C_6)$-alkoxy and phenyl, which for its part is optionally mono- or disubstituted by identical or different substituents from the group consisting of halogen, nitro, cyano, amino and hydroxyl, represents $(C_3-C_7)$-cycloalkyl which may be substituted up to three times by identical or different substituents from the group consisting of amino, hydroxyl, halogen, $(C_1-C_6)$-alkoxy and $(C_1-C_6)$-alkyl, which for its part is optionally substituted up to three times by identical or different substituents from the group consisting of amino, hydroxyl, halogen and $(C_1-C_6)$-alkoxy, or represents $(C_6-C_{10})$-aryl which is optionally mono- or disubstituted by identical or different substituents from the group consisting of halogen, nitro, cyano, amino and hydroxyl, and in which X represents oxygen, and in which nitrogen-containing heterocycles may also be present as N-oxides, or a tautomer, stereoisomer, mixture of stereoisomers, or pharmacologically acceptable salt thereof.

4. The compounds of the general formula (I) according to claim 1, in which R² and R³ are identical or different and represent hydrogen or halogen, A represents the radical (A-I)

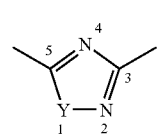

(A-I)

which is attached to the adjacent phenyl ring via one of the carbon atoms in position 3 or 5, and in which Y represents oxygen or sulphur, or A represents the radical (A-II)

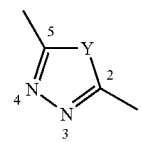

(A-II)

which is attached to the adjacent phenyl ring via one of the carbon atoms in position 2 or 5, and in which Y represents oxygen or sulphur, R¹ represents 5- to 10-membered heteroaryl or 5- or 10-membered heterocyclyl having in each case up to three heteroatoms selected from the group consisting of N, O and S, or represents phenyl, where R¹ may be substituted by one to three substituents selected from the group consisting of $(C_1-C_4)$-alkyl which for its part is optionally substituted by hydroxyl or amino, hydroxyl, oxo, halogen, amino, mono-$(C_1-C_4)$-alkylamino, di-$(C_1-C_4)$-alkylamino and —NH—C(O)—R¹¹, where R¹¹ represents $(C_1-C_6)$-alkyl which is optionally mono- or disubstituted by identical or different substituents from the group consisting of amino, hydroxyl, guanidino and carboxyl, R⁴ represents $(C_1-C_4)$-alkyl which may be substituted up to three times by identical or different substituents from the group consisting of amino, hydroxyl, fluorine, chlorine and $(C_1-C_4)$alkoxy, or represents $(C_3-C_5)$-cycloalkyl, which may be substituted up to three times by identical or different substituents from the group consisting of amino, hydroxyl, fluorine, chlorine, $(C_1-C_4)$-alkoxy and $(C_1-C_4)$-alkyl, which for its part is optionally substituted up to three times by identical or different substituents from the group consisting of amino, hydroxyl, fluorine, chlorine and $(C_1-C_4)$-alkoxy, and in which X represents oxygen or sulphur, and in which nitrogen-containing heterocycles may also be present as N-oxides, or a tautomer, stereoisomer, mixture of stereoisomers, or pharmacologically acceptable salt thereof.

5. The compound of the general formula (I) according to claim 1, in which R² and R³ are identical or different and represent hydrogen or halogen, A represents the radical (A-I)

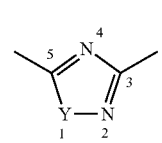

(A-I)

which is attached to the adjacent phenyl ring via one of the carbon atoms in position 3 or 5, and in which
Y represents oxygen or sulphur, or
A represents the radical (A-II)

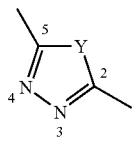
(A-II)

which is attached to the adjacent phenyl ring via one of the carbon atoms in position 2 or 5,
and in which
Y represents oxygen or sulphur,
$R^1$ represents 5- to 10-membered heteroaryl or 5- or 10-membered heterocyclyl having in each case up to three heteroatoms selected from the group consisting of N, O and S, or represents phenyl, where
$R^1$ may be substituted by one to three substituents selected from the group consisting of $(C_1-C_4)$-alkyl which for its-part is optionally substituted by hydroxyl or amino, hydroxyl, oxo, halogen, amino, mono-$(C_1-C_4)$-alkylamino, di-$(C_1-C_4)$-alkylamino and —NH—C(O)—$R^{11}$, where
$R^{11}$ represents $(C_1-C_6)$-alkyl which is optionally mono- or disubstituted by identical or different substituents from the group consisting of amino, hydroxyl, guanidino and carboxyl,
$R^4$ represents $(C_1-C_4)$-alkyl which may be substituted up to three times by identical or different substituents from the group consisting of amino, hydroxyl, fluorine, chlorine and $(C_1-C_4)$-alkoxy,
or represents $(C_3-C_5)$-cycloalkyl which may be substituted up to three times by identical or different substituents from the group consisting of amino, hydroxyl, fluorine, chlorine, $(C_1-C_4)$-alkoxy and $(C_1-C_4)$-alkyl, which for its part is optionally substituted up to three times by identical or different substituents from the group consisting of amino, hydroxyl, fluorine, chlorine and $(C_1-C_4)$-alkoxy,
and in which
X represents oxygen,
or a tautomer, stereoisomer, mixture of stereoisomers, or pharmacologically acceptable salt thereof.

6. The compound of the general formula (I) according to claim 1,
in which
$R^2$ and $R^3$ represent hydrogen,
A represents one of the radicals

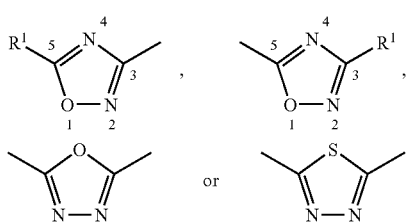

$R^1$ represents a radical selected from the group consisting of phenyl, pyridyl, pyrazinyl, thiazolyl, thiadiazolyl, quinolinyl, isoquinolinyl, oxazolyl, pyrazolyl, imidazolyl, pyrrolyl and indolyl, where
$R^1$ may be substituted by one or two substituents selected from the group consisting of methyl, aminomethyl, hydroxyl, bromine, chlorine, fluorine, amino, dimethylamino and —NH—C(O)—$R^{11}$, where
$R^{11}$ represents $(C_1-C_6)$-alkyl which is optionally mono- or disubstituted by identical or different substituents from the group consisting of amino, hydroxyl, guanidino and carboxyl,
$R^4$ represents tert-butyl which is optionally substituted up to three times by identical or different substituents from the group consisting of hydroxyl, fluorine and chlorine,
or represents cyclopropyl or cyclobutyl which are substituted by methyl, which for its part is optionally substituted by hydroxyl, fluorine or chlorine,
and in which
X represents oxygen,
and in which nitrogen-containing heterocycles may also be present as N-oxides,
or a tautomer, stereoisomer, mixture of stereoisomers, or pharmacologically acceptable salt thereof.

7. The compounds of the general formula (I) according to claim 1,
in which
$R^2$ and $R^3$ represent hydrogen,
A represents one of the radicals

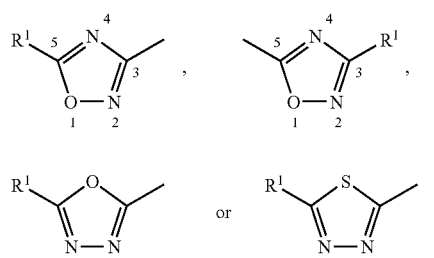

$R^1$ represents a radical selected from the group consisting of phenyl, pyridyl, pyrazinyl, thiazolyl, thiadiazolyl, quinolinyl, isoquinolinyl, oxazolyl, pyrazolyl, imidazolyl, pyrrolyl and indolyl, where
$R^1$ may be substituted by one or two substituents selected from the group consisting of methyl, aminomethyl, hydroxyl, bromine, chlorine, fluorine, amino, dimethylamino and —NH—C(O)—$R^{11}$, where
$R^{11}$ represents $(C_1-C_6)$-alkyl which is optionally mono- or disubstituted by identical or different substituents from the group consisting of amino, hydroxyl, guanidino and carboxyl,
$R^4$ represents tert-butyl which is optionally substituted up to three times by identical or different substituents from the group consisting of hydroxyl, fluorine and chlorine,
or represents cyclopropyl or cyclobutyl which are substituted by methyl, which for its part is optionally substituted by hydroxyl, fluorine or chlorine,
and in which
X represents oxygen.

8. The compound according to claim 1 of the general formula (Ia)

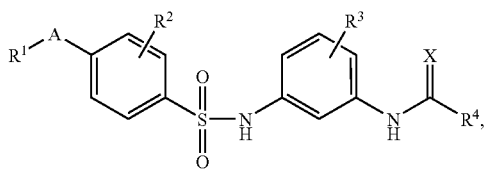
(Ia)

in which
R¹, R⁴, A and X are as defined in claim 1, and
R² and R³ are identical or different and represent hydrogen, hydroxyl, halogen, nitro, cyano, trifluoromethyl, trifluoromethoxy, ($C_1$–$C_6$)-alkyl or ($C_1$–$C_6$)-alkoxy.

9. The compound of the general formula (I) according to claim 1,
in which
R⁴ represents the radical

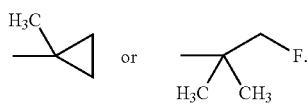

10. The compound of the general formula (I) according to claim 1,
in which
A represents a 1,2,4-oxadiazole attached via the 3-position.

11. The compound according to claim 1, selected from the group consisting of the following compounds:

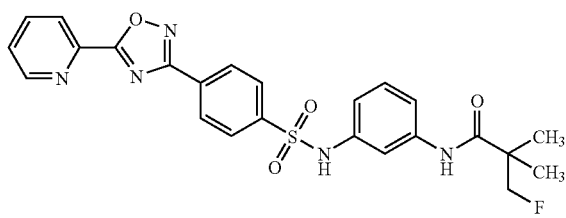

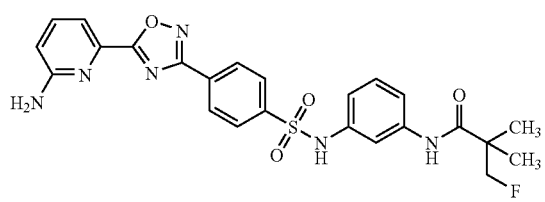

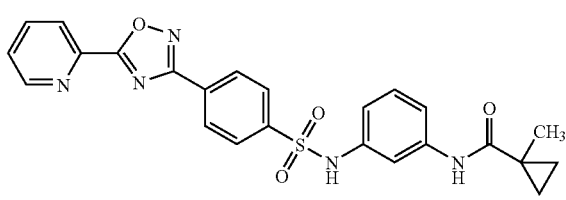

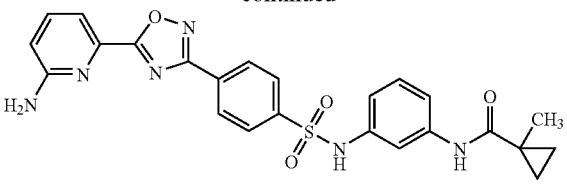

and

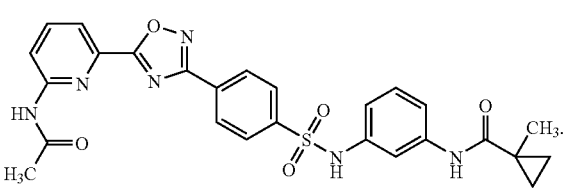

12. A process for preparing compounds of the general formula (I) according to claim 1, in which
A represents the radical (A-I)

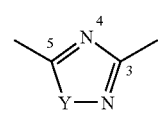
(A-I)

which is attached to the adjacent phenyl ring via one of the carbon atoms in position 3 or 5, and in which
Y represents oxygen, by
reacting an amidoxime of the general formula (D-1)

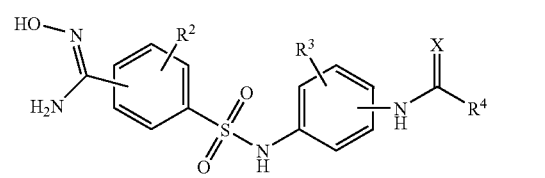
(D-1)

in which
X, R², R³ and R⁴ are as defined in claim 1,
with a carboxylic acid (E-1)

R¹—COOH   (E-1)

in which R¹ is as defined in claim 1, or
condensing a sulphonamide of the general formula (F-3)

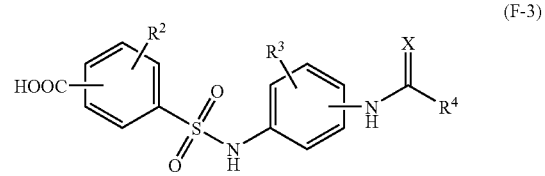
(F-3)

in which
X, $R^2$, $R^3$ and $R^4$ are as defined in claim 1,
with an amidoxime of the general formula (G-1)

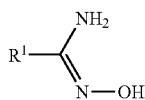
(G-1)

in which
$R^1$ is as defined in claim 1, giving a compound of the general formula (G-2)

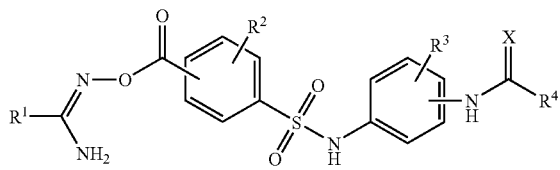
(G-2)

in which
$R^1$, $R^2$, $R^3$, $R^4$ and X are as defined in claim 1,
and subsequently cyclizing the compound (G-2) with elimination of water, giving the compound of the general formula (I).

13. A process for preparing compounds of the general formula (I) according to claim 1 in which
A represents the radical (A-II)

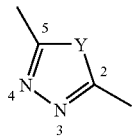
(A-II)

which is attached to the adjacent phenyl ring via one of the carbon atoms in position 2 or 5,
and in which
Y represents oxygen,
by cyclizing a hydrazide of the general formula (H-2)

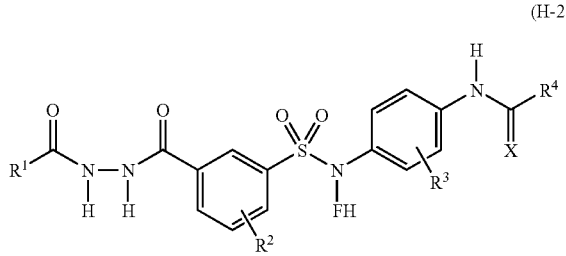
(H-2)

in which X, $R^1$, $R^2$, $R^3$ and $R^4$ are as defined in claim 1, and
FH represents hydrogen, an amino protective group or a polymeric support,
with elimination of water, to give a compound of the general formula (I).

14. A process for preparing compounds of the general formula (I) according to claim 1, in which
X represents oxygen,
A represents the radical (A-II)

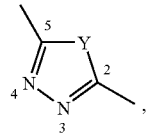
(A-II)

which is attached to the adjacent phenyl ring via one of the carbon atoms of position 2 or 5,
and in which
Y represents sulphur,
by cyclizing a hydrazide of the general formula (H-3)

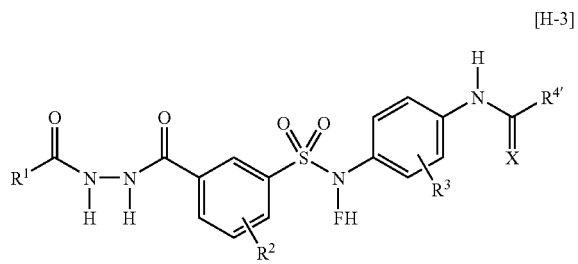
[H-3]

in which $R^1$, $R^2$, $R^3$ are as defined in claim 1,
FH represents hydrogen, an amino protective group or a polymeric support, and
$R^{4'}$ represents $(C_1–C_6)$-alkoxy, $(C_1–C_6)$-alkenoxy or aralkoxy,
in the presence of a thio donor, to give a compound of the general formula (I) in which Y represents sulphur, then removing group —C(O)—$R^{4'}$ and finally reacting with a compound of the general formula

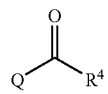

in which $R^4$ is as defined in claim 1 and Q represents a leaving group.

15. The process of claim 14 wherein said thio donor is Lawesson's reagent.

16. The process of claim 14 wherein said leaving group Q is halogen.

17. The process of claim 16 wherein said halogen is chlorine or bromine.

18. A method for treating cytomegalovirus infections comprising administering an effective amount of a compound of claim 1.

19. A pharmaceutical composition, comprising a compound of the general formula (I) according to claim 1 and a pharmaceutically acceptable carrier.

20. A compound of the general formula (Ia) according to claim 1

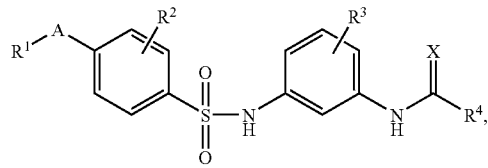
(Ia)

in which
$R^1$, $R^2$, $R^3$, $R^4$, A and X are as defined in claim 1.

* * * * *